United States Patent
Sand et al.

(10) Patent No.: US 10,814,003 B2
(45) Date of Patent: Oct. 27, 2020

(54) TRANSDERMAL CARRIER

(71) Applicant: Ampersand Biopharmaceuticals, Inc., Thousand Oaks, CA (US)

(72) Inventors: Bruce J. Sand, Westlake Village, CA (US); Ryan R. Beal, Thousand Oaks, CA (US); Philippe H. Burnham, Thousand Oaks, CA (US)

(73) Assignee: Ampersand Biopharmaceuticals, Inc., Thousand Oaks, CA (US)

(*) Notice: Subject to any disclaimer, the term of this patent is extended or adjusted under 35 U.S.C. 154(b) by 0 days.

(21) Appl. No.: 16/119,178

(22) Filed: Aug. 31, 2018

(65) Prior Publication Data

US 2018/0369387 A1    Dec. 27, 2018

Related U.S. Application Data

(63) Continuation of application No. 15/994,927, filed on May 31, 2018, now abandoned, which is a (Continued)

(51) Int. Cl.
*A61K 47/24* (2006.01)
*A61F 13/00* (2006.01)
(Continued)

(52) U.S. Cl.
CPC ........ *A61K 47/24* (2013.01); *A61F 13/00063* (2013.01); *A61F 13/02* (2013.01); *A61K 8/0291* (2013.01); *A61K 8/042* (2013.01); *A61K 8/34* (2013.01); *A61K 8/36* (2013.01); *A61K 8/37* (2013.01); *A61K 8/42* (2013.01); *A61K 8/4953* (2013.01); *A61K 8/553* (2013.01); *A61K 8/86* (2013.01); *A61K 9/0014* (2013.01); *A61K 9/06* (2013.01); *A61K 9/1075* (2013.01); *A61K 31/137* (2013.01); *A61K 31/167* (2013.01); *A61K 31/196* (2013.01); *A61K 31/245* (2013.01); *A61K 31/454* (2013.01); *A61K 31/7004* (2013.01); *A61K 33/00* (2013.01);
(Continued)

(58) Field of Classification Search
CPC ..... A61F 13/00063; A61Q 7/00; A61Q 19/08; A61K 47/28; A61K 47/24; A61K 47/14; A61K 47/12; A61K 47/10; A61K 33/00; A61K 31/7004; A61K 31/454; A61K 31/245; A61K 31/196
See application file for complete search history.

(56) References Cited

U.S. PATENT DOCUMENTS

| | | | | |
|---|---|---|---|---|
| 5,654,337 | A * | 8/1997 | Roentsch | A61K 9/0014 514/570 |
| 2007/0140996 | A1* | 6/2007 | Damiani | A61K 8/4946 424/59 |

(Continued)

OTHER PUBLICATIONS

Thomas Scientific ("L-α-Phosphatidylcholine", retrieved from https://www.thomassci.com/Chemicals/Reagent-P/_/FLUKA-L-And-Number-945-Phosphatidylcholine?q=Lecithin%20Soybean on Feb. 14, 2019. (Year: 2019).*

*Primary Examiner* — Jianfeng Song
(74) *Attorney, Agent, or Firm* — Entralta P.C.; Peter D. Weinstein; James F. Fleming

(57) ABSTRACT

Improved formulations for topical treatment that ensure at least localized transdermal or systemic delivery of an active agent through skin, nails or hair follicles are disclosed.

3 Claims, 21 Drawing Sheets

Expand Dermal Results — Crow's Feet

Before 15 mins After

Related U.S. Application Data continuation of application No. 14/757,703, filed on Dec. 23, 2015, now abandoned, which is a continuation-in-part of application No. PCT/US2014/072239, filed on Dec. 23, 2014.

(60) Provisional application No. 62/261,167, filed on Nov. 30, 2015, provisional application No. 62/238,012, filed on Oct. 6, 2015, provisional application No. 62/198,605, filed on Jul. 29, 2015, provisional application No. 62/198,599, filed on Jul. 29, 2015, provisional application No. 62/191,952, filed on Jul. 13, 2015, provisional application No. 62/187,756, filed on Jul. 1, 2015, provisional application No. 62/178,232, filed on Apr. 6, 2015, provisional application No. 62/178,192, filed on Apr. 2, 2015, provisional application No. 62/178,193, filed on Apr. 2, 2015, provisional application No. 62/177,814, filed on Mar. 24, 2015, provisional application No. 62/176,419, filed on Feb. 17, 2015, provisional application No. 62/176,415, filed on Feb. 17, 2015, provisional application No. 62/176,414, filed on Feb. 17, 2015, provisional application No. 62/176,417, filed on Feb. 17, 2015, provisional application No. 62/176,438, filed on Feb. 17, 2015, provisional application No. 62/176,418, filed on Feb. 17, 2015, provisional application No. 62/176,416, filed on Feb. 17, 2015.

(51) Int. Cl.

| | | |
|---|---|---|
| *A61Q 7/00* | (2006.01) | |
| *A61K 8/02* | (2006.01) | |
| *A61Q 19/08* | (2006.01) | |
| *A61K 47/28* | (2006.01) | |
| *A61K 47/14* | (2017.01) | |
| *A61K 47/12* | (2006.01) | |
| *A61K 47/10* | (2017.01) | |
| *A61K 33/00* | (2006.01) | |
| *A61K 31/7004* | (2006.01) | |
| *A61K 31/454* | (2006.01) | |
| *A61K 31/245* | (2006.01) | |
| *A61F 13/02* | (2006.01) | |
| *A61K 8/04* | (2006.01) | |
| *A61K 8/34* | (2006.01) | |
| *A61K 8/36* | (2006.01) | |
| *A61K 8/37* | (2006.01) | |
| *A61K 8/42* | (2006.01) | |
| *A61K 8/49* | (2006.01) | |
| *A61K 8/55* | (2006.01) | |
| *A61K 8/86* | (2006.01) | |
| *A61K 9/00* | (2006.01) | |
| *A61K 9/06* | (2006.01) | |
| *A61K 9/107* | (2006.01) | |
| *A61K 31/137* | (2006.01) | |
| *A61K 31/167* | (2006.01) | |
| *A61K 31/196* | (2006.01) | |

(52) U.S. Cl.
CPC .............. *A61K 47/10* (2013.01); *A61K 47/12* (2013.01); *A61K 47/14* (2013.01); *A61K 47/28* (2013.01); *A61Q 7/00* (2013.01); *A61Q 19/08* (2013.01)

(56) References Cited

U.S. PATENT DOCUMENTS

| | | | |
|---|---|---|---|
| 2009/0053290 A1* | 2/2009 | Sand | A61K 8/34 424/449 |
| 2009/0239814 A1* | 9/2009 | Manoharan | A61K 31/70 514/26 |
| 2011/0008474 A1* | 1/2011 | Boegli | A61K 36/53 424/739 |

* cited by examiner

Expand Dermal Results — Crow's Feet

Before 15 mins After

Follow-Up: Sustained Effect 4-8-15 Baseline 8-19-15

Expand Dermal Results — Crow's Feet

Before 15 mins After

Before (May 27, 2015)
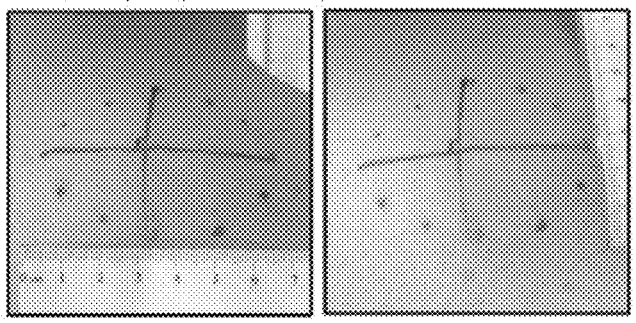
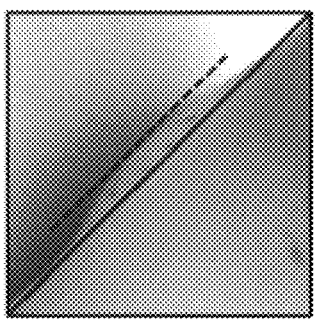
FIG. 4A
After (June 26, 2015)
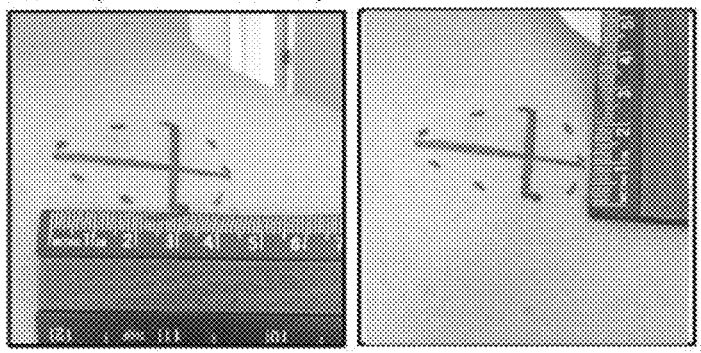
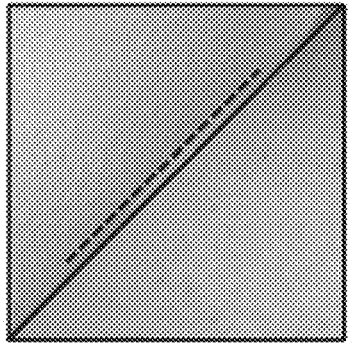
FIG. 4B

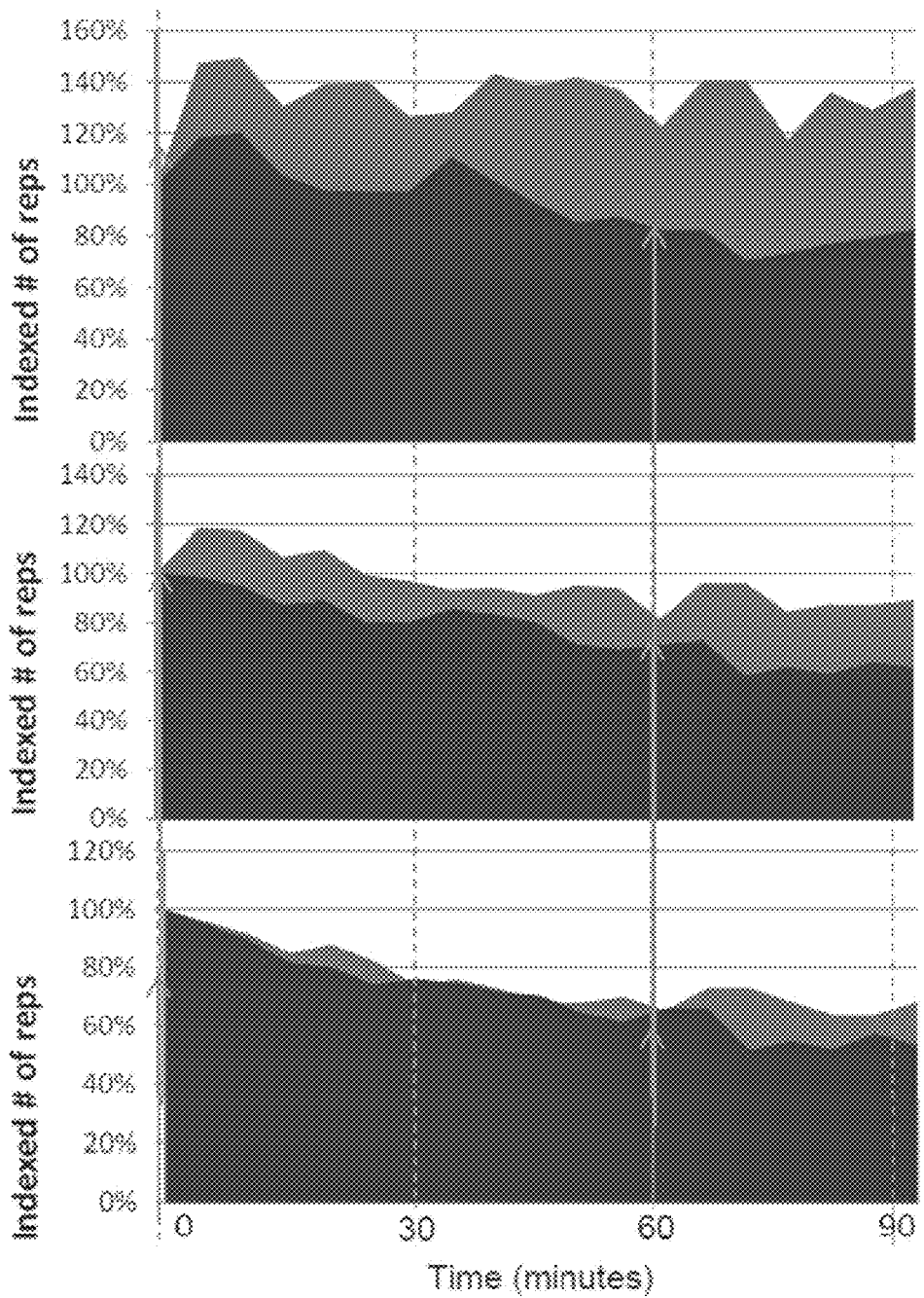
FIG. 6A Time to "burn"
FIG. 6B Time to threshold "pain"
FIG. 6C Max number of repetitions

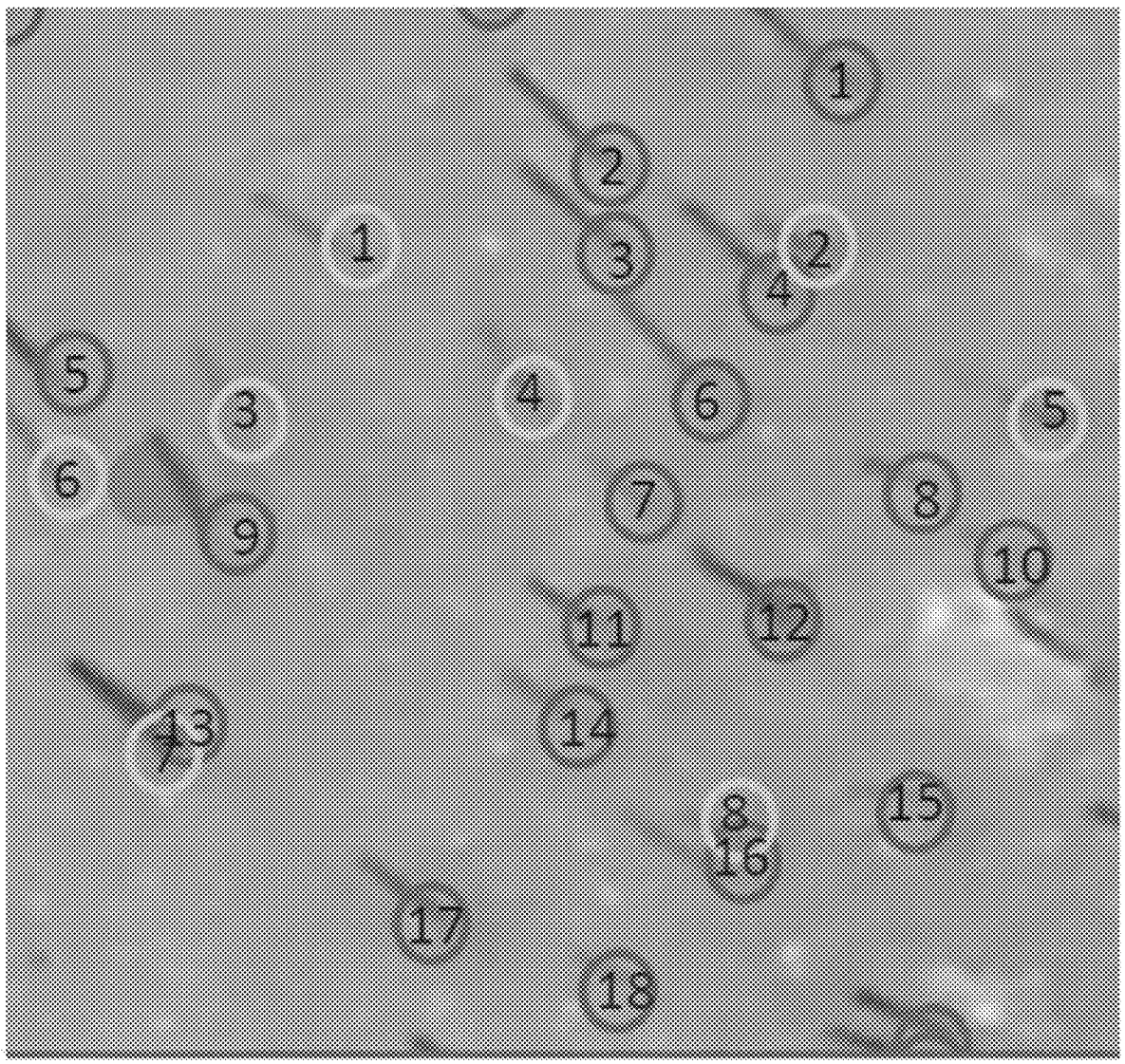
 Existing hair = 18
 New hair = 8 (44% increase)
FIG. 9B

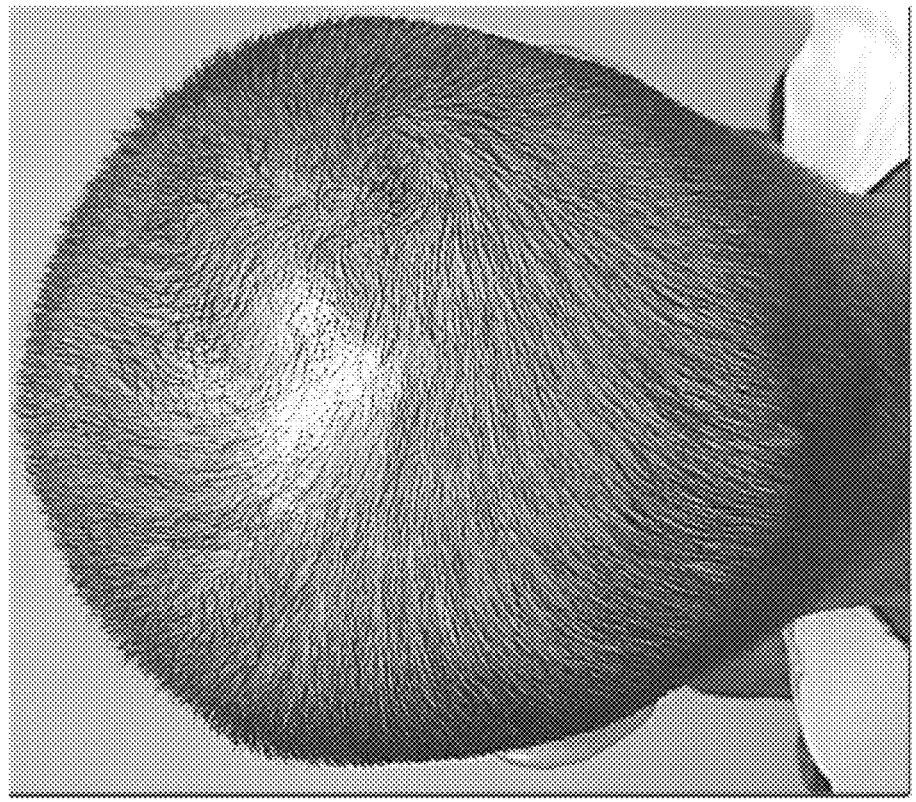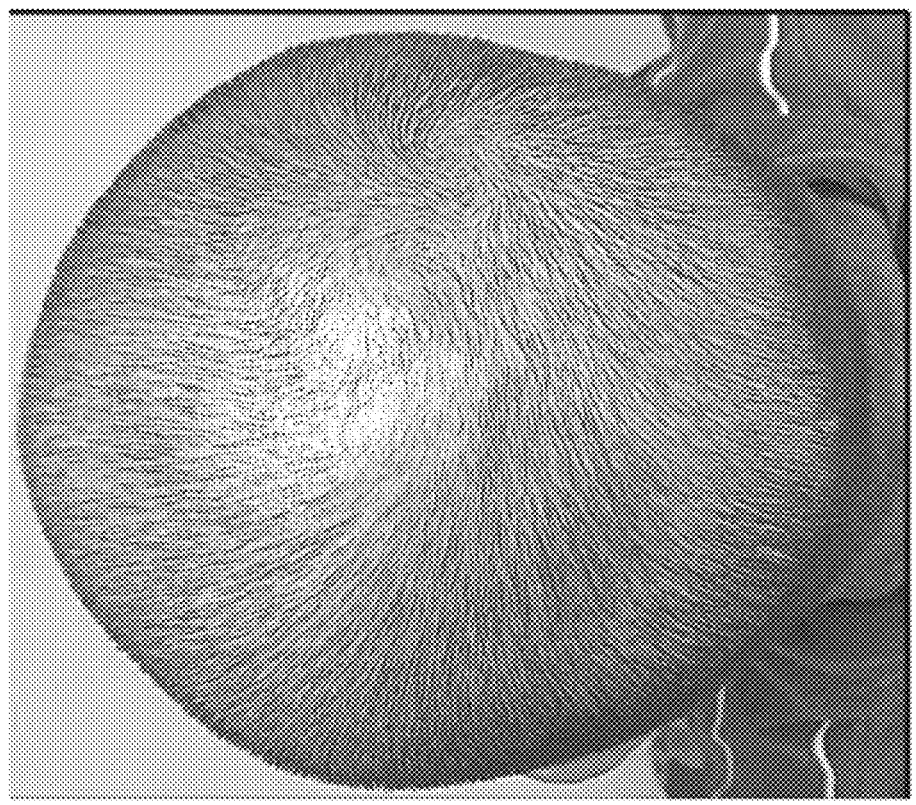
FIG. 12A

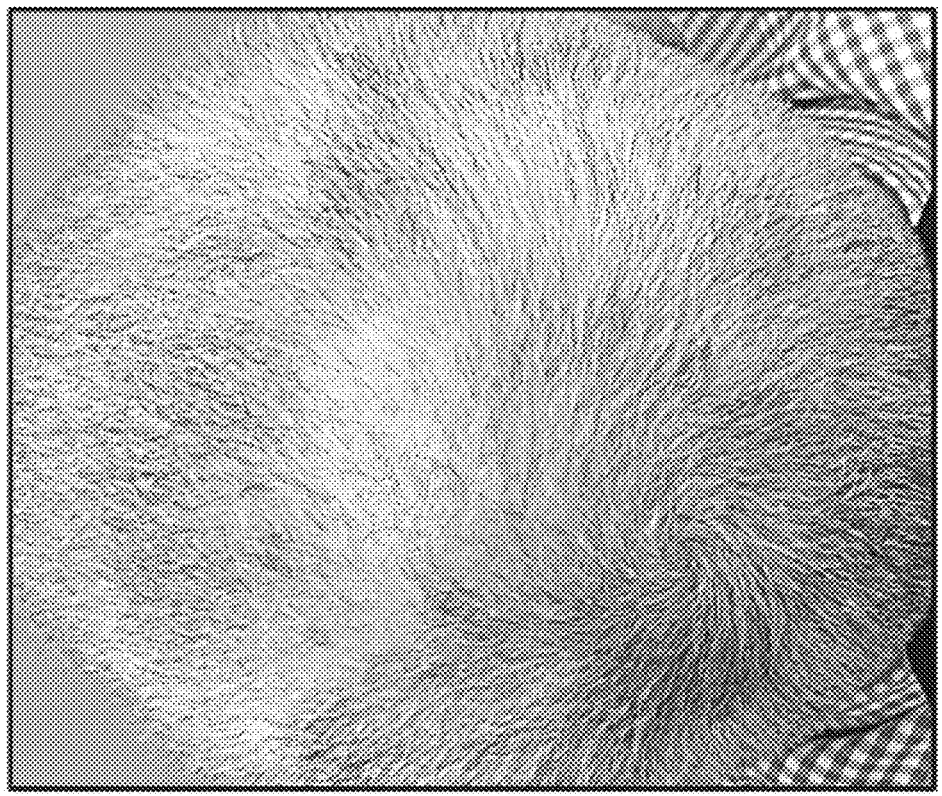
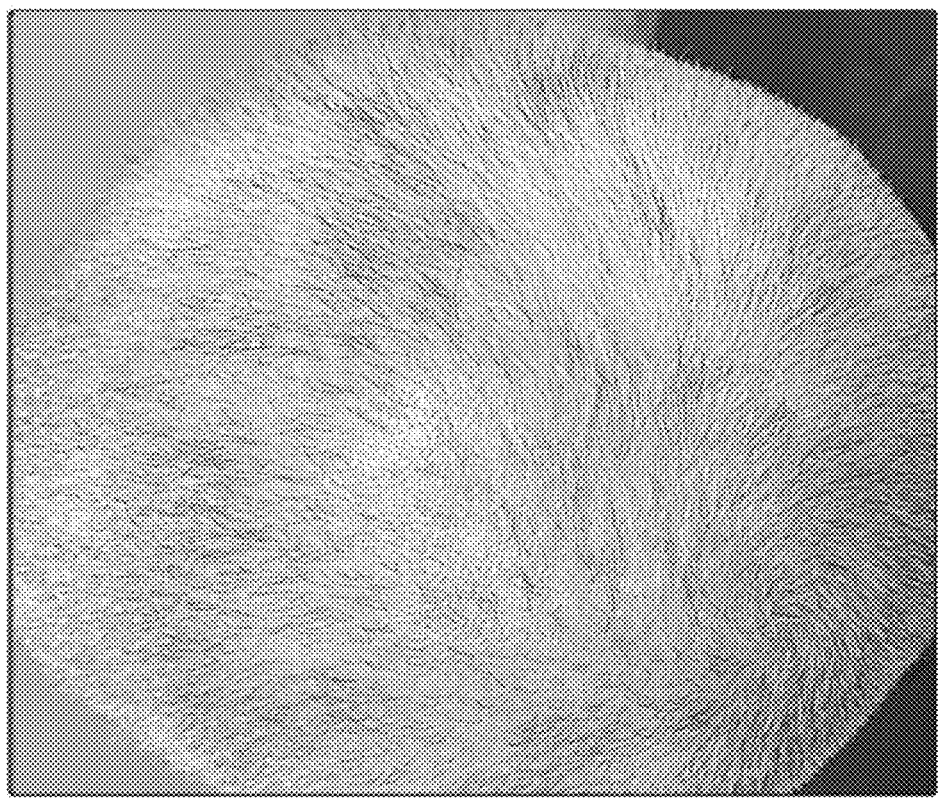
FIG. 12B

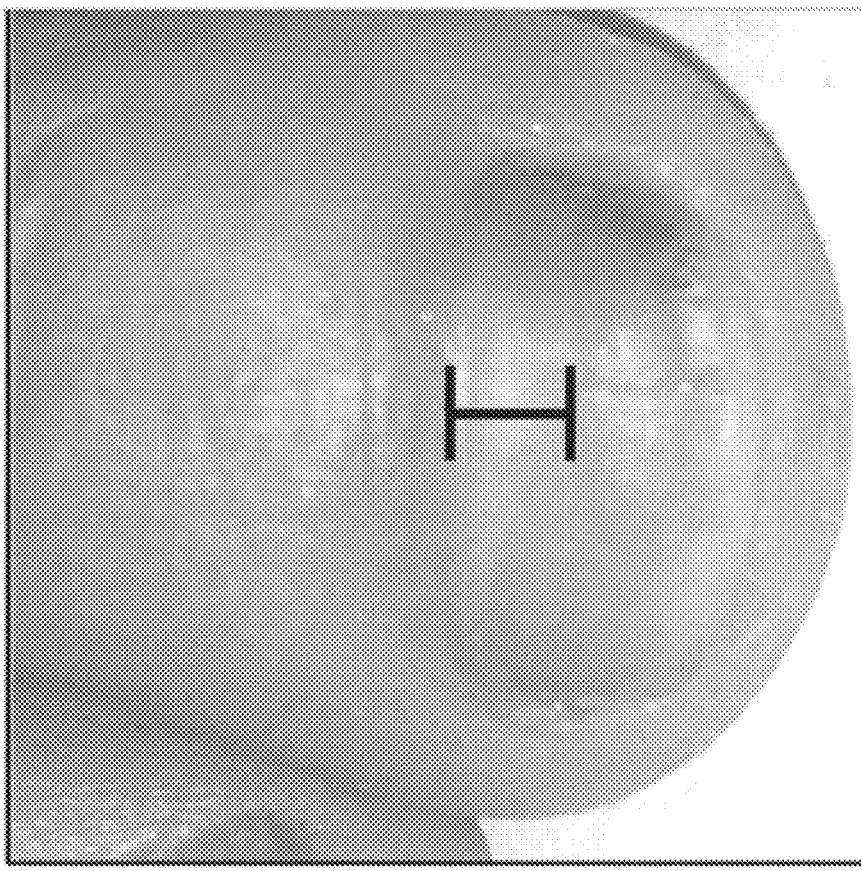
FIG. 13A Before (May 6, 2015)
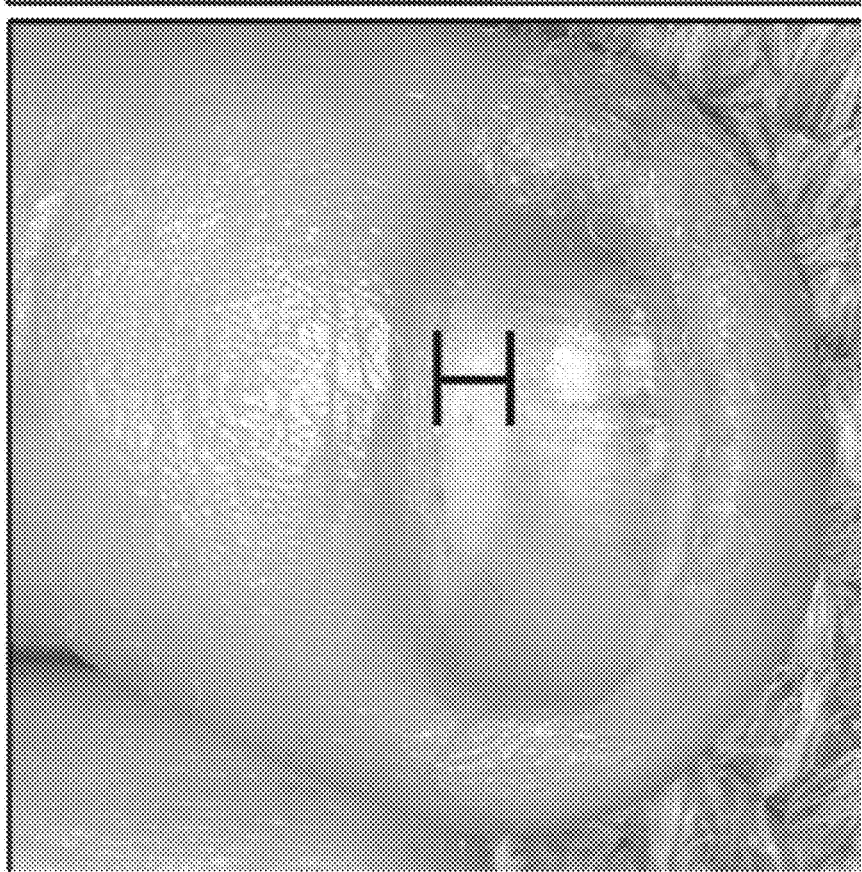
FIG. 13B After (May 26, 2015)

After (May 28, 2015)

Before (May 6, 2015)

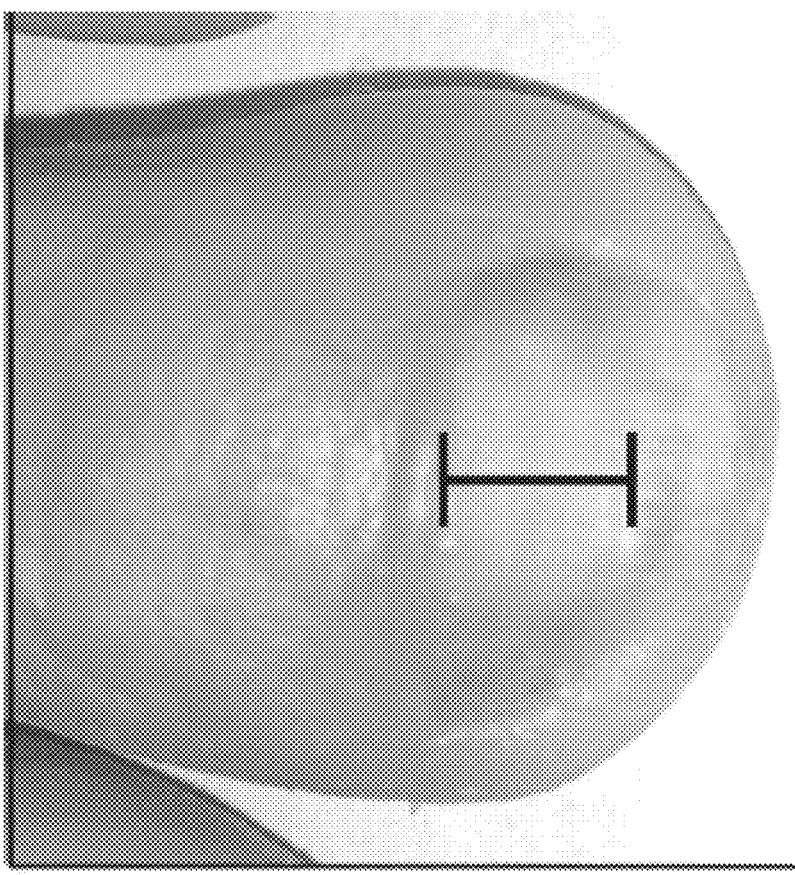
FIG. 15B After (May 26, 2015)
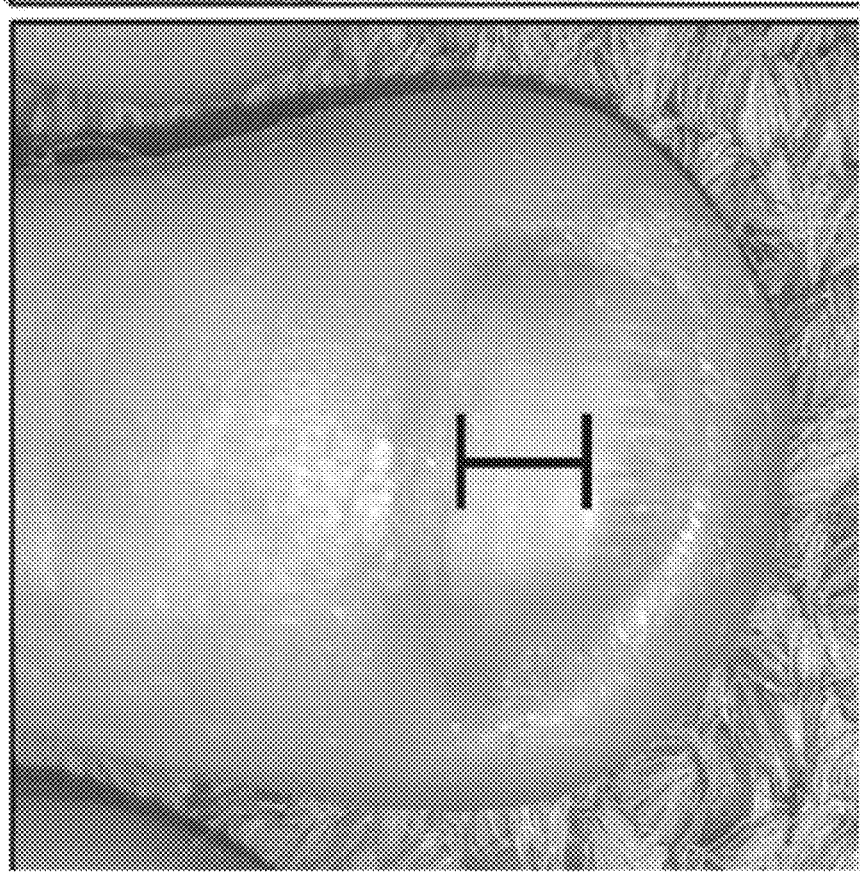
FIG. 15A Before (May 6, 2015)

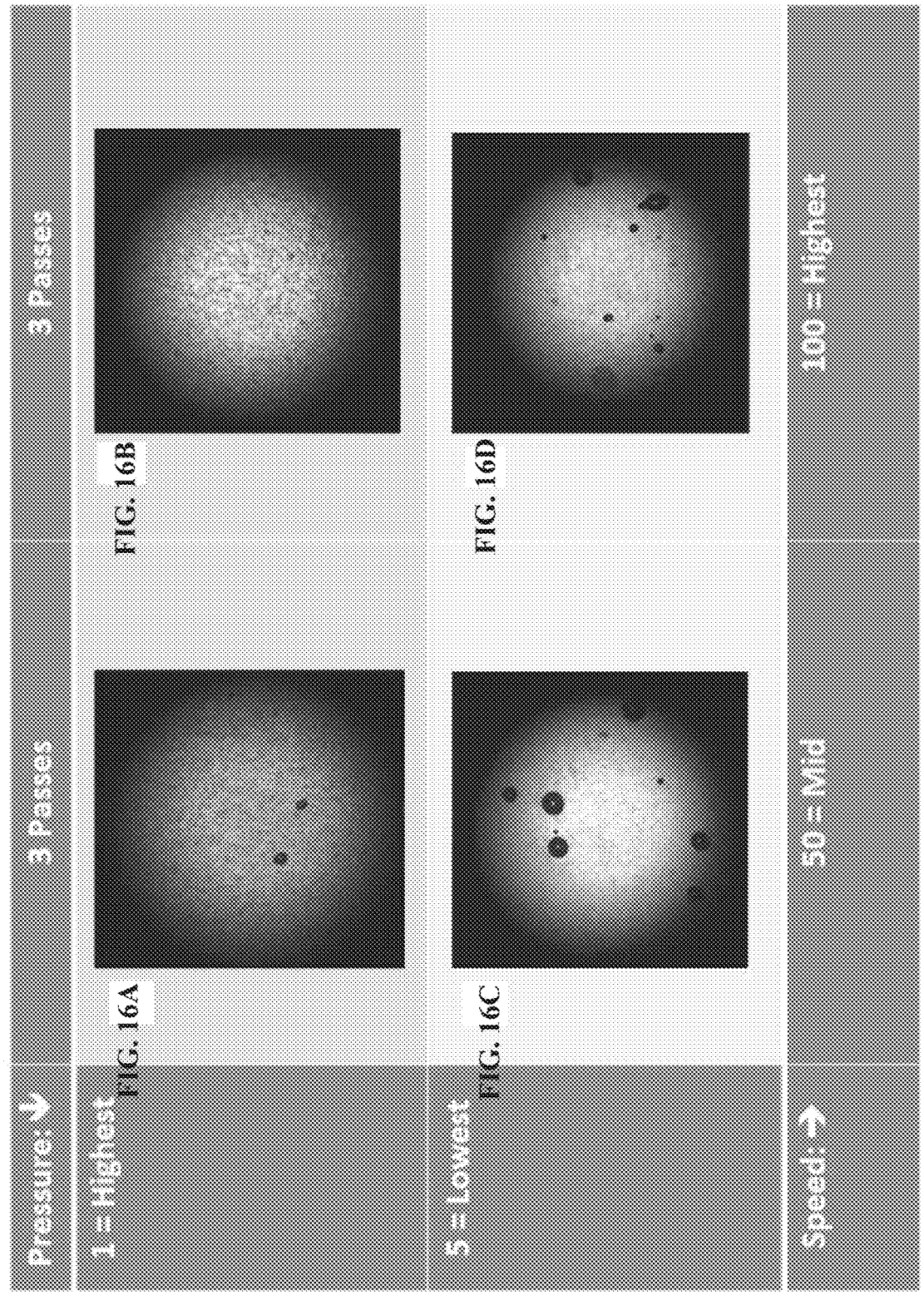

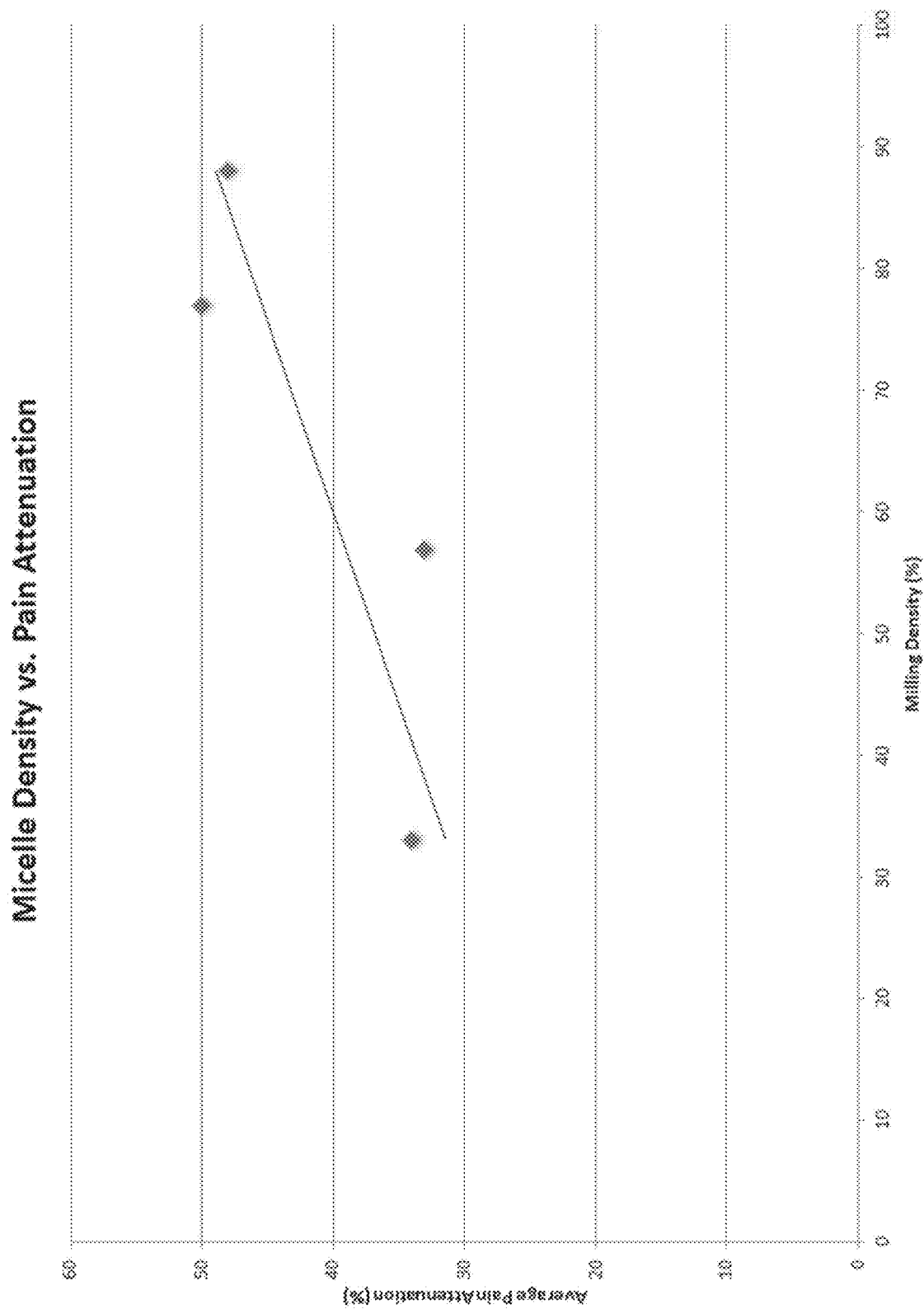

TRANSDERMAL CARRIER

CROSS-REFERENCE TO RELATED APPLICATIONS

This application is a continuation of U.S. application Ser. No. 15/994,927, filed 31 May 2018, which application is a continuation of U.S. application Ser. No. 14/757,703 filed 23 Dec. 2015, which application is a continuation-in-part of PCT application PCT/US2014/072239, having an international filing date of 23 Dec. 2014; and claims priority from U.S. Provisional Application No. 62/176,416, filed 17 Feb. 2015; U.S. Provisional Application No. 62/198,605, filed 29 Jul. 2015; U.S. Provisional Application No. 62/187,756, filed 1 Jul. 2015; U.S. Provisional Application No. 62/176,418, filed 17 Feb. 2015; U.S. Provisional Application No. 62/191,952, filed 13 Jul. 2015; U.S. Provisional Application No. 62/178,232, filed 6 Apr. 2015; U.S. Provisional Application No. 62/198,599, filed 29 Jul. 2015; U.S. Provisional Application No. 62/177,814, filed 24 Mar. 2015; U.S. Provisional Application No. 62/261,167, filed 30 Nov. 2015; U.S. Provisional Application No. 62/176,438, filed 17 Feb. 2015; U.S. Provisional Application No. 62/176,417, filed 17 Feb. 2015; U.S. Provisional Application No. 62/176,414, filed 17 Feb. 2015; U.S. Provisional Application No. 62/176,415, filed 17 Feb. 2015; U.S. Provisional Application No. 62/176,419, filed 17 Feb. 2015; U.S. Provisional Application No. 62/178,192, filed 2 Apr. 2015; U.S. Provisional Application No. 62/238,012, filed 6 Oct. 2015; and U.S. Provisional Application No. 62/178,193, filed 2 Apr. 2015. The contents of these documents are hereby incorporated by reference in their entirety.

TECHNICAL FIELD

The invention is in the field of topical treatments that effect transdermal transport of an active agent through the skin, nail or hair follicles. More particularly it concerns direct application of a penetrating formulation containing an active agent topically to a subject.

BACKGROUND ART

Various formulations have been proposed to effect transport of therapeutically active agents topically through the skin and hair follicles. For example, US2009/0053290 describes formulations for transdermal delivery of active ingredients which formulations comprise a combination of two penetrants, the first being present in amounts from about 1% to about 20% by weight (% w/w) and typified as benzyl alcohol and a second penetrant typified by a lecithin organogel present in an amount of 0.5%-20% w/w. In preferred compositions, the benzyl alcohol is present in a significantly higher amount than the lecithin organogel. In some embodiments, the second penetrant is a combination of the lecithin organogel with Pluronic®. It is suggested that the percentage of the combination of Pluronic® and lecithin organogel in the formulation be 0.5-15% w/w.

PCT publication WO2014/209910 discloses topical formulations wherein benzyl alcohol is present in about 2% w/w of the composition and lecithin organogel while permitted to be present in the range of 0.5%45% w/w is preferably present in a concentration lower than that of the benzyl alcohol. A suggested preferred composition is 2% benzyl alcohol and 0.6% lecithin organogel. This publication specifically excludes the use of poloxamers such as Pluronic®.

Other compositions that employ lecithin organogels for transdermal administration are described in Raut, S., et al., *Acta Pharm Sin* (2012) 2:8-15 and reviewed by Elnaggar, Y., S-R., et al., *J. Controlled Rel.* (2014) 180:10-24.

It has now been found, unexpectedly, that high concentrations of lecithin organogel in comparison to the concentration of benzyl alcohol (or its similars) lead to effective delivery of drugs topically to effect local or overall systemic administration and, further, that the inclusion of a nonionic detergent and polar solvent and/or a bile salt is helpful. In some embodiments, anhydrous formulations can be employed.

DISCLOSURE OF THE INVENTION

It has surprisingly been found that using the formulations and methods of the present invention, particularly effective transdermal local or systemic delivery of therapeutically active agents can be achieved. Without intending to be bound by any theory, applicants believe that the improvement is due to the enhanced ability of the formulations of the invention to permit penetration of the skin, nails or hair follicles by the active ingredient or ingredients in the formulations. Improvements have also been made in conducting the method of applying these formulations.

Thus, in one aspect, the invention is directed to a formulation for transdermal delivery of a therapeutic agent through the skin or hair follicle. The formulation comprises an active agent in an amount effective for treatment along with benzyl alcohol at 0.5-20% w/w and lecithin organogel at 25-70% w/w. Additional components, such as antioxidants, may also be included.

In some embodiments, the formulation also contains surfactant, typically, nonionic surfactant at 2-25% w/w along with a polar solvent wherein the polar solvent is present in an amount at least in molar excess of the nonionic surfactant. In these embodiments, typically, the composition comprises the above-referenced amounts of lecithin organogel and benzyl alcohol along with active ingredient with sufficient amount of a polar solution, typically an aqueous solution or polyethylene glycol solution that itself contains 10%-40% of surfactant, typically nonionic surfactant, to bring the composition to 100%.

In another embodiment, the formulation comprising active ingredient and the above-stated amounts of benzyl alcohol and lecithin organogel is essentially anhydrous and comprises bile salts and essentially no water. The bile salts are present in a percentage of 1-15% w/w in the total composition. These compositions may further contain a surfactant, which as above, is typically nonionic, which is supplied in powder form. The percentage composition of the detergent may be quite high and in the range of 20-60% w/w. In this embodiment, typically, the components of the composition—the active ingredient, the lecithin organogel, the benzyl alcohol and bile salt are "topped off" with the powdered form of the surfactant.

In some embodiments, bile salts themselves are an active agent in that the compositions are able to dissolve fat deposits due to the action of the bile salt. In these compositions, lower limit of lecithin organogel is extended from 25% w/w to 0.5% w/w as a lower limit.

In still another embodiment, in addition to active agent, lecithin organogel in the range of 25%-70% w/w in benzyl alcohol in the above-stated range of 0.5-20% of the total, nonionic detergent is mixed with the remaining ingredients and buffered with a concentrated aqueous solution to pH 9-11.

In still another embodiment, in the essentially anhydrous compositions of the invention, the formulation contains an effective amount of active ingredient, 0.5%-70% w/w lecithin organogel, 0.5%-2% w/w of benzyl alcohol or alternative alcohol, 1%-15% w/w of bile salt, and a powdered form of nonionic surfactant. This formulation may also be buffered to the range of pH 9-11.

In still another aspect, the invention is directed to a penetrant composition lacking an active agent, but containing the remaining components of the penetrant at concentrations that when mixed with the requisite amount of active agent will result in the formulations described above.

In other aspects, the invention is directed to delivery of the active agent either simply to local subdermal locations or systematically to a human or non-human animal using the formulations of the invention. The invention is also directed to the penetrant itself where its composition amounts are adjusted to take account of the contribution to the overall composition of the active ingredient.

The formulations of the invention share the above-described characteristics regardless of the nature of the active ingredient. However, the choice among penetrants fitting this description and the manner of their application may vary with the nature of what is to be administered. For example, in administering anesthetics, it is often useful to include epinephrine or other vasoconstrictor which may require adjustments in administration technique due to the instability of epinephrine at the high pH that is desirable in administering the anesthetic itself. In the case of volume enhancement using a dicarboxylic anhydride, premature hydrolysis of the anhydride must be prevented and thus either an anhydrous composition must be used or the application must be done in such a way that the anhydride does not have an opportunity to hydrolyze. That said, compositions with the above-described characteristics are applicable to a wide range of active ingredients and in a wide variety of applications.

Typically, the subject to be treated with the formulations of the invention is human, but the use of the penetrant(s) is not limited to human use. The transdermal effects are also exerted in other animals including mammals, birds and fish.

In the methods of the invention, the exact procedure for applying the formulation will depend on the nature of the active ingredient. However, as the treatment in general opens the skin to permeation, it is generally useful to essentially reseal the area of application by applying, for example, a composition comprising linoleic acid which serves this purpose.

BRIEF DESCRIPTION OF THE DRAWINGS

FIG. 1A shows the subject before treatment and FIG. 1B shows the subject 15 minutes after treatment.

FIG. 3A shows the subject prior to treatment and FIG. 3B shows the subject 15 minutes after treatment.

FIGS. 4A and 4B show the results of topical treatment with DCA to dissolve fat after 12 days. FIG. 4A shows the relevant area before and FIG. 4B shows the relevant area after treatment when 12 days has elapsed.

FIGS. 6A-6C show relative performance parameters of treated vs. control where the treated subject is supplied a formulation containing nutrient factors and metabolism balancing moieties. FIG. 6A shows the relative enhanced time a subject performing a calf flexion/heel raise exercise is able to perform the exercise before experiencing lactic acid burn. FIG. 6B shows the relative time until threshold pain is experienced. FIG. 6C shows the relative number of repetitions that can be performed in treated vs. untreated controls.

FIGS. 9A and 9B are before and after depictions respectively of hair growth in the treated area.

FIGS. 12A and 12B show enlarged views of the results in the subjects of FIGS. 11A and 11B after seven weeks of treatment.

FIG. 13A-15B are photographs of the toenails of subjects before and after treatment for onychomycosis. FIG. 13A-15A show toenails of the subjects prior to treatment and FIG. 13B-15B show the same nails after three weeks of treatment twice daily.

FIG. 16A-D are photomicrographs showing the micelle density of various formulations prepared by different milling procedures.

FIG. 17 is a comparison of micelle density versus pain attenuation using formulations of lidocaine prepared by different milling procedures.

MODES OF CARRYING OUT THE INVENTION

Figure 1A:
FIGS. 1A and 1B show the effectiveness of the formulations of the invention in removing crow's feet in a subject.

As noted above, the superior effects achieved by the formulations and methods of the present invention are attributable to an improved formulation that enhances delivery of an active agent through the skin. The carrier employs penetrants described in the above cited US2009/0053290 ('290) and WO2014/209910 ('910)—i.e., benzyl alcohol and a lecithin organogel, but at much higher ratios of lecithin organogel to benzyl alcohol than in the prior art compositions. The present carriers also may include a nonionic surfactant which is disclosed to be undesirable in the '910 publication and is described in the '290 publication as present only in very low amounts. Applicants have found that by employing very high amounts of the lecithin organogel relative to benzyl alcohol and relative to the weight of the formulation, as well as in some embodiments providing a combination of a nonionic surfactant and molar excess of a polar gelling agent, the penetration capabilities of the resulting formulation and the effective level of delivery of the active agent can be greatly enhanced. Such a result was completely unpredictable as it was believed that relatively equal amounts of the benzyl alcohol and lecithin organogel especially a somewhat higher concentration of benzyl alcohol than lecithin organogel were responsible for the level of penetration achieved by prior art formulations.

In embodiments where a bile salt is added to the combination of benzyl alcohol and lecithin organogel in lieu of topping off with an aqueous medium, micelles that would have been relatively spherical may become elongated and worm-like thus permitting superior penetration of the stratum corneum of the epidermis. The worm like formation of the micelles is particularly helpful in accommodating higher molecular weight therapeutic agents. Bile salts are facial amphiphiles and include salts of taurocholic acid, glycocholic acid, taurochenodeoxycholic acid, glycochenodeoxycholic acid, cholic acid, deoxycholic acid. Other detergents are also useful in lieu of bile salts, and include Tween® 80 and Span® 80. As noted above, where the bile salt is the active ingredient in the dissolution of fat deposits, lower concentrations of the lecithin organogel are included within the scope of the formulations.

The inclusion of these bile salts facilitates the ultradeformability of micelles which, in turn, facilitate passage of low and high molecular weight drugs and other active agents such as nucleic acids and proteins. These compositions overcome the skin penetration barrier by squeezing themselves along the intercellular sealing lipid thereby following the natural gradient across the stratum corneum. This facilitates a change in membrane composition locally and reversibly when pressed against or attracted to a narrow pore.

In some formulations of the invention, in addition to the above amounts of bile salts, benzyl alcohol, lecithin organogel and active ingredient, the formulations are "topped off" with a powdered nonionic detergent. The pH of such compositions can be determined by taking a small sample and dissolving it in water to test the appropriate pH. In many embodiments, the pH is in the range of 8.5-11 or 9-11 or 10-11.

In some formulations, formation of micelles is enhanced by milling. The level of enhancement is determined by the pressure and speed at which milling occurs as well as the number of passes through the milling machine. As the number of passes and the pressure is increased, the level of micelle formulation is enhanced as well. In general, increasing the pressure and increasing the speed of milling enhances the level of micelle density. When the ointment milling machine is a Dermamill 100 (Blaubrite) marketed by Medisca®, typical speeds include any variation between 1 to 100, where 1 is the slowest speed and 100 is the fastest speed, such as speeds of 1, 5, 10, 15, 20, 25, 30, 35, 40, 45, 50, 55, 60, 65, 70, 75, 80, 85, 90 or 100, or any speed in between. The pressure is selected from 1 to 5, where 1 is the highest pressure and 5 is the lowest pressure. The pressure used can be selected from 1, 2, 3, 4, or 5. The number of passes can also be varied, where a pass is complete when all of the product has passed through the rollers of the machine. Multiple passes, such as 2, 3, 4, 5, 6, 7, 8, 9, 10 or more passes, are contemplated in some embodiments. The speed and pressure can be varied for each pass. For example, a first pass may have a first pressure and first speed, while a second (or subsequent) pass may have a second pressure and second speed, where the second pressure is the same or different from the first pressure and the second speed is the same or different from the first speed. The desired micelle density for particular formulations can be determined empirically by varying the speed, pressure and number of passes.

Of course, alternative ointment milling machines could also be used, and comparable speeds, pressures and numbers of passes are replicated by comparison to the equivalents on the Dermamill 100. Alternatively, micelle densities can be compared microscopically to assure equivalent results to those set forth herein. In some embodiments, micelle density is at least 20% and in many embodiments 30%, 50%, 70%, 80%, or 90% and all levels within this range, as determined by the method described in Example 23 below.

The percentage of active agent in the formulation will depend upon the amount required to be delivered in order to have a useful effect on treating the disorder. In general, the active ingredient may be present in the formulation in an amount as low as 0.01% w/w up to about 50% w/w. Typical concentrations include 0.25% w/w, 1% w/w, 5% w/w, 10% w/w, 20% w/w and 30% w/w. Since the required percentage of active ingredient is highly variable depending on the active agent and depending on the frequency of administration, as well as the time allotted for administration for each application, the level of active ingredient may be varied over a wide range, and is limited only by the necessity for including in the formulation aids in penetration of the skin by the active ingredient.

The formulations of the invention may include only one active agent or a combination of active agents. In the present application, "active agent" or "active ingredient" refers to a compound or drug that is active against the factors or agents that result in the desired therapeutic or other localized systemic effect.

In general, in the present application, "a," "an," "one," and the like should be interpreted to mean one or more than one unless it is clear from the context that only a single referent is intended. Thus, "an active ingredient" may refer to one or more such active ingredients.

The formulations of the invention may be prepared in a number of ways. Typically, the components of the formulation are simply mixed together in the required amounts. However, it is also desirable in some instances to, for example, carry out dissolution of an active ingredient and then add a separate preparation containing the components aiding the delivery of the active ingredients in the form of a carrier. The concentrations of these components in the carrier, then, will be somewhat higher than the concentrations required in the final formulation. Thus, an anesthetic such as lidocaine might first be dissolved in alcohol and then added to a carrier comprising benzyl alcohol, lecithin organogel and optionally a combination of a nonionic surfactant and polar gelling agent, or of ionic detergent and a bile salt. Alternatively some subset of these components can first be mixed and then "topped off" with the remaining components either simultaneously or sequentially. The precise manner of preparing the formulation will depend on the choice of active ingredients and the percentages of the remaining components that are desirable with respect to that active ingredient.

The Nature of the Penetrant

The penetrant formulation is a multi-component mixture whereby the particular concentrations of the penetration enhancers are informed in part by the molecular mass of the proposed guest drugs to be transported. The drug delivery system enables the guest molecules to become bio-available to the target site within minutes of topical administration. The formulations permit the use of minimal concentrations of guest molecules, as little as ¹⁄₁₀₀₀th of concentrations required of alternative processes, while enabling bioactivity and positive clinical outcomes simultaneously.

The formulations comprise mixtures wherein the components interact synergistically and induce skin permeation enhancements better than that induced by the individual components. Synergies between chemicals can be exploited to design potent permeation enhancers that overcome the efficacy limitations of single enhancers. Several embodiments disclosed herein utilize three to five distinct permeation enhancers. (As used herein "detergent" and "surfactant" are synonymous.)

As noted above, the essential components of the formulations for most applications are 25%-70% w/w lecithin organogel and 0.5-20% w/w benzyl alcohol or closely related alcohol as well as supplementary components such as detergents, typically nonionic detergents, bile salts, polar solvents and the like. Each of these is further discussed below:

The lecithin organogel included in the composition is a combination of lecithin with a gelling component, which is typically amphiphilic. Suitable gelling components include, in addition to isopropyl palmitate, ethyl laurate, ethyl myristate and isopropyl myristate. Certain hydrocarbons, such as cyclopentane, cyclooctane, trans-decalin, trans-pinane, n-pentane, n-hexane, n-hexadecane may also be used. Thus, an important permeation agent is a lecithin organogel, wherein the combination resulting from lecithin and the organic solvent acts as a permeation agent. Lecithin organogels are clear, thermodynamically stable, viscoelastic, and biocompatible jelly-like phases, chiefly composed of hydrated phospholipids and appropriate organic liquid. An example of a suitable lecithin organogel is lecithin isopropyl palmitate, which is formed when isopropyl palmitate is used to dissolve lecithin. The ratio of lecithin to isopropyl palmitate may be 50:50. Illustrated below in the Examples is a formulation containing soy lecithin in combination with isopropyl palmitate; however, other lecithins could also be used such as egg lecithin or synthetic lecithins. Various esters of long chain fatty acids may also be included. Methods for making such lecithin organogels are well known in the art. In most embodiments, the lecithin organogel is present in the final formulation in the range of 25-70% w/w and at intermediate percentages such as 30% w/w, 40% w/w, 50% w/w, 60% w/w, etc. In those compositions used to dissolve fat deposits, to alleviate pain from fat removal or in anhydrous compositions, the concentration of lecithin organogel may be as low as 0.5% w/w, 1% w/w, 5% w/w, 10% w/w or 20% w/w. Any suitable percentage within the specified ranges is acceptable as long as it is compatible with the active agent and the remaining components of the composition.

Lecithin organogels may be in the form of vesicles, microemulsions and micellar systems. In the form of self-assembled structures, such as vesicles or micelles, they can fuse with the lipid bilayers of the stratum corneum, thereby enhancing partitioning of encapsulated drug, as well as a disruption of the ordered bilayers structure. An example of a phospholipid-based permeation enhancement agent comprises a micro-emulsion-based organic gel defined as a semi-solid formation having an external solvent phase immobilized within the spaces available of a three-dimensional networked structure. This micro-emulsion-based organic gel in liquid phase is characterized by 1,2-diacyl-sn-glycero-3-phosphatidyl choline, and an organic solvent, which is at least one of: ethyl laureate, ethyl myristate, isopropyl myristate, isopropyl palmitate; cyclopentane, cyclooctane, trans-decalin, trans-pinane, n-pentane, n-hexane, n-hexadecane, and tripropylamine.

The lecithin organogels are formulated with an additional component to assist in the formation of micelles or vascular structures. In one approach, the organogels are formulated with a polar component such as water, glycerol, ethyleneglycol or formamide, in particular with water. In general, a nonionic detergent such as a poloxamer in aqueous solution is used to top off. Alternatively, an anhydrous composition may be obtained by using, instead of a polar component, a material such as a bile salt. When formulated with bile salts, the micellular nature of the composition is altered so that rather than a more or less spherical vesicular form, the vesicles become wormlike and are able to accommodate larger guest molecules, as well as penetrate the epidermis more effectively. Suitable bile salts include salts of deoxycholic acid, taurocholic acid, glycocholic acid, taurochenodeoxycholic acid, glycochenodeoxycholic acid, cholic acid and the like. Certain detergents, such as Tween® 80 or Span® 80 may be used as alternatives. The percentage of these components in the anhydrous forms of the composition is in the range of 1% w/w-15% w/w. In some embodiments, the range of bile salt content is 2%-6% w/w or 1%-3.5% w/w. In these essentially anhydrous forms, powdered or micronized nonionic detergent is used to top off, typically in amounts of 20%-60% w/w. In one approach to determine the amount of bile salt, the % is calculated by dividing the % w/w of lecithin by 10.

An additional required component in the formulations of the invention is an alcohol. Benzyl alcohol is illustrated in the Examples, but in some formulations other alcohols could be included, in particular derivatives of benzyl alcohol which contain substituents on the benzene ring, such as halo, alkyl and the like. The weight percentage of benzyl or other related alcohol in the final composition is 0.5-20% w/w, and again, intervening percentages such as 1% w/w, 2% w/w, 5% w/w, 7% w/w, 10% w/w, and other intermediate weight percentages are included. Due to the aromatic group present in a permeation enhancement formulation such as benzyl alcohol, the molecule has a polar end (the alcohol end) and a non-polar end (the benzene end). This enables the agent to dissolve a wider variety of drugs and agents. The alcohol concentration is substantially lower than the concentration of the lecithin organogel in the composition.

By formulating active ingredients in the presence of at least a combination of a lecithin organogel and a suitable alcohol, especially benzyl alcohol where the lecithin organogel is in a ratio of concentration at least 10-fold that of the alcohol on a weight basis, superior results are achieved as illustrated in the examples below.

In some embodiments, as noted above, the performance of the formulations is further improved by including a nonionic detergent and polar gelling agent or including bile salts and a powdered surfactant. In both aqueous and anhydrous forms of the composition, detergents, typically nonionic detergents are added. In general, the nonionic detergent should be present in an amount of at least 2% w/w to 60% w/w. Typically, in the compositions wherein the formulation is topped off with a polar or aqueous solution containing detergent, the amount of detergent is relatively low—e.g., 2%-25% w/w, or 5-15% w/w or 7-12% w/w. However, in compositions comprising bile salts that are essentially anhydrous and are topped-off by powdered detergent, relatively higher percentages are usually used—e.g., 20%-60% w/w. The boundaries are not rigid but the above description indicates the general range.

In some embodiments, the nonionic detergent provides suitable handling properties whereby the formulations are gel-like or creams at room temperature. To exert this effect, the detergent, typically a poloxamer, is present at a level of at least 9% w/w, preferably at least 12% w/w in polar formulations. In the anhydrous forms of the compositions, the detergent is added in powdered or micronized form to bring the composition to 100% and higher amounts are used. In compositions with polar constituents, rather than bile salts, the nonionic detergent is added as a solution to bring the composition to 100%. If smaller amounts of detergent solutions are needed due to high levels of the remaining components, more concentrated solutions of the nonionic detergent are employed. Thus, for example, the percent detergent in the solution may be 10% to 40% or 20% or 30% and intermediate values depending on the percentages of the other components.

Suitable nonionic detergents include poloxamers such as Pluronic® and any other surfactant characterized by a combination of hydrophilic and hydrophobic moieties. Poloxamers are triblock copolymers of a central hydrophobic chain of polyoxypropylene flanked by two hydrophilic chains of polyethyleneoxide. Other nonionic surfactants include long chain alcohols and copolymers of hydrophilic and hydrophobic monomers where blocks of hydrophilic and hydrophobic portions are used.

Other examples of surfactants include polyoxyethylated castor oil derivatives such as HCO-60 surfactant sold by the HallStar Company; nonoxynol; octoxynol; phenylsulfonate; poloxamers such as those sold by BASF as Pluronic® F68, Pluronic® F127, and Pluronic® L62; polyoleates; Rewopal® HV10, sodium laurate, sodium lauryl sulfate (sodium dodecyl sulfate); sodium oleate; sorbitan dilaurate; sorbitan dioleate; sorbitan monolaurate such as Span® 20 sold by Sigma-Aldrich; sorbitan monooleates; sorbitan trilaurate; sorbitan trioleate; sorbitan monopalmitate such as Span® 40 sold by Sigma-Aldrich; sorbitan stearate such as Span® 85 sold by Sigma-Aldrich; polyethylene glycol nonylphenyl ether such as Synperonic® NP sold by Sigma-Aldrich; p-(1,1,3,3-tetramethylbutyl)-phenyl ether sold as Triton™ X-100 sold by Sigma-Aldrich; and polysorbates such as polyoxyethylene (20) sorbitan monolaurate sold as Tween® 20, polysorbate 40 (polyoxyethylene (20) sorbitan monopalmitate) sold as Tween® 40, polysorbate 60 (polyoxyethylene (20) sorbitan monostearate) sold as Tween® 60, polysorbate 80 (polyoxyethylene (20) sorbitan monooleate) sold as Tween® 80, and polyoxyethylenesorbitan trioleate sold as Tween® 85 by Sigma-Aldrich. The weight percentage range of nonionic surfactant is in the range of 3% w/w-15% w/w, and again includes intermediate percentages such as 5% w/w, 7% w/w, 10% w/w, 12% w/w, and the like.

In the presence of a polar gelling agent, such as water, glycerol, ethyleneglycol or formamide, a micellular structure is also often achieved. Typically, the polar agent is in molar excess of the nonionic detergent. The inclusion of the nonionic detergent/polar gelling agent combination results in a more viscous and cream-like or gel-like formulation which is suitable for application directly to the skin. This is typical of the aqueous forms of the composition. As noted above, it may be rather than a polar gelling agent, a bile salt can be used. In this case, the detergent is added in solid, powdered form.

In some instances, the formation of micelles is improved by a milling procedure. In general, more passes and higher pressures favor a higher percentage of micelles.

In some embodiments other additives are included such as a gelling agent, a dispersing agent and a preservative. An example of a suitable gelling agent is hydroxypropylcellulose, which is generally available in grades from viscosities of from about 5 cps to about 25,000 cps such as about 1500 cps. All viscosity measurements are assumed to be made at room temperature unless otherwise stated. The concentration of hydroxypropylcellulose may range from about 1% w/w to about 2% w/w of the composition. Other gelling agents are known in the art and can be used in place of, or in addition to, hydroxypropylcellulose. An example of a suitable dispersing agent is glycerin. Glycerin is typically included at a concentration from about 5% w/w to about 25% w/w of the composition. A preservative may be included at a concentration effective to inhibit microbial growth, ultraviolet light and/or oxygen-induced breakdown of composition components, and the like. When a preservative is included, it may range in concentration from about 0.01% w/w to about 1.5% w/w of the composition.

Typical components that may also be included in the formulations are fatty acids, terpenes, lipids, and cationic and anionic detergents.

Other solvents and related compounds that may be used in some embodiments include acetamide and derivatives, acetone, n-alkanes (chain length between 7 and 16), alkanols, diols, short-chain fatty acids, cyclohexyl-1,1-dimethylethanol, dimethyl acetamide, dimethyl formamide, ethanol, ethanol/d-limonene combination, 2-ethyl-1,3-hexanediol, ethoxydiglycol (Transcutol® by Gattefossé, Lyon, France), glycerol, glycols, lauryl chloride, limonene N-methylformamide, 2-phenylethanol, 3-phenyl-1-propanol, 3-phenyl-2-propen-1-ol, polyethylene glycol, polyoxyethylene sorbitan monoesters, polypropylene glycol 425, primary alcohols (tridecanol), 1,2-propane diol, butanediol, $C_3$-$C_6$ triols or their mixtures and a polar lipid compound selected from $C_{16}$ or $C_{18}$ monounsaturated alcohol, $C_{16}$ or $C_{18}$ branched saturated alcohol and their mixtures, propylene glycol, sorbitan monolaurate sold as Span® 20 sold by Sigma-Aldrich, squalene, triacetin, trichloroethanol, trifluoroethanol, trimethylene glycol and xylene.

Fatty alcohols, fatty acids, fatty esters, are bilayer fluidizers that may be used in some embodiments. Examples of suitable fatty alcohols include aliphatic alcohols, decanol, lauryl alcohol (dodecanol), unolenyl alcohol, nerolidol, 1-nonanol, n-octanol, and oleyl alcohol. Examples of suitable fatty acid esters include butyl acetate, cetyl lactate, decyl N,N-dimethylamino acetate, decyl N,N-dimethylamino isopropionate, diethyleneglycol oleate, diethyl sebacate, diethyl succinate, diisopropyl sebacate, dodecyl N,N-dimethyamino acetate, dodecyl (N,N-dimethylamino)-butyrate, dodecyl N,N-dimethylamino isopropionate, dodecyl 2-(dimethyamino) propionate, E0-5-oleyl ether, ethyl acetate, ethylaceto acetate, ethyl propionate, glycerol monoethers, glycerol monolaurate, glycerol monooleate, glycerol monolinoleate, isopropyl isostearate, isopropyl linoleate, isopropyl myristate, isopropyl myristate/fatty acid monoglyceride combination, isopropyl palmitate, methyl acetate, methyl caprate, methyl laurate, methyl propionate, methyl valerate, 1-monocaproyl glycerol, monoglycerides (medium chain length), nicotinic esters (benzyl), octyl acetate, octyl N,N-dimethylamino acetate, oleyl oleate, n-pentyl N-acetylprolinate, propylene glycol monolaurate, sorbitan dilaurate, sorbitan dioleate, sorbitan monolaurate, sorbitan monolaurate, sorbitan trilaurate, sorbitan trioleate, sucrose coconut fatty ester mixtures, sucrose monolaurate, sucrose monooleate, tetradecyl N,N-dimethylamino acetate. Examples of suitable fatty acid include alkanoic acids, caprid acid, diacid, ethyloctadecanoic acid, hexanoic acid, lactic acid, lauric acid, linoelaidic acid, linoleic acid, linolenic acid, neodecanoic acid, oleic acid, palmitic acid, pelargonic acid, propionic acid, and vaccenic acid. Examples of suitable fatty alcohol ethers include α-monoglyceryl ether, E0-2-oleyl ether, E0-5-oleyl ether, E0-10-oleyl ether, ether derivatives of polyglycerols and alcohols, and (1-O-dodecyl-3-O-methyl-2-0-(2',3'-dihydroxypropyl) glycerol).

Examples of completing agents that may be used in some embodiments include β- and γ-cyclodextrin complexes, hydroxypropyl methylcellulose (such as Carbopol® 934), liposomes, naphthalene diamide diimide, and naphthalene diester diimide.

One or more anti-oxidants may be included, such as vitamin C, vitamin E, proanthocyanidin and α-lipoic acid typically in concentrations of 0.1%-2.5% w/w.

In some applications, it is desirable to adjust the pH of the formulation to assist in permeation or to adjust the nature of the active agent and/or of the target compounds in the subject. In some instances, the pH is adjusted to a level of pH 9-11 or 10-11 which can be done by providing appropriate buffers or simply adjusting the pH with base.

In some applications, in particular when the active ingredient includes an anesthetic, epinephrine or an alternate vasoconstrictor, such as phenylephrine or epinephrine sulfate may be included in the formulation if a stabilizing agent is present. Otherwise, the epinephrine should be administered in tandem since epinephrine is not stable at these pH's.

General Methods of Application

The application method is determined by the nature of the treatment but is, perhaps, less critical than the nature of the formulation itself. If the application is to a skin area, it may be helpful in some instances to prepare the skin by cleansing or exfoliation. In some instances, it is helpful to adjust the pH of the skin area prior to application of the formulation itself. The application of the formulation may be by simple massaging onto the skin or by use of devices such as syringes or pumps. Patches could also be used. In some cases, it is helpful to cover the area of application to prevent evaporation or loss of the formulation. It is especially helpful in the case of application to fingernails or toenails to do this.

Where the application area is essentially skin as opposed to nails or hair follicles, it is helpful to seal-off the area of application subsequent to supplying the formulation and allowing the penetration to occur so as to restore the skin barrier. A convenient way to do this is to apply a composition comprising linoleic acid which effectively closes the entrance pathways that were provided by the penetrants of the invention. This application, too, is done by straightforward smearing onto the skin area or can be applied more precisely in measured amounts.

Particular techniques for application in connection with specific types of active ingredients are described in more detail below.

Active Ingredients and Applications

A wide variety of active ingredients may be used in the compositions, including anesthetics, fat removal compounds, nutrients, nonsteroidal anti-inflammatory drugs (NSAIDs) agents for the treatment of migraine, hair growth modulators, antifungal agents, anti-viral agents, vaccine components, tissue volume enhancing compounds, anti-cellulite therapeutics, wound healing compounds, compounds useful to effect smoking cessation, agents for prevention of collagen shrinkage, wrinkle relief compounds such as Botox®, skin-lightening compounds, compounds for relief of bruising, cannabinoids including cannabidiols for the treatment of epilepsy, compounds for adipolysis, compounds for the treatment of hyperhidrosis, acne therapeutics, pigments for skin coloration for medical or cosmetic tattooing, sunscreen compounds, hormones, insulin, corn/callous removers, wart removers, and generally any therapeutic or prophylactic agent for which transdermal delivery is desired. As noted above, the delivery may simply effect transport across the skin or nails or hair follicles into a localized subdermal location, such as treatment of nail fungus or modulation of hair growth, or may effect systemic delivery such as is desirable in some instances where vaccines are used. A more detailed description of the formulations in respect of these active ingredients follows:

In addition to the compositions and formulations of the invention per se, the methods may employ a subsequent treatment with linoleic acid. As transdermal treatments generally open up the skin barrier, which is, indeed, their purpose, it is useful to seal the area of application after the treatment is finished. Thus, treatment with the formulation may be followed by treating the skin area with a composition comprising linoleic acid to seal off the area of application. The application of linoleic acid is applicable to any transdermal procedure that results in impairing the ability of the skin to act as a protective layer. Indeed, most transdermal treatments have this effect as their function is to allow active ingredients to pass through the epidermis to the dermis at least, and, if systemic administration is achieved, through the dermis itself.

Anesthetics

For administration of anesthetics, typical active ingredients include a local anesthetic agent or combination of local anesthetic agents. The local anesthetic agent may be one or more of the following: benzocaine, lidocaine, tetracaine, bupivacaine, cocaine, etidocaine, mepivacaine, pramoxine, prilocaine, procaine, chloroprocaine, oxyprocaine, proparacaine, ropivacaine, dyclonine, dibucaine, propoxycaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof. Combinations of anesthetic agents may also be used. The anesthetic agent(s) are included in the composition in effective amount(s). Depending on the anesthetic(s) the amounts of anesthetic or combination is typically in the range of 1% w/w to 50% w/w. The compositions of the invention provide rapid, penetrating relief that is long lasting. The pain to be treated can be either traumatic pain and/or inflammatory pain.

In one embodiment, the anesthetic is administered to relieve the pain associated with invasive fat deposit removal. Specific removal of fat deposits has been attractive for both health and cosmetic reasons. Among the methods employed are liposuction and injection of a cytolytic agent for fat such as deoxycholic acid (DCA). For example, a series of patents issued or licensed to Kythera Biopharmaceuticals is directed to methods and compositions for non-surgical removal of localized fat that involves injecting compositions containing DCA or a salt thereof. Representative issued patents are directed to formulation (U.S. Pat. No. 8,367,649); method-of-use (U.S. Pat. Nos. 8,846,066; 7,622,130; 7,754,230; 8,298,556); and synthetic DCA (U.S. Pat. No. 7,902,387).

In this aspect of the invention, conventional invasive fat removal techniques are employed along with administering a pain relieving effective agent—typically lidocaine or related anesthetics transdermally. In this aspect of the invention, the pain relieving transdermal composition is applied to the area experiencing pain immediately before, during or immediately after the invasive fat-removal procedure. Use of certain forms of the penetrants to provide transdermal administration of anesthetics was described in the above-referenced US2009/0053290 incorporated herein by reference. However, preferred compositions employ higher concentrations of the lecithin organogel, or anhydrous forms.

Additional active ingredient(s) may be included in the compositions. For example, hydrocortisone or hydrocortisone acetate may be included in an amount ranging from 0.25% w/w to about 0.5% w/w. Menthol, phenol, and terpenoids, e.g., camphor, can be incorporated for cooling pain relief. For example, menthol may be included in an amount ranging from about 0.1% w/w to about 1.0% w/w. The active ingredient may itself be an alternative such as hydrocortisone and/or menthol instead of a local anesthetic agent.

The compositions containing anesthetics are useful for temporary relief of pain and itching associated with minor burns, cuts, scrapes, skin irritations, inflammation and rashes due to soaps, detergents or cosmetics, or, as noted above, pain associated with removal of fat deposits.

In any of the anesthetic compositions, whether anhydrous or not, epinephrine can also be administered and may be helpful. Epinephrine is stable at pH of 2.5-5, and since the compositions for transdermal administration of anesthetic are preferably at a higher pH—i.e., pH 10-11, it may be desirable to administer the epinephrine in tandem with the transdermal anesthetic. Alternatively, treatment of the epinephrine with a chelator, such as the iron chelator Desferal® may stabilize the epinephrine sufficiently to include it in the transdermal composition.

The benefits of high pH include higher penetration capability and adjustment of the active form of the fat dissolving compound when the anesthetic is used in conjugation therewith. For example, the pKa of the deoxycholic acid is 6.58 and the pH of fat is neutral. When deoxycholic acid (DCA) is injected without buffering, it is approximately an equilibrium between the protonated and unprotonated forms. Utilizing formulations with high pH buffering shifts the balance significantly to unprotonated form making the DCA more water soluble and more likely to emulsify fats.

All of the above embodiments achieve several advantages over the prior art. Numbing is achieved very rapidly and is long lasting. For example, numbing may be achieved in about five minutes and the area where the composition is applied may remain numb for about 90 minutes. The numbing may reach a depth of about 25 mm.

The compositions disclosed herein may be delivered by a pump. In one embodiment, the pump is configured to deliver about 0.15 ml per stroke of the pump as a single dose. Delivering the composition by a pump allows the amount of the active ingredient needed to be easily calculated. For example, if the composition includes lidocaine in an amount of about 4% w/w of the composition and about 0.05 ml of lidocaine needs to be delivered to an area that is about 1 cm$^2$ then a pump that delivers 0.15 ml is used must be pumped eight times to deliver 1.2 ml/cm$^2$ of the composition to provide.

One illustrative embodiment of the composition comprises: lidocaine in an amount up to about 5.0% w/w; hydrocortisone in an amount of about 0.5% w/w; menthol in an amount of about 1.25% w/w; benzyl alcohol in an amount ranging from about 0.5% to about 10% w/w or about 2.0% w/w; lecithin organogel in an amount that is about 30% to about 60% w/w or 45% to about 55% w/w; and a nonionic surfactant in an aqueous solution, in an amount that is the remainder of the composition.

In another embodiment of the composition comprises: lidocaine in an amount of about 4.0% w/w; menthol in an amount of about 1% w/w; benzyl alcohol in an amount ranging from about 0.5% to about 10% w/w or about 0.9% w/w; lecithin organogel in an amount that is about 30% to about 60% w/w or 45% to about 55% w/w; or about 30% w/w and topped up with 30% Pluronic in aqueous solution and brought to pH 10.

In another embodiment of the composition comprises: benzocaine in an amount of about 20.0% w/w; menthol in an amount of about 1% w/w; benzyl alcohol in an amount ranging from about 0.5% to about 10% w/w or about 0.9% w/w; lecithin organogel in an amount that is about 30% to about 60% w/w or 45% to about 55% w/w; or about 30% w/w and topped up with 30% Pluronic® in aqueous solution and brought to pH 10.

In another exemplary embodiment, the composition comprises: benzocaine in an amount up to about 5.0% w/w; hydrocortisone in an amount of about 0.5% w/w; menthol in an amount of about 1.25% w/w; benzyl alcohol in an amount ranging from about 0.5% to about 10% w/w; lecithin in an organic solvent in an amount that is about 40% to about 60%; a nonionic surfactant in an aqueous solution, in an amount that is the remainder of the composition.

In another embodiment, the composition comprises: lidocaine in an amount of about 5.0% w/w; menthol in an amount of about 1.25% w/w; benzyl alcohol in an amount of about 2.0% w/w; soy lecithin in isopropyl palmitate in an amount ranging from about 45% to about 55% w/w; poloxamer in an aqueous solution in an amount (that is the remainder of the composition, and wherein the poloxamer is added to an intermediate mixture of the other constituents and subjected to mechanical shear force.

As noted above, the inclusion of epinephrine (epi) in the treatment is useful in many cases, and the exemplary embodiments above may be supplemented by application of, for example, a composition comprising epinephrine at 0.01% at pH 5. This can be done by applying the formulations sequentially or in layers.

Additional exemplary compositions include benzocaine+ lidocaine+tetracaine (BLT) wherein the benzocaine is contained at 20% w/w, lidocaine at 6% w/w and tetracaine at 4% w/w (BLT 20/6/4). The formulation also contains 0.9% or 2% w/w of benzyl alcohol and 30% w/w lecithin isopropyl palmitate topped up with 30% Pluronic® in aqueous solution, and is brought to pH 10. This can be administered in tandem with an epinephrine formulation containing epi at 0.01% w/w, benzyl alcohol at 0.9% or 2% w/w, lecithin isopropyl palmitate at 30% w/w also topped up with 30% Pluronic® in aqueous solution and brought to pH 5. The administration is typically sequential, for example, administering the BLT composition first for 15 min. and the epinephrine composition second for 15 min. or similar amounts of time.

In another exemplary embodiment, the above described formulation of BLT 20/6/4 in benzyl alcohol at 2% w/w and lecithin isopropyl palmitate at 30% w/w and is topped up with 30% Pluronic® in aqueous solution supplemented with epinephrine at 0.01% w/w preincubated with and/or in the presence of Desferal®, an iron chelator at 0.1% w/w, and the entire composition is brought to pH 10. This can be applied alone for periods of 10, 15, 20 or 25 minutes residence time on the skin.

In still another exemplary composition, the formulation containing the anesthetic comprises lidocaine at 5% w/w and benzocaine at 20% w/w along with benzyl alcohol at either 0.9% or 2% w/w, lecithin isopropyl palmitate at 30% w/w brought to total with 30% w/w Pluronic® in aqueous solution and pH 10 followed by the above described formulation of epinephrine at 0.01% w/w at pH 5.

In anhydrous forms of the compositions, similar penetrants and active ingredients in similar amounts are employed, but rather than topping up to 100% with nonionic detergent in aqueous or other polar solution, the compositions are instead topped up with micronized or other powdered forms of nonionic detergents in the presence of bile salts. Essentially, the syrupy composition which results from the mixture of the alcohol and organogel along with active ingredient can be blended with a solid composition comprising the bile salt and nonionic detergent. In exemplary compositions, the bile salt is a salt of deoxycholic acid and the nonionic detergent is Pluronic® or other poloxamer (which is a copolymer of polyethylene glycol and N-polypropylene oxide). In exemplary compositions, for example, the active ingredient is a combination of benzocaine, lidocaine and tetracaine, the composition contains benzyl alcohol and lecithin isopropyl palmitate and is topped off with Pluronic® in micronized form and a salt of deoxycholic acid. In other exemplary compositions the deoxycholic acid salt is replaced by salts of, for example, taurocholic acid or cholic acid.

In an exemplary embodiment, the BLT 20/6/4 combination in benzyl alcohol at 0.9% w/w and lecithin isopropyl palmitate at 30% w/w is supplemented with epinephrine at 0.01% w/w and Desferal® at 0.1% w/w and with deoxycholic acid at 1.5% w/w and Pluronic® in powdered form to bring to the total amount, adjusted to pH 10. (As this is anhydrous, the pH is measured by adding water to the composition before measurement.) In some embodiments, although epinephrine is already included in the composition, the above described formulation comprising epinephrine at 0.01% w/w and the remaining components brought to pH 5 is administered separately.

In summary, the formulations of the invention are suitable for administering local anesthetics for general relief of pain and in particular are useful in alleviating the pain associated with localized fat removal.

Volume Enhancement

In another embodiment of the present invention, enhancement of tissue volume and quality uses as the active ingredient an acylating agent. Typically, the acylating agent is an anhydride of a dicarboxylic acid. The acylation of protein thus provides a negative charge to the protein by virtue of liberating the carboxyl group not bound to the protein. Typical suitable anhydrides include maleic anhydride, succinic anhydride, glutaric anhydride, citraconic anhydride, methylsuccinic anhydride, itaconic anhydride, methylglutaric anhydride, phthalic anhydride and the like. Any dicarboxylic anhydride is suitable. Preferred are succinic anhydride and glutaric anhydride. The use of dicarboxylic acyl chlorides is theoretically possible, but these tend to be relatively abrasive, and the use of anhydrides is preferred.

The acylating agent useful in enhancing tissue volume can be delivered in three alternative approaches. In first and second approaches, either the acylating agent is supplied in powdered form and applied to the skin area covering the tissue to be treated and expanded and this is immediately followed by treating the skin area with a penetrant that causes the acylating agent to be transported through the epidermis and stratum corneum into the tissue or the penetrant is mixed with the powdered acylating agent immediately before applying the mixture to the skin. The penetrant in this case may, but need not, include a polar medium such as water. These treatments may be preceded by pretreating the skin area with a buffer to neutralize the amino groups on the proteins to be acylated.

Alternatively, in the third approach, the acylating agent can be supplied directly as a formulation in an essentially nonaqueous medium so that the acylating agent is not deactivated prior to contacting the desired protein. In this case, also, the skin area may be pretreated with buffer to neutralize the amino groups on the protein.

In all cases, the treatment with acylating agent may be followed by treating the skin area with a composition comprising linoleic acid to seal off the area of application. The application of linoleic acid is actually applicable to any transdermal procedure that results in impairing the ability of the skin to act as a protective layer. Indeed, most transdermal treatments have this effect as their function is to allow active ingredients to pass through the epidermis to the dermis at least, and, if systemic administration is achieved, through the dermis itself.

Because the acylating agents of the invention are anhydrides, prolonged contact with formulations that have an aqueous or polar component would inactivate the acylating agent by hydrolysis. Therefore, either an essentially anhydrous composition should be used as a penetrant which would permit inclusion of the acylating agent in the formulation to be administered or the acylating agent is mixed with the composition containing the penetrants immediately prior to application to the skin. In still another alternative, the acylating agent may be applied to the skin in dry form and the penetrating composition added immediately thereafter. These last two approaches are applicable either to the compositions of penetrants that are polar in nature or to those that are essentially anhydrous in nature. However, if the penetration compositions are polar or aqueous in nature, use of these latter two approaches is essentially mandated.

However the acylating agents are applied and allowed to penetrate, the skin may be pretreated by cleansing and exfoliation and, preferably pre-buffered to appropriately pH 8.5-11, preferably 10-11. The formulation of the invention is then applied using one of the three methods set forth above as appropriate. The formulation is left in contact with the skin for 10-40 minutes or any appropriate time, preferably 25-30 minutes. Optionally, then, the treatment may be concluded by treating the affected area by a composition comprising linoleic acid. The linoleic acid is applied in an aqueous or nonaqueous solution at a concentration of 25-95% w/w. In some cases, the linoleic acid can be applied as an extract of a plant that contains it. The application of linoleic acid to rebuild the stratum corneum barrier can be achieved, therefore, using extracts of sunflower seeds, kukui nut oil, and the like.

A particular sequence that illustrates the method of the invention is as follows:

(i) Local exfoliation is performed to enhance penetration. This can be done by tape stripping, mechanical abrasives, chemical exfoliation and the like. While by no means required, it is not excluded to employ penetration enhancement such as micro-needling, ultrasonic energy, iontophoresis, electroporation and the like.

(ii) The penetrant formulation alone is applied to the target site buffered to about pH 8.5-11.

(iii) After a 15 min. delay, it is wiped off.

(iv) The penetrant formulation combined with glutaric anhydride is applied at the target site, buffered to about pH 8.5-11.

(v) After a 15 min. delay, this is wiped off.

The previous illustrative procedure is merely illustrative and, as noted above, there are several ways that the penetrant composition containing the acylating agent can be administered—the composition itself may be anhydrous and/or the time delay between contact of the acylating agent with the penetrating composition is sufficiently short that even water-containing penetrants are useable.

In the final formulation, the percentage of acylating agent in the formulation will depend upon the amount required to be delivered in order to have a useful effect in enhancing tissue volume. In general, the active ingredient may be present in the formulation in an amount as low as 0.25% w/w up to about 50% w/w. Typical concentrations include 0.25% w/w, 1% w/w, 5% w/w, 10% w/w, 20% w/w and 30% w/w. Since the required percentage of acylating agent is variable depending on the choice of such agent and depending on the frequency of administration, as well as the time allotted for administration for each application, the level of active ingredient may be varied over a wide range, and is limited only by the necessity for including in the formulation aids in penetration of the skin by the active ingredient.

In addition to, or in lieu of, the acylating agent as an active ingredient, inhibitors of hyaluronidase and/or enhancers of HA synthase may be included as active ingredients. Known enhancers of HA synthase are the retinoids such as retinol, retinaldehyde and retinoic acid. Known inhibitors of hyaluronidase include flavonoids and other polyphenols, alkaloids, terpenoids, and anti-inflammatory drugs. Flavonoids include anthocyanins, flavan-4-ols, flavones and flavanols as well as condensed tannins or proanthocyanidins. These include, for example, resveratrol which is a recently publicized component of red wine.

The balance of HA synthase and hyaluronidase is necessary to restore the balance which provides sufficient moisture in the dermal water reservoir which allows water to escape through the epidermis when skin dries, as for example, through aging or solar exposure. In addition to the balancing of the concentration of HA, providing a protective layer of linoleic acid also prevents unwanted loss of water from the dermal reservoir.

Additional active ingredient(s) may be included in the composition. For example, hydrocortisone or hydrocortisone acetate may be included in an amount ranging from 0.25% w/w to about 0.5% w/w. Menthol, phenol, and terpenoids, e.g., camphor, can be incorporated for cooling pain relief. For example, menthol may be included in an amount ranging from about 0.1% w/w to about 1.0% w/w. Antioxidants and/or preservatives may also be included.

Some exemplary formulations include an acylating agent; benzyl alcohol; lecithin; an organic solvent that is at least one of ethyl laurate, ethyl myristate, isopropyl myristate and isopropyl palmitate; nonionic surface acting agent; and a polar agent that is at least one of water, glycerol, ethylene glycol, formamide and hydroxyl-propylcellulose or in the alternative to the polar agent, one or more bile salts.

In one embodiment, the composition comprises: glutaric anhydride in an amount up to about 5.0% w/w; hydrocortisone in an amount of about 0.5% w/w; menthol in an amount of about 1.25% w/w; benzyl alcohol in an amount ranging from about 0.5% to about 10% w/w or about 2.0% w/w; lecithin organogel in an amount that is about 30% to about 60% w/w or 45% to about 55% w/w; and a nonionic surfactant in a bile salt, in an amount that is the remainder of the composition.

In another exemplary embodiment, the composition comprises: succinic anhydride in an amount up to about 5.0% w/w; hydrocortisone in an amount of about 0.5% w/w; menthol in an amount of about 1.25% w/w; benzyl alcohol in an amount ranging from about 0.5% to about 10% w/w; lecithin in an organic solvent in an amount that is about 40% to about 60%; a nonionic surfactant in an aqueous solution, in an amount that is the remainder of the composition.

In another embodiment, the composition comprises: succinic anhydride in an amount of about 10.0% w/w; menthol in an amount of about 1.25% w/w; benzyl alcohol in an amount of about 2.0% w/w; soy lecithin in isopropyl palmitate in an amount ranging from about 45% w/w to about 55% w/w; poloxamer in an aqueous solution in an amount (that is the remainder of the composition, and wherein the poloxamer is added to an intermediate mixture of the other constituents and subjected to mechanical shear force.

Formulations for Use to Dissolve Fat Noninvasively

In another embodiment, the essential components of the formulation are at least one active ingredient that is capable of dissolving fat along with suitable penetrants that will transduce the ingredients across the skin and into the fat deposit. Suitable fat-dissolving removing active ingredients include deoxycholic acid (DCA) and other bile salts including salts of taurocholic acid, glycocholic acid, taurochenodeoxycholic acid, glycochenodeoxycholic acid, and cholic acid. Certain detergents such as Tween® 80 and Span® 80 are also effective.

As to the penetrant, a particularly preferred penetrant includes combinations of benzyl alcohol and a lecithin organogel. In some embodiments the formulation also includes a nonionic surfactant. The level of benzyl alcohol is present in the range of 1%-20% by weight (w/w); the lecithin organogel in the range of 0.5%-70% w/w and the nonionic detergent and its counterbalancing polar solvent in the range of 0.10%-30% w/w. Specifically, the compositions described in the above cited US2009/0053290 incorporated herein by reference and PCT publication WO2014/209910, incorporated herein by reference are suitable for use in this application. It may be preferred, however, to use higher percentages of lecithin organogel and lower percentages of the benzyl alcohol component. The lecithin organogel may be present in amounts such as 5-60% w/w, 10-55% w/w, 20-40% w/w and intermediate ranges.

Thus, the invention includes formulations and methods for directly effecting diminution of local deposits of fat by administering at least one fat-dissolving compound in a composition comprising penetrants that permit transport of the fat-dissolving compound through the skin and into the fat deposit.

Applicants have observed that the results obtained by applying the fat dissolving compound topically and permitting transdermal conduction to the fatty deposit results in superior outcomes as compared to injection of comparable compounds. While not intending to be bound by any theory, it is believed that injection delivers a bolus of high concentration that is not allowed to distribute readily over the deposit. On the other hand, transdermal delivery is comparable to drizzling or soaking and thus permits a more even spread of similar concentrations of the fat dissolving compound throughout the deposit. When the fat cells are flooded, as by using injection with DCA for example, this induces adipocytolysis in a concentrated area. DCA also has a short half-life which is difficult to measure but is considered generally less than 30 minutes. Also, clear disadvantages of injection as compared to topical administration include adverse events associated with injection itself, and pain caused simply by the high concentration of DCA in a localized area. Adverse events associated with injection itself include side pain, swelling, numbness, bruising, erythema and induration. In clinical studies of injectable DCA, these adverse events were observed in 59% of subjects receiving placebo by injection and 95% of subjects receiving the current commercial dose of DCA.

This demonstrates that fat dissolving compounds such as DCA produce significant pain associated with the active ingredient over and above physical pain due to injection. This is illustrated by published data in an article by Renzi, et al., *Brit J Dermatol* (2014) 170:445-453 which showed that of subjects administered a placebo by injection, 47% of them experienced mild pain, 11% experienced moderate pain, and only 1% experienced severe pain. On the other hand, of all subjects injected DCA at the commercial dose, 30% experienced mild pain, 36% experienced moderate pain, and 27% experienced severe pain.

Thus, as described above, a particular application for supplying local anesthetic is to relieve any pain caused by the dissolution of fat whether the dissolution is provided by conventional methods such as injection or by the above-described method of transdermal transport. That said, the desirability of anesthetic treatment is much greater for the injection method; the discomfort caused by DCA per se is more chronic and low level than acute and excruciating.

Supplemental Nutrition

In another embodiment, nutrients are supplied transdermally. There are many occasions in which the formulations of the invention are useful. For athletes, the formulations can deliver to tired muscles sufficient amounts of a neutralizing agent for lactic acid, such as sodium bicarbonate, to relieve the burning sensation felt by the athlete due to the buildup of lactic acid. This permits the athlete to continue to perform at optimum level for longer periods of time. In addition, athletes or others "working out" are expending high amounts of energy and are in need of energy generation especially in those areas of their musculature that are involved in performing workouts and, therefore, need to consume large numbers of calories. These nutrients can be supplied directly rather than requiring oral ingestion which is counterproductive and relatively slow.

While athletes or individuals "working out" are used as illustrations herein, it is apparent that any individual subjected to tasks which require physical exertion would benefit from the compositions and methods of the invention. This includes, for example, construction workers, farm laborers, other laborers, soldiers and sailors or even individuals who ordinarily are not engaged in physical labor but on occasion are called upon to do so.

Emergency medical treatment of individuals requiring, for example, blood balancing agents including electrolytes and readily-metabolized nutrients, such as glucose, that would otherwise be administered intravenously can instead be non-invasively treated by massaging the formulation through the skin and thus permitting systemic delivery so that levels in the bloodstream are altered. Circumstances when this is desirable are well known, including emergency medication and postoperative treatments.

In addition to these applications, it has been noted that the administration of nutrients according to the invention also assuages feelings of hunger. Therefore, the formulations of the invention and methods of the invention are useful in promoting weight loss as the caloric intake required to assuage feelings of hunger is lower than that ordinarily experienced by consuming food conventionally. Thus, in addition to individuals requiring extra calories or metabolic balancers because of exertion and in addition to those unable to feed themselves orally, suitable subjects for the methods of the invention include individuals seeking to control their caloric intake in order to adjust their weight. In view of the generally acknowledged obesity epidemic in the United States in particular, this is an important group of subjects benefiting from the methods of the invention.

It is clear that the nature of the desired ingredients will vary depending on the object of the administration. Simple nutrients such as amino acids, glucose, fructose, simple fats, various vitamins, cofactors and antioxidants as well as somewhat more complex foodstuffs can be administered as well as neutralizing agents, depending on the need.

Exemplary active ingredients for athletic performance include beta-alanine, sodium bicarbonate, L-carnitine, adenosine triphosphate, dextrose, creatine monohydrate, beta-hydroxy-beta-methylbutyrate (HMB), branched chain amino acids (leucine, isoleucine, valine), glutathione, sodium phosphate, and caffeine.

Exemplary active ingredients for medical nutrition include amino acids, dextrose, lipids, $Na^+$, $K^+$, $Ca^{2+}$, $Mg^{2+}$, acetate, Cl—, P, multivitamin, and trace elements.

Exemplary active ingredients for weight loss include conjugated linoleic acids, ephedra, caffeine, and salicin.

In applying the formulations of the invention, the formulation itself is simply placed on the skin and spread across the surface and/or massaged to aid in penetration. The amount of formulation used is typically sufficient to cover a desired surface area. In some embodiments, a protective cover is placed over the formulation once it is applied and left in place for a suitable amount of time, i.e., 5 minutes, 10 minutes, 20 minutes or more; in some embodiments an hour or two. The protective cover can simply be a bandage including a bandage supplied with a cover that is impermeable to moisture. This essentially locks in the contact of the formulation to the skin and prevents distortion of the formulation by evaporation in some cases.

The schedule of application is dependent on the nature of the treatment being administered. Repeated application is often desirable, for example, during intermittent types of exercise. Alternatively, the formulation may be left in place, preferably covered during athletic performance. Application to supply nutrients to patients may also be for prolonged periods of time.

The composition may be applied to the skin using standard procedures for application such as a brush, a syringe, a gauze pad, a dropper, or any convenient applicator. More complex application methods, including the use of delivery devices, may also be used, but are not required.

It has surprisingly been found that using the formulations and methods of the present invention, nutrients can be supplied in effective amounts transdermally either preferentially to a desired area or systemically. Other agents which may be helpful in maintaining appropriate metabolic balance, for example, in muscles, can also be successfully administered in this manner. Thus, the need for oral administration, intravenous or other invasive administration of such active ingredients is obviated.

Hair Growth Modulation

In another embodiment, the active ingredient is any compound or material that is a hair growth modulator.

A number of compounds or compositions that stimulate hair growth are known in the art. Prominent among these are minoxidil which is of the formula

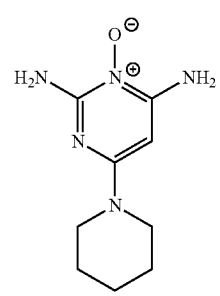

(1)

which has been shown at some level to be effective on topical treatment. However, the success rate for such treatments is minimal and it has not been particularly successful in reversing the alopecia caused by chemotherapy. By administering minoxidil in the formulations of the invention, a higher level of effectiveness for all forms of hair loss or inadequate hair growth can be achieved.

Another agent that has been found to stimulate hair growth is a prostaglandin analog with the generic name bimatoprost. This has the formula:

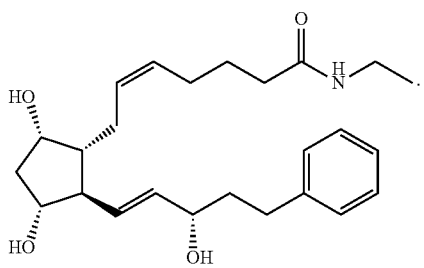

(2)

This compound has been used to restore eyelashes subsequent to chemotherapy. It has been marketed under the tradename Lumigan® and also as a cosmetic formulation under the name Latisse®. The effectiveness of this compound is also greatly improved by the formulations of the invention. Other analogs include latanoprost, travoprost and unoprostone.

Another compound known to stimulate hair growth is a retinoid with the generic name tretinoin. It is all-trans retinoic acid and has been marketed under a number of brand names, including Renova™, RetinA®, Avita®, and many others.

Another approach to providing active agents for hair growth stimulation takes advantage of compositions containing extracts of plant stem cells. These extracts are believed to stimulate the endogenous senescent stem cells present at the basis of the hair follicle—i.e., the dermal papilla. A particular lytic extract prepared from a cell line obtained by culturing stem cells derived from the tree *Argania spinosa* known commercially as PhytoCellTec™ Argan has been used generally to stimulate senescent stem cells that produce fibroblasts in vitro. The use of these compositions to reduce wrinkles is described by Schmid, D., et al. (Mibelle Biochemistry, Switzerland (2008). Applicants have now found that these extracts reverse the senescence of stem cells of the dermal papilla responsible for hair growth.

In addition to these, it is understood by applicants that certain other prostaglandins besides the analog bimatoprost also stimulate hair growth. These include $PGE_2$ and $PGF_{2\alpha}$.

An additional agent that is known to stimulate hair growth, especially in combination with bimatoprost is cyclosporin.

Alternatively, if inhibition of hair growth is desired, certain prostaglandins are known to effect hair growth inhibition. These include $PGD_2$ and its metabolite 15dPGJ$_2$. If hair growth inhibition is desired, these ingredients as active agents may be included in lieu of the stimulating compounds and preparations. The general method of application is the same, but the inhibition of hair growth would include application to areas that would not necessarily be subject to desirability of hair growth stimulation. Thus, for hair growth stimulation, application to the scalp or, in the case of men, facial areas, is indicated. Stimulation of eyelash growth involves application to the eyelid. For inhibition of hair growth, in women, for example, application to the face might also be desirable as well as to the limbs and underarms. The area of application is, of course, strictly speaking the decision of the subject and the treating practitioner.

The effectiveness of these and other hair growth modulating agents is greatly enhanced by employing them in the formulations of the invention which have superior penetrating qualities. In some embodiments, combinations of one or more such agents can be employed in the same formulation or sequentially. Thus, combinations of minoxidil with tretinoin or of tretinoin with bimatoprost or of either of these with stem cell extracts derived from apples or other plant tissue may be employed.

In addition to direct application to the skin, for example, the scalp or eyelids or facial skin, a technique proposed by RepliCel™ Life Sciences using a punch biopsy technique to harvest hair follicles from a scalp can be employed in combination with the formulations of the invention applied directly. In this technique, the punch biopsy harvests hair follicles followed by dissection of the dermal papilla and inversion of the dermal sheath cup. The dermal papilla is discarded and the dermal sheath cup is cultured yielding dermal cup cells in large numbers. The cells are then re-injected into the donor's scalp. These cells themselves could also be used as active ingredients in the formulations of the invention.

Other invasive methods are also known which can be used in combination with the formulations of the invention. In all cases where stem cells derived from the subject in question are cultured outside the subject, the cells are suitable as active ingredients in the formulations of the invention.

The compositions may be adjusted to pH 10-11 in some embodiments.

In one embodiment, the composition comprises: bimatoprost in an amount up to about 5.0% w/w; benzyl alcohol in an amount ranging from about 0.5% to about 10% w/w or about 2.0% w/w; lecithin organogel in an amount that is about 30% to about 60% w/w or 45% to about 55% w/w; and a nonionic surfactant in an aqueous solution, in an amount that is the remainder of the composition.

In another exemplary embodiment, the composition comprises: minoxidil in an amount up to about 5.0% w/w; benzyl alcohol in an amount ranging from about 0.5% to about 10% w/w; lecithin in an organic solvent in an amount that is about 40% to about 60%; a nonionic surfactant in an aqueous solution, in an amount that is the remainder of the composition.

In another embodiment, the composition comprises: tretinoin in an amount of about 5.0% w/w; benzyl alcohol in an amount of about 2.0% w/w; soy lecithin in isopropyl palmitate in an amount ranging from about 45% to about 55% w/w; poloxamer in an aqueous solution in an amount (that is the remainder of the composition, and wherein the poloxamer is added to an intermediate mixture of the other constituents and subjected to mechanical shear force.

In essentially anhydrous forms of the compositions, similar penetrants and active ingredients in similar amounts are employed, but rather than topping up to 100% with nonionic detergent in aqueous or other polar solution, the compositions are instead topped up with micronized or other powdered forms of nonionic detergents in the presence of bile salts. Essentially, the syrupy composition which results from the mixture of the alcohol and organogel along with active ingredient can be blended with a solid composition comprising the bile salt and nonionic detergent. In exemplary compositions, the bile salt is a salt of deoxycholic acid and the nonionic detergent is Pluronic® or other poloxamer (which is a copolymer of polyethylene glycol and N-polypropylene oxide). In exemplary compositions, for example, the active ingredient is a combination of minoxidil and tretinoin, the composition contains benzyl alcohol and lecithin isopropyl palmitate and is topped off with Pluronic® in micronized form and a salt of deoxycholic acid. In other exemplary compositions the deoxycholic acid salt is replaced by salts of, for example, taurocholic acid or cholic acid.

In an exemplary embodiment, PhytoCellTec™ Argan at 5% w/w in combination in benzyl alcohol at 0.9% w/w and lecithin isopropyl palmitate at 30% w/w is supplemented with deoxycholic acid at 1.5% w/w and Pluronic® in powdered form to bring to the total amount, adjusted to pH 10. (As this is anhydrous, the pH is measured by adding water to the composition before measurement.)

As noted above, the inclusion of epinephrine (epi) or other vasoconstrictor in the treatment is useful in many cases, and the exemplary embodiments above may be supplemented by application of, for example, a composition comprising epinephrine at 0.01% at pH 5. This can be done by applying the formulations sequentially or in layers.

The compositions disclosed herein may be delivered by a pump. In one embodiment, the pump is configured to deliver about 0.15 ml per stroke of the pump as a single dose. Delivering the composition by a pump allows the amount of the active ingredient needed to be easily calculated. For example, if the composition includes minoxidil in an amount of about 4% w/w of the composition and about 0.05 ml of minoxidil needs to be delivered to an area that is about 1 cm$^2$ then a pump that delivers 0.15 ml is used must be pumped eight times to deliver 1.2 ml/cm$^2$ of the composition to provide.

Nail Disorders and Fungal Infections Generally

It has surprisingly been found that using the formulations and methods of the present invention, clearing of disorders of the nail and nail bed can be effected in three weeks or less, as shown in Example 18 below. This represents essentially a 10-fold improvement over currently available compositions designed for topical treatment of these disorders. Without intending to be bound by any theory, applicants believe that the improvement is due to the enhanced ability of the formulations of the invention to permit penetration of the fingernail or toenail and the underlying skin by the active ingredient or ingredients in the formulations, so as to effect systemic delivery. Improvements have also been made in conducting the method of applying these formulations.

There are a number of commonly experienced disorders of the nail and nail bed that are treatable by the formulations and methods of the invention. Prominent among these is onychomycosis which is the most common of such conditions in adults. It is estimated that in North America, the incidence falls between 2-13% of the population. It is greater in older adults and up to 90% of elderly may be affected. It is a fungal infection often associated with other conditions. In the development of this condition, the nail becomes thicker and changes to a yellowish brown and may collect foul smelling debris under the nail.

Another common condition susceptible to treatment by the formulations and methods of the invention is psoriasis. This is a non-contagious inflammatory disease. Nail psoriasis is characterized by pitting of the fingernails or toenails and the affected nails may thicken, yellow or crumble. Sometimes the skin around the nail is also inflamed. Other diseases of the nail include inflammatory conditions, i.e., onychia or onychodystrophy which is generically malformation or discoloration in the nails due to illness or injury or subungual hematoma or koilonychia where the outer surfaces of the nail are concave.

In addition to nail and nail bed disorders per se, also suitable for treatment by the formulations and methods of the invention are conditions of the skin that can be treated topically. These conditions are often also fungal infections. Thus, among other symptomologies that can be treated are those associated with athlete's foot and jock itch. In addition, in some cases, psoriasis exhibited on skin areas generally is treatable using the same formulations by topical treatment of these compositions. Although these are conditions of the skin per se, in order to address them effectively, it is helpful to have the active ingredient in the formulation penetrate through the skin to attack the causative agents contained either within the dermis or immediately below.

It is evident that in view of the variety of types of nail, nail bed and skin disorders, the nature of the active ingredients may vary over a wide range. In some cases, the underlying cause is not understood and the subject may be benefited by providing, for example, vitamins, cofactors or nutritional aids to the localized region under the nail or on the skin. These may be useful supplements in any case.

Since a large percentage of nail, nail bed and superficial skin disorders are caused by fungi, including yeast, particularly useful active agents are antifungal agents such as medomycin, nystatin and amphotericin B, various imidazole compounds, such as miconazole, ketoconazole, clotrimazole, exonazole, bifonazole, butoconazole, fenticonazole, isoconazole, oxiconazole, sertaconazole, suconazole, and tioconazole; triazole compounds such as fluconazole, itraconazole, ravuconazole, posaconazole, and voriconazole and also the presently marketed oxaborole antifungal, tavaborole. Also useful are allyl amine compounds such as terbinafine, amorolfine, naftifine, and butenafine and the like. The choice of the active agent is arbitrary and any antifungal agent including those active against yeast should be effective for those conditions that are characterized by fungal infections. Exemplary agents also include echinocandin compounds such as anidulafungin, caspfungin, and micafungin; and other antifungal drugs such as ciclopirox, flucytosine, griseofulvin, gentian violet, haloprogin, tolnaftate, efinaconazole and undecylenic acid. Other types of drugs are more useful for other conditions of the nail and nail bed such as psoriasis and hematomas. For example, pharmaceutical agents may be effective such as anti-inflammatories, antibiotics, and anesthetics, vitamins and the like. Other agents that may be included in the formulation include antioxidants and moistening agents.

In applying the formulations of the invention for nail disorders, the formulation itself is simply placed on the nail and spread across the surface. The amount of formulation used is typically sufficient to cover the surface of the nail and the nail is left in contact with the formulation for at least 5 minutes, but preferably 10 minutes, 30 minutes or more. In some embodiments, a protective cover is placed over the formulation once it is applied and left in place for a suitable amount of time, i.e., 5 minutes, 10 minutes, 20 minutes or more; in some embodiments an hour or two. The protective cover can simply be a band-aid or other type of bandage including a bandage supplied with a cover that is impermeable to moisture. This essentially locks in the contact of the formulation to the nail and prevents distortion of the formulation by evaporation in some cases. The water content of the nail plate varies between 7% and 18% by weight. While somewhat counterintuitive in view of its hardness, the nail plate is about 1,000-fold more permeable to water than is skin. Due to its porosity, the nail plate can be rapidly hydrated and dehydrated. Occlusion of the nail alters the barrier properties of the nail. Occlusion of the nail plate for less than one hour results in distention of intercellular spaces through which polar and nonpolar substances can permeate more readily. Occlusion can be accomplished through the application of lacquer-like agents, band-aids, and the use of impermeable latex finger cots and these are best removed within an hour to prevent secondary inflammation.

Application of the formulations to treated superficial skin conditions such as athlete's foot, psoriasis and jock itch, similar techniques apply, often employing massaging the formulation into the affected area. It may be desirable in this case to apply a covering to the affected and treated area as well. The application times and intervals depend, of course, on the severity of the condition, the nature of the condition and the judgment of the practitioner.

In some typical protocols, for either nail or skin treatment, the application of the formulation is done as needed—typically one, two or three times daily and more frequently if needed. Repeated applications are also included within short timeframes such as three half-hour applications over the course of an afternoon. As above, the treatment schedule is dependent on the severity of the condition and the judgment of the practitioner treating the disorder. The treatment may be repeated over a substantial period of time, such as one week, two weeks or three weeks or more and the treatment may be done on a regular basis, such as daily, twice daily or once every two days, but may be staggered on an irregular basis as well—e.g., the first treatment on Day 1, a second treatment on Day 3, a third treatment on Day 4, a fourth treatment on Day 6, where the series does not exhibit any particular order. It should be emphasized that systemic delivery of the active agent is achieved.

In addition the regular debridement of the infected nail before application of the formulation gives an additional advantage of thinning the nail plate, thereby, further enhancing penetration.

In addition, nail growth is encouraged by supplying appropriate nutrients in the context of the penetrant of the invention. Various nutritional agents are supplied in this manner, including biotin, cystine, thiamine, pantothenic acid (Vitamin B5) and other suitable nutrients. The method of application and treatment is similar to that as described above for antifungal treatment.

The composition may be applied to the nail using standard procedures for application such as a brush, a syringe, a gauze pad, a dropper, or any convenient applicator. More complex application methods, including the use of delivery devices, may also be used, but are not required.

Antivirals

The formulations of the invention are also useful in delivering antiviral compounds. Some antiviral infections are superficial, but in some instances, systemic infection can also be beneficially treated by the penetrating formulations of the invention.

A number of antiviral agents are available, such as acyclovir (Zovirax®), valacyclovir (Valtrex®), famciclovir (Famvir®), penciclovir (Denavir®), foscarnet, cidofovir and docosanol (Abreva®). Most antiviral drugs are administered orally, but in many cases exhibit poor bioavailability due to "first-pass" metabolism, with only about 15% to 30% of the oral formulation being absorbed. Penciclovir (1% Denavir®), docosanol (10% Abreva®), and acyclovir (3% Zovirax®) are available as topical creams, which circumvents systemic metabolism; however, these formulations may not be adequately penetrating and are designed to treat superficial infections.

Penciclovir (Denavir® topical cream 1%) is claimed to "penetrate the skin to deliver penciclovir directly to the site of infection." Due to its high molecular weight, penciclovir is unlikely to breach intact skin and the stratum corneum barrier without chemical permeation enhancers in the formulation. It has been demonstrated to be more effective against HSV-infected cells than alternatives, such as Abreva®.

Abreva® is the only over-the-counter (OTC) topical dermal antiviral agent in the United States. The active agent in Abreva® is 10% docosanol, also known as behenyl alcohol. It is a saturated alcohol with 22 carbon atoms and used in the cosmetic trade as an emollient, emulsifier and thickener and has been approved by the Food and Drug Agency (FDA) as a pharmaceutical antiviral agent with claims that it reduces the duration of cold sores caused by the herpes simplex virus.

Corticosteroids have also been combined with antivirals in attempts to decrease the signs of inflammation, i.e., hyperemia, pain, edema and localized increase in skin temperature.

Methods of application of these antiviral agents, similar to those of other active ingredients, are typically by simple topical application, through massage or patch or by pumping devices.

Applications of the Invention Formulations and Methods

As is apparent from the discussion above, the penetrants of the invention have wide application and are applicable to a number of drug delivery scenarios and can be adapted to the administration of a wide variety of active components. The extent of delivery is dependent on the application—simple transdermal transmission to a site of action as in the case of local anesthetics, treatment of fingernails or toenails, or volume and texture enhancement of tissue are examples of local delivery. On the other hand, delivery of nutrients and in some cases antiviral agents and anti-infective agents as well as cannabinoids and pain killers such as NSAIDs can be systemic. The particular choice of formulation within the scope of the invention and the level of active ingredient, the time of application, the frequency of application, and the dosage levels overall are within the judgment of the practitioner and within the skill of the art.

Notably, local anesthetics can readily be delivered using the formulations of the invention by simple application to the skin. In this case, the use of epinephrine is beneficial as is the use of high pH—e.g., pH 9-11. Because epinephrine is not stable at such high pH's, either it should be delivered separately in tandem with the delivery of the anesthetic itself in a composition of suitable pH, or it may be stabilized by adding an appropriate stabilizing agent such as Desferal® in the context of the anesthetic composition itself.

In general, the invention is directed to administering a local anesthetic to a subject transdermally and a formulation which contains an effective amount of anesthetic along with 25%-70% w/w or 30%-60% w/w or 30%-40% w/w of lecithin organogel typically wherein the lecithin organogel comprises soy lecithin in combination with isopropyl palmitate or isopropyl myristate and benzyl alcohol in the range of 0.5%-20% w/w or 0.9%-2% w/w benzyl alcohol optionally including 1%-5% w/w or 2%-4% w/w menthol wherein the composition is topped off with a polar solution, typically an aqueous solution comprising 15%-50% w/w or 20%-40% w/w or 20%-30% w/w poloxamer, typically Pluronic® or alternatively may be an anhydrous composition comprising bile salts such as deoxycholic acid or sodium deoxycholate in the range of 4%-8% w/w, typically 6% w/w and the remainder of the composition powdered nonionic detergent, typically Pluronic®. The pH of the compositions is adjusted to 9-11, typically 10-11. The formulations are applied to the desired area of the skin and may be covered, for example, with Saran™ wrap for a suitable amount of time. Following the treatment, the skin can be repaired by applying a composition comprising linoleic acid.

Similar formulations as described above are used wherein the active component is an antifungal or a combination of antifungals, a nutrient or combination of nutrients, a dicarboxylic anhydride, or a hair growth modulator. The location for application will, of course, depend on the use—typically antifungals are applied to fingernails or toenails; hair growth modulators applied to the scalp, dicarboxylic acid anhydrides or inhibitors of hyaluronidase or enhancers of hyaluronic acid synthase to areas of the skin or tissue where enhanced volume or quality is desired, and nutrients to, for example, muscle tissue.

In the case of the use of dicarboxylic anhydrides for tissue volume enhancement, again, high pH is indicated and the composition must be administered in such a way as to prevent hydrolysis prematurely as described above. Agents that adjust the level of hyaluronic acid in tissue are also indicated for enhancing the quality of tissue.

Systemic administration of nutrients is especially important as is the treatment of viral infection, bacterial infection or other microbial infection using standard methods. Other applications include modulation of hair growth and treatment of nail disorders as further described above. For smoking cessation, one active ingredient is cytisine, also known as baptitoxine and sophorine, and is an alcohol that occurs naturally in several plant genera. It is available commercially.

Suitable active agents to be delivered in using the formulations for treatment of post procedural bruising include helenalin, a sesquiterpene, a lactone as well as Vitamin K. The formulation based on helenalin may be accompanied by irradiation with light of wavelength 577-595 nm. Other active agents include Botox®, flavonoids, skin lighteners and materials that promote collagen biosynthesis.

In all cases, once the application has been made to an appropriate skin, nail or hair follicle area, the area can be sealed with a composition comprising linoleic acid.

One particular application is localized fat removal using, for example, bile salts as active ingredients. In this instance, the level of lecithin organogel present in the composition may be lower than in the remaining formulations. The administration of the bile salt or bile acid to remove fat may be accompanied by administration of anesthetic regardless of the method of delivery of the fat-dissolving compound.

Thus, the invention is directed to compositions with the penetrants of the invention as effective aids in transdermal delivery.

The following examples are provided to illustrate but not to limit the invention.

Example 1

Dose Dependence of Pain Relief

Compositions were prepared that comprised lidocaine in varying amounts including 4.0%, 10%, 15%, and 30% w/w. The compositions also comprised benzyl alcohol in an amount of 2% w/w and lecithin isopropyl palmitate in an amount of 22% w/w. The remainder was a stock cream formulation such as that sold as VaniCream™. No poloxamer was included in the composition.

Ultherapy, which is focused ultrasound, was used to induce pain. Pain was induced at varying depths on the forearms of two male subjects, and compared to pain on an area of the arm of the test subjects that was not treated with the composition. The subjects were treated with the various transducers at three levels, 1.5 mm, 3.0 mm and 4.5 mm. Pain was measured using the visual analog (VAS) pain scale, which is a validated pain scale in which test subjects rank pain on a scale of 0 to 10, 1-3=very minor, 4-6=minor but tolerable, 7>=painful. Below are the averaged pain results:

| | Lidocaine | | | No Lidocaine | | |
|---|---|---|---|---|---|---|
| Dose | 1.5 mm | 3.0 mm | 4.5 mm | 1.5 mm | 3.0 mm | 4.5 mm |
| 4% | 3.13 | 4.75 | 6.25 | 7.50 | 9.00 | 9.50 |
| 10% | 3.13 | 4.75 | 6.25 | 7.00 | 8.50 | 9.34 |
| 15% | 3.13 | 4.75 | 5.75 | 6.63 | 8.00 | 9.17 |
| 30% | 2.13 | 3.75 | 5.5 | 6.25 | 7.50 | 9.00 |

By comparing these measurements of pain as measured with the compositions and without the compositions, the percentages of pain attenuation were determined as provided below:

| Dose | 1.5 mm | 3.0 mm | 4.5 mm |
|---|---|---|---|
| 4% | 58% | 47% | 34% |
| 10% | 55% | 44% | 33% |
| 15% | 53% | 41% | 37% |
| 30% | 66% | 50% | 39% |

The conclusion based on these data is that pain attenuation was dose dependent because higher pain attenuation resulted from higher doses of lidocaine. Additionally, the pain attenuation was depth dependent because as the depth increased, there was less pain attenuation.

Example 2

Compositions Containing Detergent

Compositions were prepared that comprised lidocaine in varying amounts including 4.0% and 30% w/w. The compositions also comprised benzyl alcohol in an amount of 2% w/w, lecithin isopropyl palmitate in an amount of 22% w/w. In composition #1, poloxamer PEG/propylene glycol (20% w/w by volume of solution) was used top off the composition to 100% by weight of the composition. In composition #2, Aquaphor® sold by Eucerin® was used to top off the benzyl alcohol and lecithin isopropyl palmitate instead of poloxamer. Ultherapy was used to induce pain and the pain was measured using the VAS scale. Pain was induced at varying depths on three test subjects.

Below are the measured pain results for compositions #1 and #2 using 30% w/w lidocaine on subject A:

| | 1.5 mm | 3.0 mm | 4.5 mm |
|---|---|---|---|
| #1 | 2.50 | 0.50 | 1.50 |
| #2 | 3.50 | 2.00 | 3.50 |

Below are the measured pain results for compositions #1 and #2 using 30% w/w lidocaine on subject B:

|  | 1.5 mm | 3.0 mm | 4.5 mm |
|---|---|---|---|
| #1 | 0.50 | — | 3.00 |
| #2 | 4.50 | — | 6.00 |

Below are the measured pain results for compositions #1 and #2 using 4% w/w lidocaine on subject C:

|  | 1.5 mm | 3.0 mm | 4.5 mm |
|---|---|---|---|
| #1 | 2.50 | 1.00 | 2.00 |
| #2 | 7.00 | 3.00 | 5.00 |

Pain was also measured and averaged, as provided below, on an area of the arm of the test subjects that was not treated with the compositions.

Below are the measured pain results on subject A on area not treated with the composition:

|  | 1.5 mm | 3.0 mm | 4.5 mm |
|---|---|---|---|
| #1 | 6.00 | 5.50 | 8.00 |
| #2 | 6.00 | 5.50 | 8.00 |

Below are the measured pain results on subject B on area not treated with the composition:

|  | 1.5 mm | 3.0 mm | 4.5 mm |
|---|---|---|---|
| #1 | 7.50 | 6.00 | 8.00 |
| #2 | 7.50 | 6.00 | 8.00 |

Below are the measured pain results on subject C on area not treated with the composition:

|  | 1.5 mm | 3.0 mm | 4.5 mm |
|---|---|---|---|
| #1 | 8.50 | 5.50 | 8.00 |
| #2 | 8.50 | 5.50 | 8.00 |

By comparing these measurements of pain as measured with the compositions and without the compositions, the percentages of pain attenuation were determined as provided below.

Subject A's percentage of pain attenuation:

|  | 1.5 mm | 3.0 mm | 4.5 mm |
|---|---|---|---|
| #1 | 58% | 91% | 81% |
| #2 | 42% | 64% | 56% |

Subject B's percentage of pain attenuation:

|  | 1.5 mm | 3.0 mm | 4.5 mm |
|---|---|---|---|
| #1 | 93% | 100% | 63% |
| #2 | 40% | 100% | 25% |

Subject C's percentage of pain attenuation:

|  | 1.5 mm | 3.0 mm | 4.5 mm |
|---|---|---|---|
| #1 | 71% | 82% | 75% |
| #2 | 18% | 45% | 38% |

The conclusion based on these data is that the use of poloxamer with lecithin isopropyl palmitate unexpectedly increased pain attenuation at all depths and independent of lidocaine concentration.

Example 3

Effect of Lecithin Organogel Concentration

Compositions were prepared that comprised lidocaine in an amount of 5.0% w/w. The compositions also comprised benzyl alcohol in an amount of 2% w/w, lecithin isopropyl palmitate in amounts of 30%, 40%, 50% and 60% w/w, and the composition was topped off with poloxamers to yield 100% of the composition w/w. Pain was induced using an 18 gauge needle with a length of one inch. Pain was measured using the VAS pain scale.

Below are the depths to which the needle was inserted on the forearm of a subject:

| Formulation | 30% | 40% | 50% | 60% |
|---|---|---|---|---|
| 5 minutes | 20 mm | 26 mm | 26 mm | 26 mm |
| 8 minutes | 22 mm | 26 mm | 26 mm | 26 mm |
| 10 minutes | 22 mm | 26 mm | 26 mm | 26 mm |
| Surface pin pricks | 1-2 | 2-2 | 2-2 | 2-3 |

The tests showed that using lecithin isopropyl palmitate with poloxamer increased the pain attenuation at all depths and was independent of lidocaine concentration. Further, the tests showed that increasing the amount of lecithin isopropyl palmitate to 40% w/w resulted in an ability to penetrate the needle more deeply with tolerable pain. Qualitative surface pin pricks showed that there was some pain, which indicates that the composition quickly permeated to greater depths.

Example 4

Delivery of Anesthetic

Pain attenuation was compared using compositions with amounts of lecithin isopropyl palmitate of 0.6%, 20%, 40% and 60% w/w. The compositions included 5% lidocaine. Each composition is topped off with poloxamer (20% solution) to yield a thermogel emulsion with the rheology of a cream.

The compositions were applied to the forearms of two test subjects for either 5 minutes or 10 minutes after which pain was induced a 4.5 mm depth using focused ultrasound. Data were averaged for the two test subjects as shown below. Pain was tested without any composition on the skin as a control.

For 5 minutes of application:

|  | 0.6% | | 20% | | 40% | | 60% | |
| --- | --- | --- | --- | --- | --- | --- | --- | --- |
|  | Control | Active | Control | Active | Control | Active | Control | Active |
|  | 9 | 10 | 10 | 8 | 10 | 7 | 10 | 4 |
| Pain rating % decreased | 11% | | −25% | | −38% | | −50% | |

For 10 minutes of application:

|  | 0.6% | | 20% | | 40% | | 60% | |
| --- | --- | --- | --- | --- | --- | --- | --- | --- |
|  | Control | Active | Control | Active | Control | Active | Control | Active |
|  | 8 | 9.3 | 8.3 | 6.5 | 8 | 5 | 9 | 5.8 |
| Pain rating % decreased | 16% | | −21% | | −38% | | −36% | |

The amount of pain decreased as the lecithin isopropyl palmitate increased. Forty percent (40%) lecithin isopropyl palmitate vs. 60% may be advantageous as it provides ability to add more poloxamer so that the composition has more gel-like properties.

Example 5

Delivery of Anesthetics Using the Compositions of the Invention

All of the formulations and protocols below are of the present invention.

The following protocol was employed:
1. Cleanse skin, rinse and pat dry;
2. Exfoliate skin with a mild exfoliator (e.g., Offects® Exfoliating Polish from ZO® Skin Health), rinse off, pat dry;
3. Skin stripping: use clear packing tape, place on skin and strip away to remove dead skin cells;
4. Occlusion: Place formulation on skin, cover with plastic wrap, such as Saran™ Wrap, leave on for 15-20 minutes, then remove plastic wrap, clean off any remaining cream;
5. Assess pain and pain mitigation: conduct procedure. Have subject self-assess pain first in an untreated area to provide context, then in the treated area. Use the VAS pain scale (0-10), where 0 is no pain and 10 is very intense pain.

The manner of inflicting pain was as follows. In all cases, pain was assessed in untreated areas which are subjected to the same pain stimuli for comparison.
1. Laser: use PaloVia™ hand-held Skin Renewing Laser™ (made by Palomar Medical Technologies, now part of Cynosure, Inc.). Set to highest setting, fire 1-2 pulses to experience pain.
2. Needles: use 20 gauge needle to create pinpricks on skin. Use 18 gauge needle for deep needle test: push needle through skin of forearm and push in up to 25 mm.
3. Ultherapy: override default setting and re-set machine to highest energy level. Fire 3 cycles first at the 4.5 mm depth, then 3.0 mm depth, then 1.5 mm depth. Record pain at each level for treated skin.
4. Deoxycholic acid (DCA) injection 10 mg/mL: inject 0.2 mL (2 mg) into abdomen.

The results are as shown in the chart below; a semicolon indicates separate sessions. In general, the pain rating for untreated areas was 9-10.

Abbreviations used:
B=benzocaine, L=lidocaine, T=tetracaine,
epi=epinephrine,
BA=benzyl alcohol;
LIP=soy lecithin isopropyl palmitate organogel.

All formulations have 30% LIP, and are QS (topped off) with pluronic 30% w/w aqueous solution.

DCA injection is of bovine source DCA (Kybella™ injection for submental fat uses a synthetically-derived version of DCA).

Pain scores represent averages to date using the VAS pain chart (0-10) BLT=benzocaine 20%, lidocaine 6%, tetracaine 4% (all w/w).

BLT (20/6/4)+epi=benzocaine 20%, lidocaine 6%, tetracaine 4%, epinephrine 0.01% (all w/w).

In particular experiments, steps 1-3 above were followed, lidocaine and/or tetracaine was applied first, covered with Saran™ Wrap and after 10 minutes, followed by uncovering and applying benzocaine and covering again, for 10 minutes followed by removing Saran™ Wrap, cleansing skin and following step 5 above.

TABLE 1

| | pH | Laser | Needles | Ultherapy | | | DCA injection (10 mg/mL) 0.2 mL (2 mg)/dose | Average |
| --- | --- | --- | --- | --- | --- | --- | --- | --- |
| | | | | 1.5 | 3.0 | 4.5 | | |
| B 20%, L 6%, T 4%, BA 2%, pH 10 | 10 | 2.5 | 3.25 | 2.5 | 2 | 3 | 2.7 | 2.7 |
| B 20%, L 6%, T 4%, epi 0.01%, BA 2%, pH 5 | 5 | 0.8 | 2.5 | 3.3 | 0.5 | 1 | 1.4 | 1.6 |
| B 20%, L 6%, T 4%, epi 0.01%, BA 2%, pH 10 | 10 | | | | | | | |
| B 20%, L 6%, T 4%, epi 0.01%, BA 0.9%, pH 5 | 5 | | | | | | | |
| B 20%, L 6%, epi 0.01%, BA 2%, pH 5 | 5 | | | | | | | |
| B 20%, L 6%, epi 0.01%, BA 0.9%, pH 5 | 5 | | | | | | | |
| B 20%, epi 0.01%, BA 0.9%, pH 5 | 5 | 2.7 | 2.8 | 2 | 0.5 | 1.5 | 1.8 | 1.9 |
| B 20%, BA 2%, pH 10 | 10 | 2 | 3.3 | 3 | 1.5 | 4 | | 2.8 |
| B 20%, BA 10%, pH 10 | 10 | 2 | 3.3 | 3 | 1.5 | 4 | | 2.8 |
| T 1%, epi 0.01%, BA 0.9%, pH 5 | 5 | 4.25 | 4.75 | 7.3 | 5 | 4.7 | | 5.2 |
| T 2%, BA 2%, pH 10 | 10 | 2.6 | 2.75 | 6 | 3.3 | 3.3 | 0.75 | 3.1 |
| L 5%, BA 0.9%, epi 0.01%, pH 5 | 10 | 2.5 | 4.7 | 7.3 | 5 | 4.3 | | 4.8 |
| L 5%, BA 0.9%, pH 10 | 5 | 2 | 2 | 5.3 | 2 | 2 | 1.25 | 2.4 |

In the following Table 2 the following compositions were used.
3=B 20%, BA 0.97%, LIP 30%, epi 0.01%, pH5
7=T 2%, BA 2%, LIP 30%, pH10
10=L 5%, BA 0.9%, LIP 30%, epi 0.01% pH5
11=epi 0.01%, BA 0.9%, LIP 30%, pH5
12=BLT 20/6/4, BA 2%, LIP 30%, pH10
13=B 20%, BA 0.9%, LIP 30%, pH10
14=B+L 20/20, BA 2%, LIP 30%, pH10
15=L 5%, BA 0.9%, LIP 30%, pH10
All were topped up with 30% Pluronic® in water.

TABLE 2

|  | pH | Laser | Needles | Ultherapy 1.5 | Ultherapy 3.0 | Ultherapy 4.5 | DCA injection (10 mg/mL) 0.2 mL (2 mg)/dose | Average |
|---|---|---|---|---|---|---|---|---|
| Products used together |  |  |  |  |  |  |  |  |
| BLT 10 + 7 + 3 |  | 1 | 1 | 8 | 7 | 7 | 0.3 | 4.1 |
| B + L 10 + 3 |  | 3 | 2 | 7.5 | 7.5 | 5.8 | 1 | 4.5 |
| Epi + Caine stepwise treatment |  |  |  |  |  |  |  |  |
| BLT 11 + 12 | 10 | 1.3 | 3.0 | 7.4 | 3.4 | 4.6 |  | 3.9 |
| B 11 + 13 | 10 | 1.5 | 3.8 | 8.0 | 3.3 | 5.3 |  | 4.4 |
| B + L 11 + 14 | 10 | 1.6 | 1.6 | 6.3 | 2.3 | 5.3 |  | 3.4 |
| L 11 + 15 | 10 | 1.0 | 4.6 | 7.5 | 2.1 | 7.1 |  | 4.5 |
| BLT 11 + 12' | 10 | 0.3 | 0.8 | 1.6 | 1.1 | 2.4 | 2 | 1.4 |
| BLT 12 + 11 | 10 | 0.1 | 1.4 | 1.8 | 0.3 | 0.5 | 1.5 | 0.9 |
| B + L 14 + 11 | 10 | 0.8 | 2.3 | 2.5 | 1.5 | 2.5 |  | 1.9 |
| B + L 14-11' | 10 | 0.8 | 1.8 | 3.0 | 1.3 | 2.3 |  | 1.8 |
| BLT (12 for 5 min., 11 for 5 min.) | 10 | 2.5 | 4.5 | 3.8 | 5.5 | 4.0 |  | 4.1 |
| BLT (12 for 10 min., 11 for 10 min.) | 10 | 1.0 | 1.3 | 2.8 | 6.3 | 3.8 |  | 3.0 |
| BLT (12 for 5 min., 11 for 15 min.) | 10 | 0.8 | 1.3 | 3.0 | 7.0 | 3.3 |  | 3.1 |
| BLT (12 for 15 min., 11 for 5 min.) | 10 | 0.1 | 0.5 | 1.8 | 6.3 | 4.5 |  | 2.6 |
| B (13 for 20 min., 11 for 20 min.) | 10 | 1.0 | 2.3 | 3.3 | 4.5 | 3.8 |  | 3.0 |
| L (15 for 20 min., 11 for 20 min.) | 10 | 1.2 | 2.7 | 3.3 | 3.8 | 2.7 |  | 2.7 |
| BLT: 12 + 11 (12 for 12 min., 11 for 5 min.) | 10 | 1.5 | 3.3 | 3.0 | 3.8 | 3.3 |  | 3.0 |
| BLT: 12 + 11 (12 for 20 min., 11 for 5 min.) | 10 | 0.8 | 2.5 | 2.0 | 2.5 | 3.3 |  | 2.2 |
| BLT: 12 + 11 (12 for 5 min., 11 for 5 min.) | 10 | 1.0 | 2.0 | 3.0 | 2.1 | 4.5 |  | 2.5 |
| BLT: 12 + 11 (12 for 15 min., 11 for 5 min., pain stimulus at minute 35) | 10 | 0.3 | 1.5 | 1.8 | 1.5 | 2.2 |  | 1.5 |
| BLT: 12 + 11 (12 for 30 min., 11 for 5 min., pain stimulus at minute 35) | 10 | 0.2 | 0.3 | 1.0 | 1.8 | 1.3 |  | 0.9 |
| L + B + epi: 15 + 13 + 11 (15 for 30 min., 13 for 15 min., 11 for 15 min.) | 10 | 0.8 | 0.3 | 2.7 | 3.7 | 4.2 |  | 2.3 |
| L + B + epi: 15 + 13 + 11 (15 for 20 min., 13 for 10 min., 11 for 10 min.) | 10 | 2.0 | 1.7 | 3.5 | 2.8 | 4.2 |  | 2.8 |
| L + B + epi: 15 + 13 + 11 (15 for 15 min., 13 for 10 min., 11 for 5 min.) | 10 | 2.0 | 2.2 | 5.0 | 5.2 | 2.5 |  | 3.4 |
| BLT: 12 + 11 (12 for 15 min., 11 for 5 min., pain stimulus at minute 20) | 10 | 0.2 | 1.3 | 1.3 | 3.0 | 1.8 |  | 1.5 |
| BLT: 12 + 11 (12 for 20 min., 11 for 5 min.) | 10 | 0.1 | 0.2 | 0.3 | 1.0 | 1.0 |  | 0.5 |
| BLT: 12 + 11 (12 for 25 min., 11 for 5 min.) | 10 | 0.1 | 0.2 | 0.3 | 1.7 | 0.8 |  | 0.6 |
| BLT: 12 + 11 (12 for 30 min., 11 for 5 min., pain stimulus at minute 35) | 10 | 0.4 | 0.7 | 0.4 | 1.5 | 2.0 |  | 1.0 |
| BLT: 12 + 11 (12 for 35 min., 11 for 5 min.) | 10 | 0.5 | 1.2 | 1.2 | 2.2 | 2.3 |  | 1.5 |
| Caine layering + epi: |  |  |  |  |  |  |  |  |
| L + B + epi (15 + 13 + 11) Layer: L (25 min.), B (25 min.), epi (5 min.) | 10 | 2 | 2.3 | 2.7 | 3.2 | 4.3 |  | 2.9 |
| L + B + epi (15 + 13 + 11) Layer: L (25 min.), B (15 min.), epi (5 min.) | 10 | 0.3 | 1.7 | 3.3 | 2.3 | 4.3 |  | 2.4 |
| B + L + epi (13 + 15 + 11) Layer: B (25 min.), L (25 min.), epi (5 min.) | 10 | 2.5 | 2.3 | 3.0 | 1.5 | 4.7 |  | 2.8 |
| B + L + epi (13 + 15 + 11) Layer: B (25 min.), L (15 min.), epi (5 min.) | 10 | 0.4 | 2.3 | 3.5 | 2.5 | 1.8 |  | 2.1 |
| Caine wipe off + epi: |  |  |  |  |  |  |  |  |
| L + B + epi (15 + 13 + 11): L (25 min., wipe off), B (25 min., wipe off), epi (5 min.) | 10 | 1.0 | 0.7 | 3.0 | 0.8 | 3.0 |  | 1.7 |
| L + B + epi (15 + 13 + 11): L (25 min., wipe off), B (15 min., wipe off), epi (5 min.) | 10 | 0.0 | 0.9 | 3.2 | 1.2 | 1.2 |  | 1.3 |
| B + L + epi (13 + 15 + 11): B (25 min., wipe off), L (25 min., wipe off), epi (5 min.) | 10 | 0.0 | 1.5 | 3.3 | 1.5 | 1.0 |  | 1.5 |
| B + L + epi (13 + 15 + 11): B (25 min., wipe off), L (15 min., wipe off), epi (5 min.) | 10 | 0.1 | 1.8 | 3.7 | 0.6 | 2.2 |  | 1.7 |
| L + B + epi (15 + 13 + 11): L (5 min., wipe off), B (20 min., wipe off), epi (5 min.) | 10 | 0.2 | 1.2 | 2.2 | 3.2 | 0.8 |  | 1.5 |

TABLE 2-continued

| | pH | Laser | Needles | Ultherapy 1.5 | 3.0 | 4.5 | DCA injection (10 mg/mL) 0.2 mL (2 mg)/dose | Average |
|---|---|---|---|---|---|---|---|---|
| B + L + epi (13 + 15 + 11): Layer: B (5 min.), L (20 min.), epi (5 min.) | 10 | 0.4 | 1.0 | 3.2 | 1.5 | 0.8 | | 1.4 |
| BLT + epi wipe time test: | | | | | | | | |
| BLT (12) (20 min.) + epi (11) (5 min.): 15 min. after wipe | 10 | 0.3 | 0.3 | 1.0 | 0.8 | 0.9 | | 0.6 |
| BLT (12) (20 min.) + epi (11) (5 min.): 30 min. after wipe | 10 | 0.5 | 1.0 | 0.5 | 2.5 | 0.9 | | 1.1 |
| BLT (12) (20 min.) + epi (11) (5 min.): 45 min. after wipe | 10 | N/A | 1.5 | 1.5 | 0.9 | 2.5 | | 1.6 |
| BLT (12) (20 min.) + epi (11) (5 min.): 75 min. after wipe | 10 | N/A | 1.0 | 0.8 | 1.8 | 2.8 | | 1.6 |
| BLT (12) (20 min.) + epi (11) (5 min.): 105 min. after wipe | 10 | N/A | 2.0 | 3.0 | 3.5 | 4.0 | | 3.1 |
| BLT (12 + 11) (12 for 20 min., then 11 for 5 min., then wiped off, then tested at 30 min.) | 10 | 0.3 | 1.3 | 2.0 | 2.7 | 2.5 | | 1.8 |
| B + L + epi: (13 for 5 min., then wipe off, then 15 for 5 min., then epi for 5 min., then wipe off, then tested at 30 min.) | 10 | 1.25 | 3 | 4.5 | 3 | 4.5 | | 3.3 |
| B + L + epi: (13 for 10 min., then wipe off, then 15 for 10 min., then epi for 5 min., then wipe off, then tested at 30 min.) | 10 | 0.85 | 2.25 | 3 | 2.5 | 4 | | 2.5 |

In Table 3, the listed epinephrine was incubated for 72 hours with Desferal®, an iron chelator. All are QS with 30% Pluronic®. The compositions used are:

16=BLT 20/6/4 Desferal® 0.1%, BA 2%, epi 0.01%, LIP 30%, pH10;

17=B 20%, Desferal® 0.1%, BA 0.9%, epi 0.01%, LIP 30%, pH10; and

18=L 5%, Desferal® 0.1%, BA 0.9%, LIP 30, epi 0.01%, pH10.

TABLE 3

| | pH | Laser | Needles | Ultherapy | | | DCA injection (10 mg/mL) 0.2 mL (2 mg)/dose | Average |
|---|---|---|---|---|---|---|---|---|
| BLT: 16 (16 for 20 min.) | 10 | 0.1 | 0.2 | 1.3 | 1.7 | 1.8 | | 1.0 |
| BLT: 16 (16 for 30 min.) | 10 | 0.3 | 0.7 | 2.0 | 1.8 | 1.5 | | 1.3 |
| L + B: 18 + 17 (18 for 20 min., 17 for 10 min.) | 10 | 0.5 | 1.7 | 2.8 | 3.0 | 2.8 | | 2.2 |
| BLT w/Desferal ® wipe time test: | | | | | | | | |
| BLT w/Desferal ® (25 min.): tested at 15 min. after wipe | 10 | 0 | 0.4 | 0.5 | 3.0 | 2.3 | | 1.2 |
| BLT w/Desferal ® (25 min.): tested at 30 min. after wipe | 10 | 0 | 1.5 | 0.8 | 1.0 | 3.8 | | 1.4 |
| BLT w/Desferal ® (25 min.): tested at 45 min. after wipe | 10 | N/A | 1.5 | 1.5 | 3.3 | 1.8 | | 2.0 |
| BLT w/Desferal ® (25 min.): tested at 75 min. after wipe | 10 | N/A | 1.6 | 1.5 | 1.8 | 2.6 | | 1.9 |
| BLT w/Desferal ® (25 min.): tested at 105 min. after wipe | 10 | N/A | 1.1 | 3.0 | 4.8 | 5.0 | | 3.5 |

DCA Injection

Anhydrous Formulations. In Table 4, all compositions were QS with powdered Pluronic®. The compositions used are:

19=BLT 20/6/4, epi 0.01%, Desferal® 0.1%, BA 0.9%, LIP 30%, DCA 6%, pH10;

20=B 20%, epi 0.01%, Desferal® 0.1%, BA 0.9%, LIP 30%, DCA 6%, pH10;

21=L 5%, epi 0.01%, Desferal® 0.1%, BA 2%, LIP 30%, DCA 6%, pH10; and

22=BLT 20/6/4, BA 2%, LIP 30%, DCA 6%, pH10

TABLE 4

| | pH | Laser | Needles | Ultherapy | | | DCA injection (10 mg/mL) 0.2 mL (2 mg)/dose | Average |
|---|---|---|---|---|---|---|---|---|
| BLT (19 for 20 min., then wiped off, tested at 30 min.) | 10 | 1.2 | 2.5 | 3.7 | 4.7 | 3.3 | | 3.1 |
| BLT (19 for 30 min., then wiped off, tested at 30 min.) | 10 | 1.5 | 2.2 | 3.5 | 3.8 | 3.5 | | 2.9 |
| B + L (20 for 5 min., then wiped off, then 21 for 20 min., then wiped off, then tested at 30 min.) | 10 | 1.2 | 2.2 | 3.7 | 4.7 | 2.5 | | 2.8 |
| BLT 22 for 20 min., then epi (11) for 5 min., then wipe off, then tested at 30 min. | 10 | 0.75 | 2.25 | 7 | 5.5 | 6 | | 4.3 |

Example 6

Treatment of Crow's Feet

Two subjects were treated to smooth-out crow's feet thus enhancing the tissue volume next to the eye.

Figure 1B:
Figure 2A:
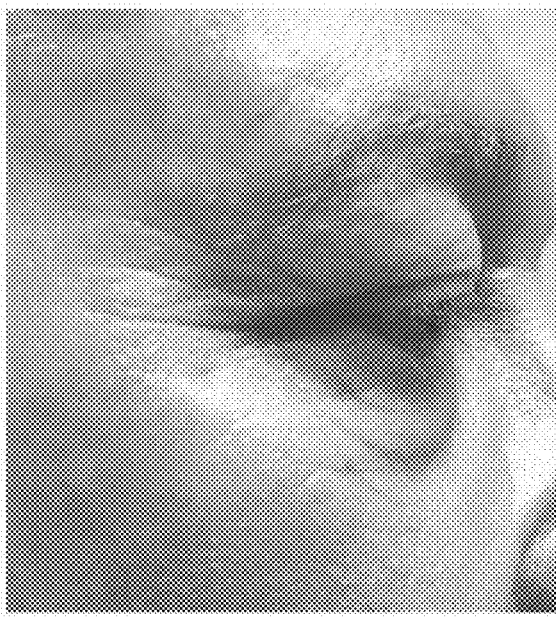
FIGS. 2A and 2B show the sustained effect of this treatment where the subject shown in FIG. 1A is shown again in FIG. 2A and in FIG. 2B the same subject is shown approximately four months after treatment.
Figure 2B:
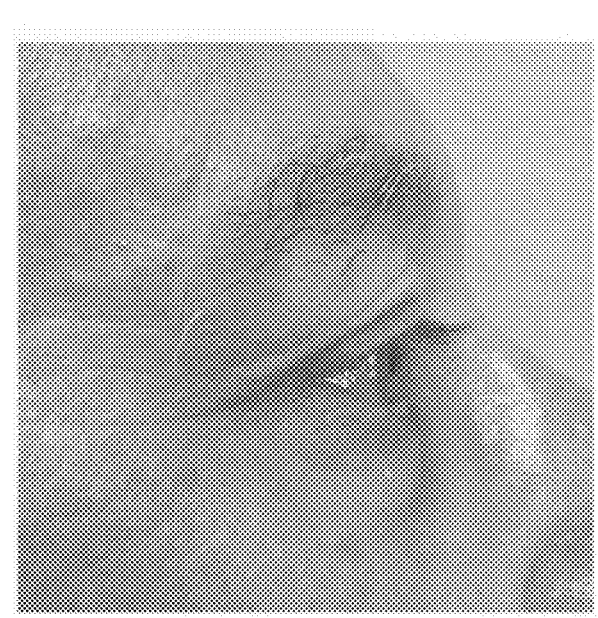

In both cases, the skin next to the eye was cleansed and exfoliated using sticky tape and cleansed with isopropyl alcohol. A formulation containing 65% w/w of Pluronic® lecithin organic gel made up of 33.17% poloxamer 407 powder, 33.17% soy lecithin granules, and 33.17% isopropyl palmitate syrup was mixed with 2% w/w benzyl alcohol and buffer to pH 10-11 wherein the buffer comprises 10 g sodium bicarbonate and 12.6 g of sodium carbonate along with 0.5 g of sorbate acid as a preservative. This was applied and allowed to remain for 20 minutes, and then wiped off. Zero point six-five (0.65) ml of a formulation comprising the above-buffered composition along with 9 g per 100 g of composition—i.e., 90 mg/ml of glutaric anhydride was applied and allowed to remain for 30 minutes. The formulation was then wiped off and the results evaluated 15 minutes later. FIGS. 1A and 1B show the results for the first subject wherein FIG. 1A shows the subject prior to treatment and FIG. 1B shows the subject 15 minutes subsequent to treatment. FIGS. 2A and 2B show the effects were still in place after about 4 months as shown in FIG. 2B.

Figure 3A:
FIGS. 3A and 3B show treatment of another subject for crow's feet using the formulations of the invention.
Figure 3B:

FIGS. 3A and 3B show comparable results before treatment and 15 minutes subsequent for the second subject.

Example 7

Photographic Description of Individual Patient Results

Figure 5A:
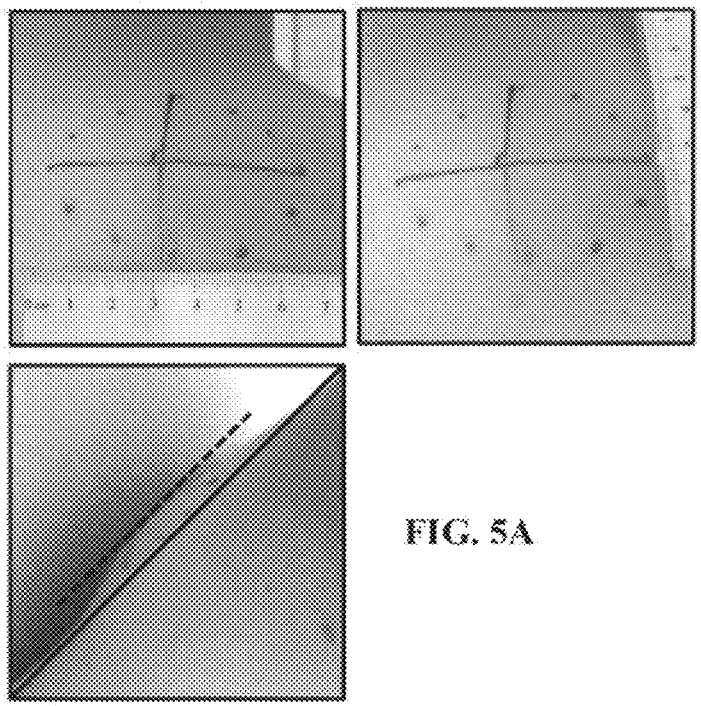
FIGS. 5A and 5B show the results of treatment of the same subject as FIGS. 4A and 4B, except the "After" depiction is one month subsequent to treatment.

An individual subject was administered a topical cream comprising 22% w/w deoxycholic acid; 0.8% w/w phosphatidylcholine, 1% w/w caffeine, 0.5% w/w arginine; 0.5% w/w L-carnitine, 2% w/w benzyl alcohol, 30% w/w lecithin isopropyl palmitate; and brought to 100% with an aqueous solution of 30% poloxamer. The cream was applied thinly to the area b.i.d. covered with Saran™ Wrap and held in place for 30 minutes. Before treatment, as indicated in FIGS. 4A and 5A, the dimensions of the fat deposit were 6.1×4.7 cm with the surface area of 22.5 cm². The height of deposit was 1.2 cm and the deposit was firm and clearly delineated. After 12 days, as shown in FIG. 4B, the dimensions had been reduced to 4.6×3.1 cm with a surface area of 12.2 cm² (a reduction of 50%) the height was reduced to 0.8 cm or reduction of 33%, and the deposit was softer and to borders were more difficult to define.

Figure 5B:
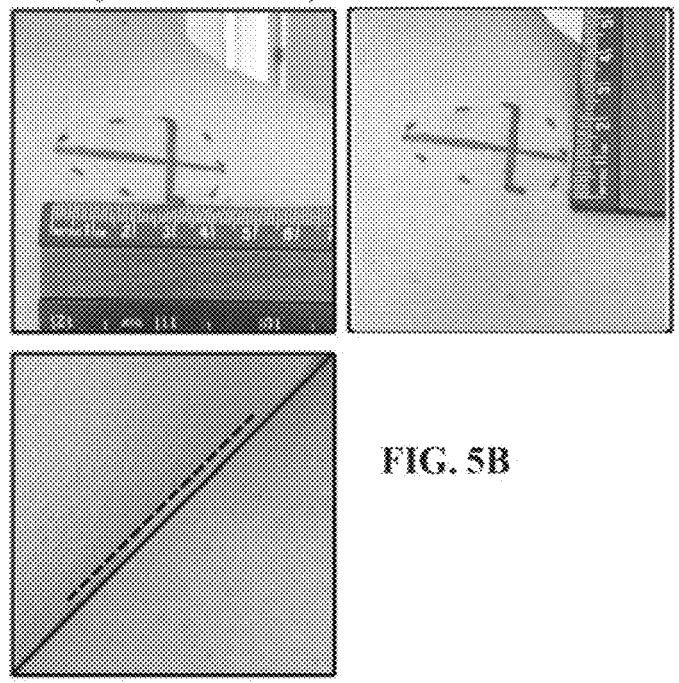

As shown in FIG. 5B after one month, the dimensions were reduced slightly more to 4.3×2.2 cm with a surface area of 7.1 cm² or an area reduction of about 67%. The height was clearly reduced to 0.5 cm or 58% reduction. The deposit was even softer and the borders even more difficult to define.

Example 8

Relief of Lactic Acidosis

A single subject was used in this test. One forearm was treated with a formulation which comprises:

11% w/w CarboPro® (a mixture of complex carbohydrates from various plants);

11% w/w sodium bicarbonate;

11% w/w whey protein powder;

1% w/w benzyl alcohol;

27% w/w soy lecithin isopropyl palmitate;

remainder 30% w/w Pluronic® (poloxamer) in water.

The other forearm was left untreated.

Acidosis was induced by having the subject perform 60 forearm flexions at the rate of 1 per second using a resistance band. This was repeated every 5 minutes. The subject was asked to report a burning sensation when acidosis occurred. The number of flexions the subject was able to perform at each 5-minute interval before experiencing burn was tested for each arm.

The first set was performed 5 minutes after treatment. The results were as follows.

| | Number of Flexions | |
|---|---|---|
| | Treated | Untreated |
| Time 0 | 16 | 16 |
| 5 minute set | 16 | 16 |
| 10 minute set | 18 | 14 |
| 15 minute set | 50 | 10 |
| 20 minute set | 40 | 5 |
| 25 minute set | 30 | 5 |
| 30 minute set | 25 | 4 |

Thus, over the course of the test, the treated arm could perform 195 repetitions as compared to 70 for the untreated. It appeared that the time for absorption of the formulation was between 10 and 15 minutes; if the last three timepoints after that were the only ones considered, the comparison was 120 for the treated arm vs. 20 for the untreated.

Example 9

Acidosis Test without Nutrients

In another experiment designed to test the ability of the formulation to impede lactic acidosis, again a single subject was used with one arm treated with a formulation containing:

33% w/w sodium bicarbonate;
1% w/w benzyl alcohol;
25% w/w soy lecithin isopropyl palmitate;
made up to 100% w/w with a 30% w/w solution of Pluronic® in water.

In this exercise, a "preacher curl" exercise with a fixed weight was employed and the number of repetitions performed by each arm before the subject reported failure due to burning was recorded. At the 0 timepoint, both arms performed approximately 50 repetitions; however, in the 10 minute exercise set, the treated forearm performed 77 as compared to 52 by the untreated arm; in the 20 minute set the treated forearm performed 62 compared to 46; and at 30 minutes, the treated forearm performed 44 as compared to 30 by the control.

Assuming absorption at 10 minutes, the total repetitions in the workouts at 10, 20 and 30 minutes were 183 for treated vs. 128 for untreated. Overall the total was 235 for treated vs. 176 for untreated.

Example 10

Lactic Acidosis Test Using Sodium Bicarbonate Plus Nutrients

Six individuals were used in this test, each having a treat calf and an untreated calf as a control.

The treatment formulation was:
1% w/w beta alanine;
4% w/w sodium bicarbonate;
1% w/w L-carnitine;
1% w/w adenosine triphosphate;
24% w/w dextrose;
1% w/w creatine monohydrate;
0.4% w/w beta-hydroxy-beta-methylbutyrate;
2% w/w branched chain amino acids (leucine, isoleucine, valine, 1:1:1);
1% w/w glutathione;
30% w/w soy lecithin isopropyl palmitate;
2% w/w benzyl alcohol;
Q.S. with 30% w/w poloxamer in water.

In this example, the exercise was calf flexion/heel raises 1 per 2 seconds repeated every 5 minutes. In this case, the control contained the penetrant alone. The results are shown in FIG. 6A-C. FIG. 6A shows the relative time to acknowledging lactic acidosis burn; FIG. 6B shows the relative time to notice pain and FIG. 6C shows the relative maximum number of repetitions. In each case these are calculated based on a 100% value at time zero.

As shown, there was a significant increase in the time until acidosis burn occurred and an increase in the time before threshold pain was felt. The maximum number of repetitions that could be performed was also measured and showed an increase for the treated legs. The results are shown as a percentage of performance at time zero.

Example 11

Systemic Glucose Absorption

A single subject was used in this study. After an overnight fast, 24 mg of a dextrose formulation in cream was applied to the upper body of the individual by a massage. The formulation was:
50% w/w dextrose;
1.3% w/w benzyl alcohol;
28% w/w soy lecithin isopropyl palmitate;
Q.S. with 30% w/w poloxamer in water.

The results were similar to those obtained with i.v. dextrose infusion. The blood glucose level in mg/dL was measured with a One-Touch Ultra® blood glucose meter. At time zero, the reading was 90 mg/dL but after 15 minutes the blood glucose level rose to almost 200 mg/dL and then declined by 50 minutes subsequent to the application of the formulation to about 100 mg/dL which was maintained at substantially this level for over 2 hours.

In addition, the subject, after the overnight fast, reported feeling hungry and wanting to eat, but 15 minutes after application of the formulation, the subject noted feeling completely satiated.

In addition, two additional subject who expressed hunger were able to assuage this hunger by application of the formulation described herein.

Example 12

Relief from Lactic Acidosis (Alternate Exercise Regime)

In this test, the formulation was:
40% w/w sodium bicarbonate;
1.7% w/w benzyl alcohol;
36% w/w soy lecithin isopropyl palmitate;
Q.S. 30% w/w poloxamer, buffered to pH 10-11.

In this example, the subjects were assigned 5 sets of pushups—to do as many as possible. The interval between sets was 3 minutes and 30 seconds. The formulation was applied 15 minutes prior to and immediately before the first set.

Figure 7:
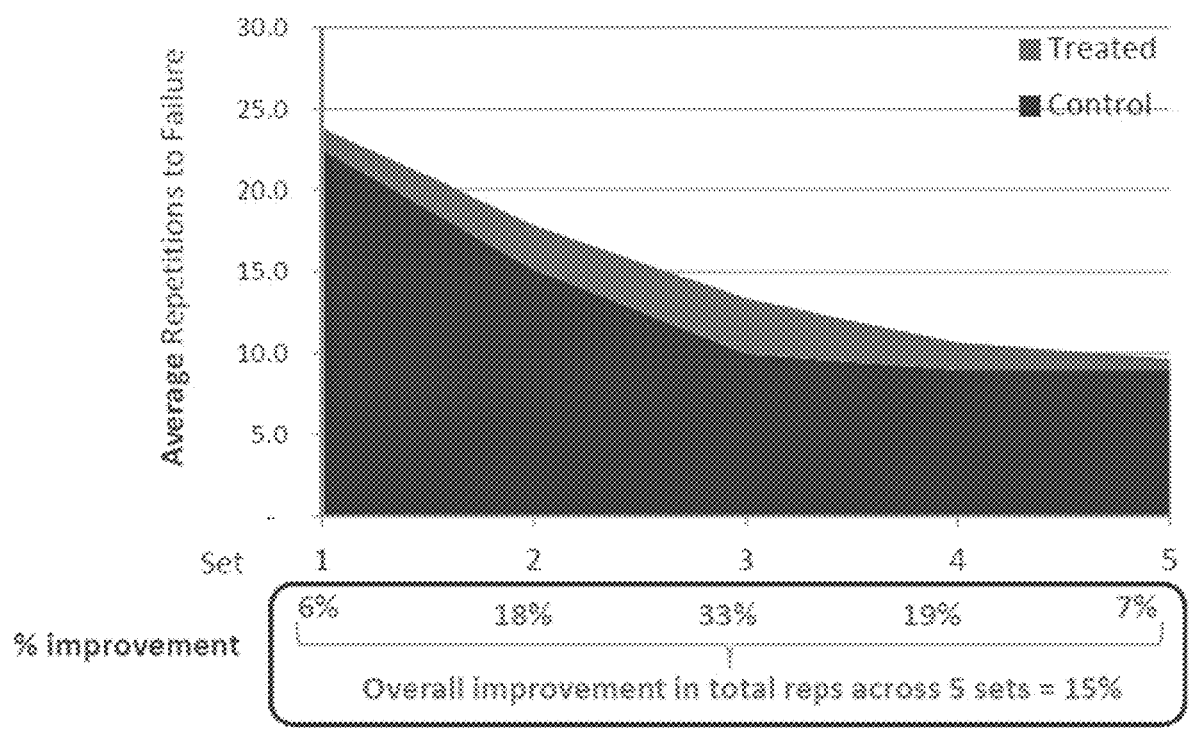
FIG. 7 shows a comparison of performance of treated and untreated controls in performing pushups across 5 sets.

Three subjects participated in the test. Controls were performed by testing the three subjects without treatment, then waiting three days and treating the three subjects and testing them again. Two such series of tests were performed. Thus, on day 1 the three subjects performed the pushups at the indicated time intervals without having been treated; on day 4 the three subjects were treated as described and then performed the pushup sets at the indicated intervals. On day 7 the subjects were again not treated but performed the required exercises and on day 10 the exercises were performed after treatment as described above. The results are shown in FIG. 7 which is a graph showing the average repetitions for all three subjects at each set.

Improvement at each set was shown, particularly in the middle set before exhaustion was reached. Thus, in the first series of experiments, the improvement at set 1 was 6%, at set 2 was 18%, at set 3 was 33%, at set 4 was 19% and at set 5 was 7%, with the overall improvement in totals across all five sets at 15%. When the experiment was repeated, i.e., in the second series of tests, the controls performed better than the controls in the first set. Based on 100% performance on the first set by controls, the controls performed at 114%, but when treated in this second test, their performance level was 128% of the original controls showing an improvement of 14% over the corresponding controls in the second set.

Example 13

Stimulation of Hair Growth

The subject in this example exhibits male pattern baldness. The composition applied was 0.015% w/w bimatoprost from 0.03% commercially available Latisse® by 0.015% w/w bimatoprost, 2% w/w benzyl alcohol, 33% w/w soy lecithin isopropyl palmitate topped off with 20% Pluronic® in aqueous solution for 4 weeks. The composition was applied to the scalp at a level of 0.1 ml/2 cm$^2$ b.i.d.—i.e., twice per day. The results were assessed after this time.

Figure 8A:
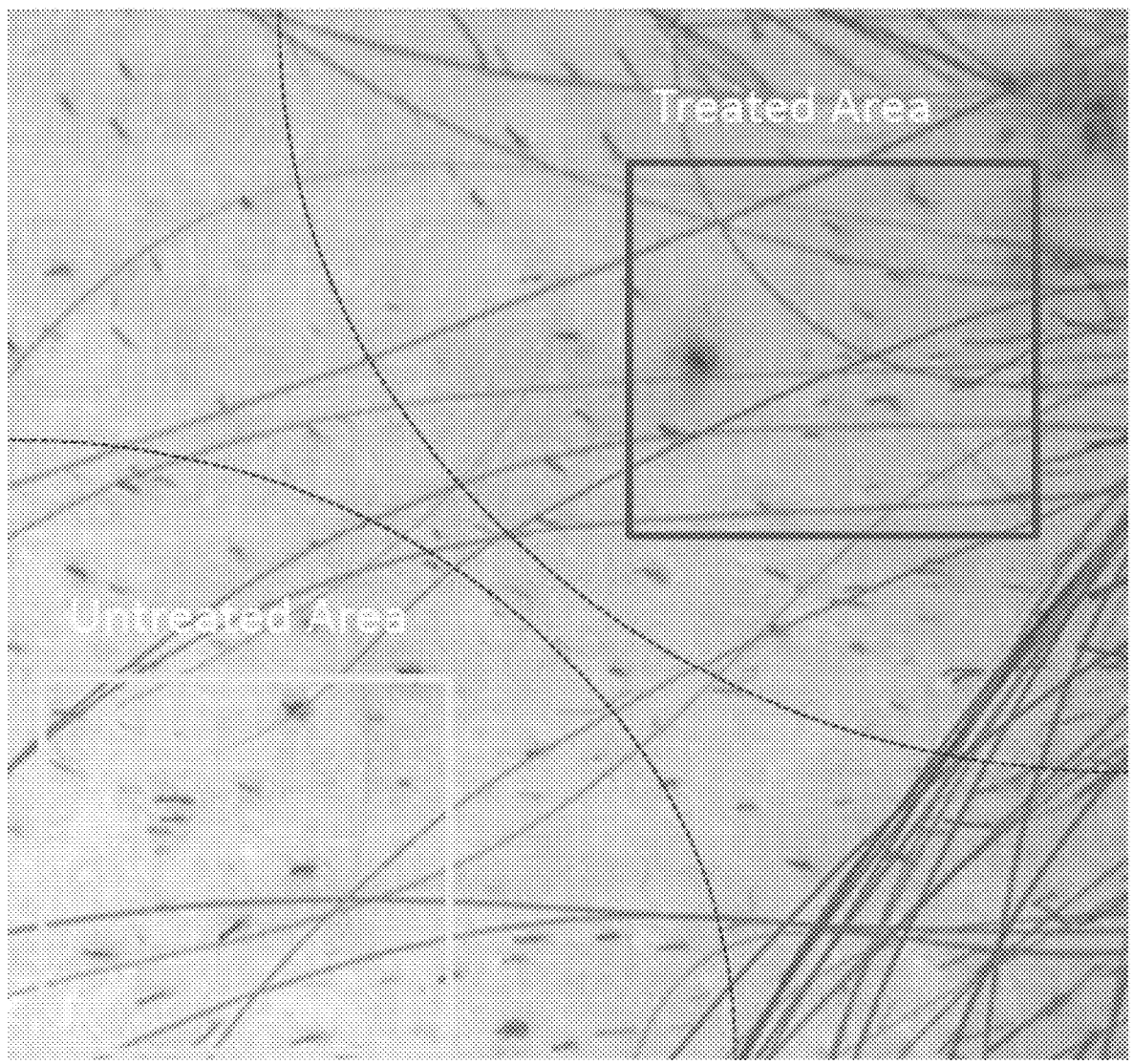
FIGS. 8A and 8B show an overview of a section of the scalp of a subject treated with the invention compositions before and after treatment indicating the treated and untreated areas.
Figure 8B:
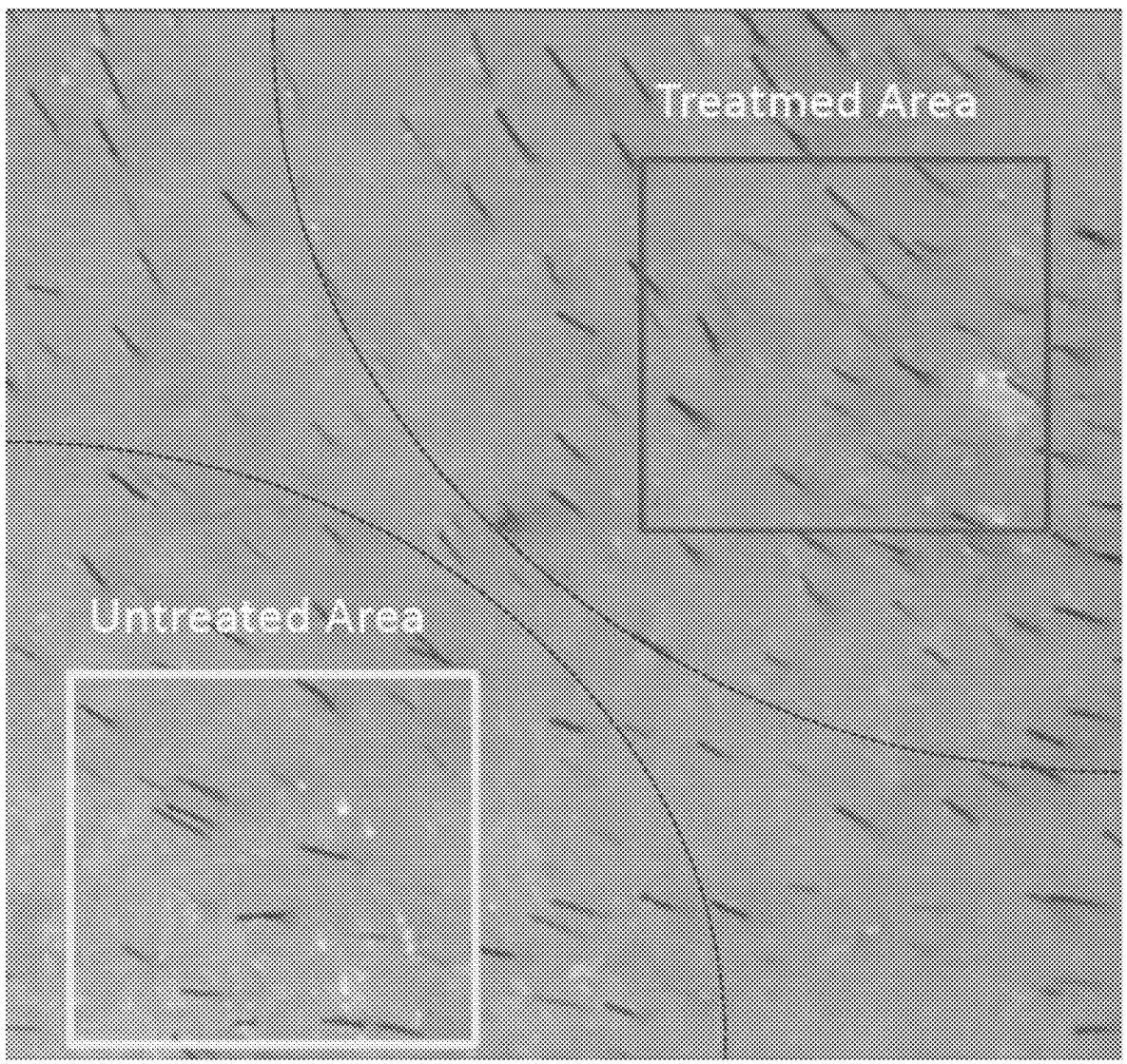

FIGS. 8A and 8B show generally the scalp of the treated subject with the treated area and untreated area delineated before (FIG. 8A) and after (FIG. 8B) 4 weeks.

Figure 9A:
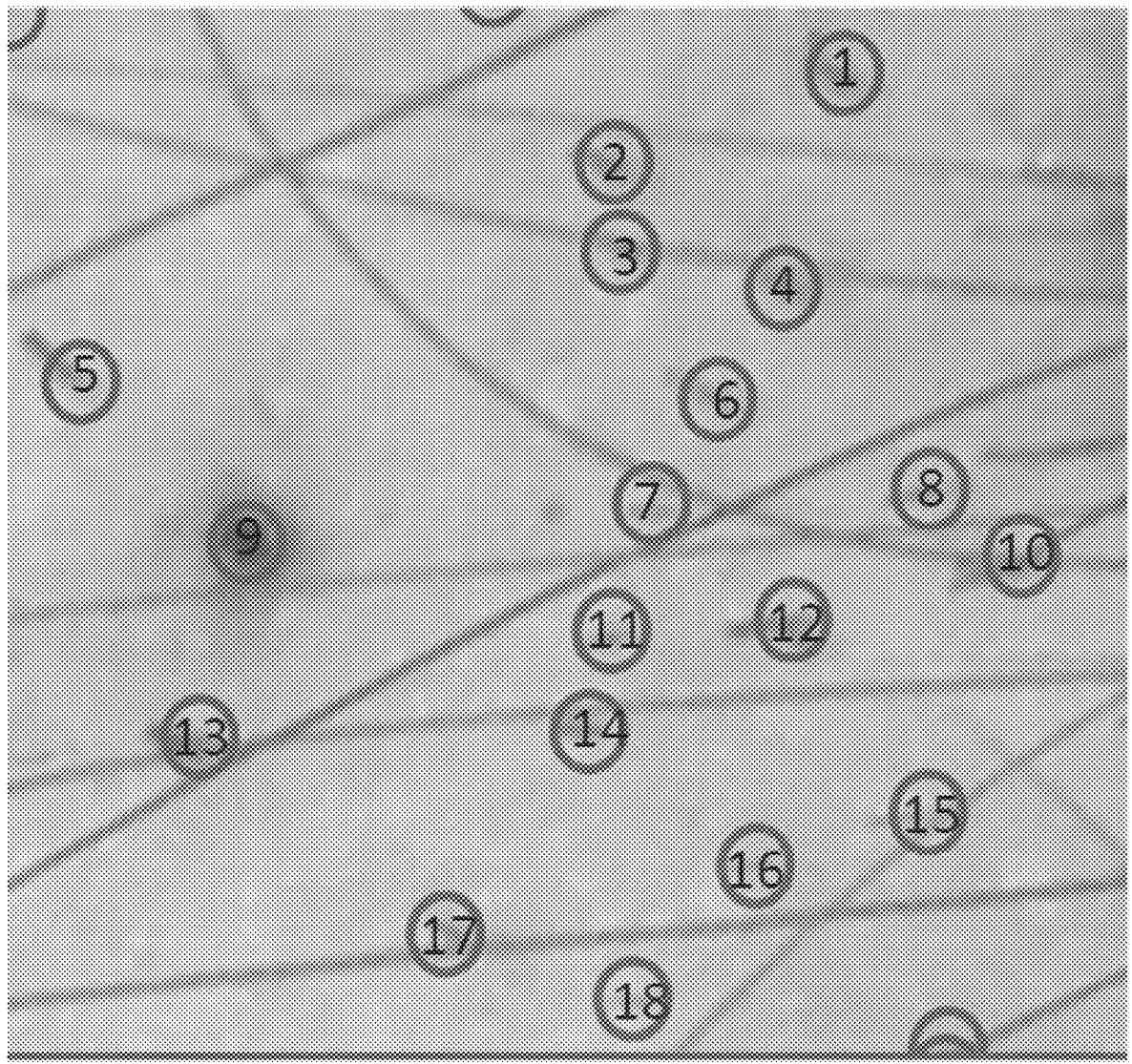

FIGS. 9A and 9B show a comparison of the treated area before (FIG. 9A) and after (FIG. 9B) treatment over the 4 week period.

As shown, the hair follicles existing at the beginning of treatment remained at the end of treatment, but the hair was thicker and darker in the treated portion. In addition, the lighter circles in FIG. 9B indicate new hair growth from follicles not previously seen. The darker circles indicate the existing hair. Overall, the existing hair was represented by 18 strands and there were 8 strands of new hair.

Figure 10A:
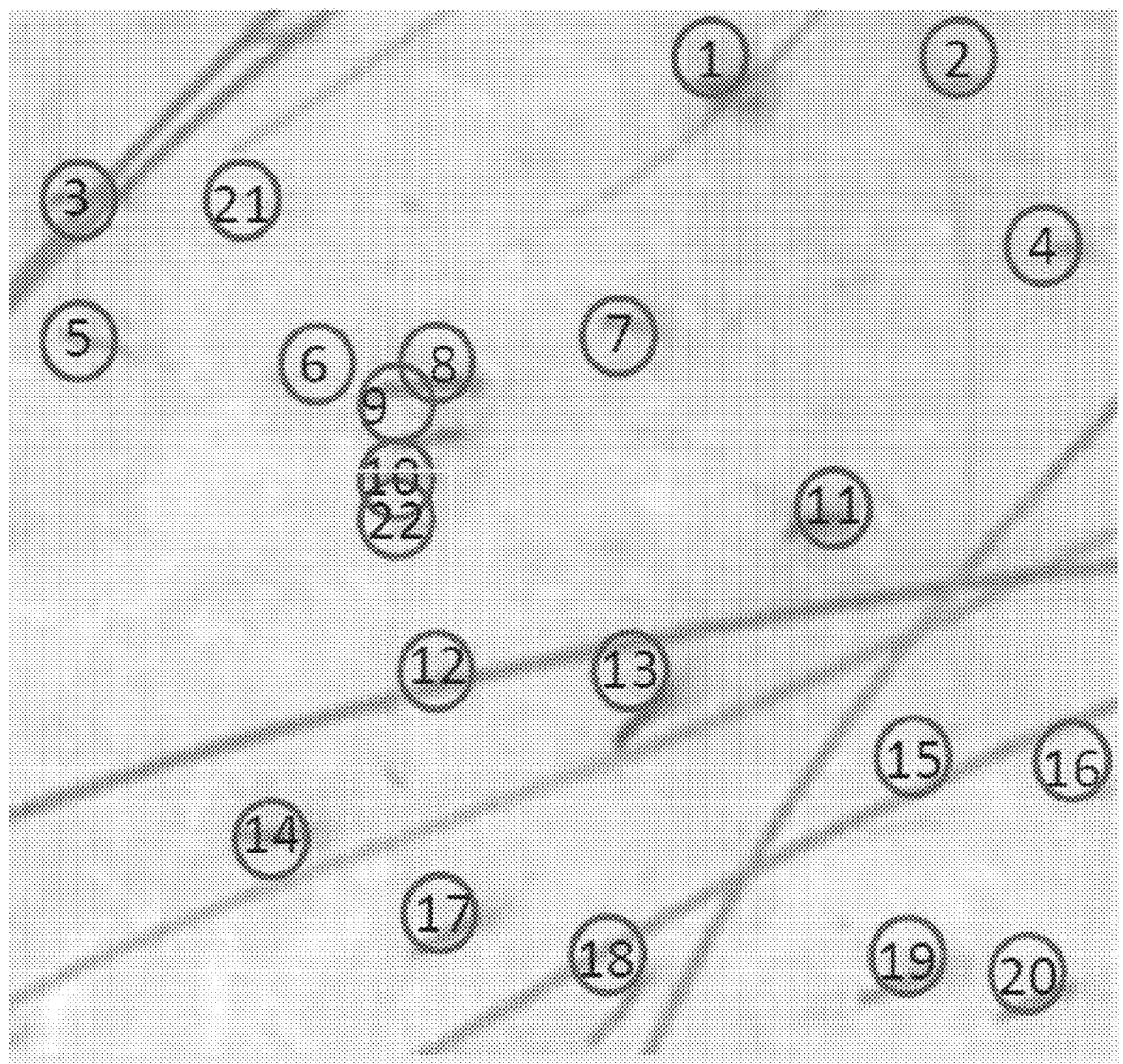
FIGS. 10A and 10B show a comparison of the untreated area before and after the time period used in the treatment shown in FIGS. 9A and 9B.
Figure 10B:
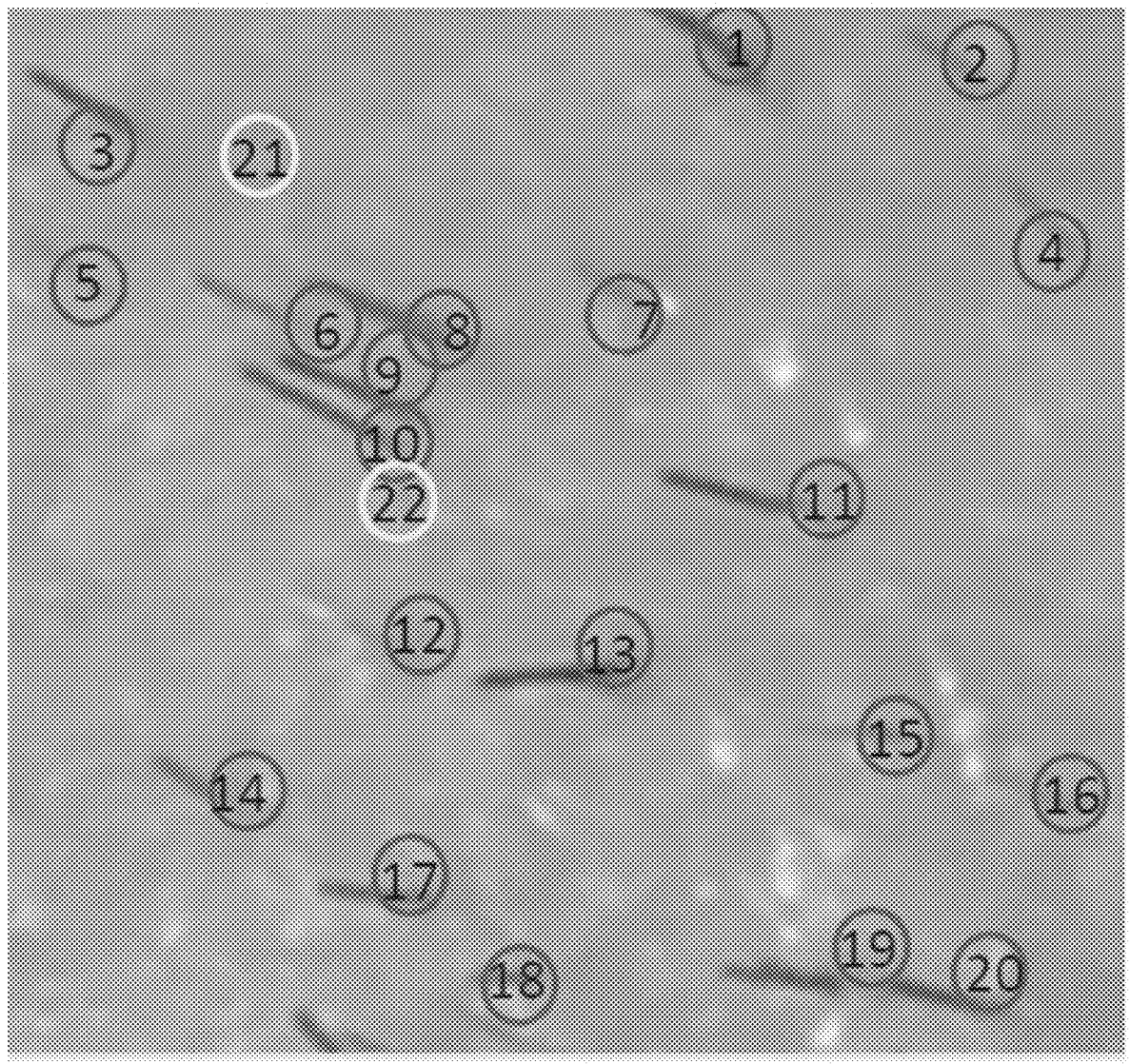

This is in contrast to the untreated area of the same scalp which is shown in FIG. 10A (before treatment) and FIG. 10B (the untreated portion 4 weeks later). Again, the circles indicate the location of hair follicles before and after. As seen, the existing hair before the start of the experiment represented 22 follicles and 2 of these were lost in the untreated portion.

Example 14

Stimulation of Hair Growth by 0.3% w/w Bimatoprost

Figure 11A:
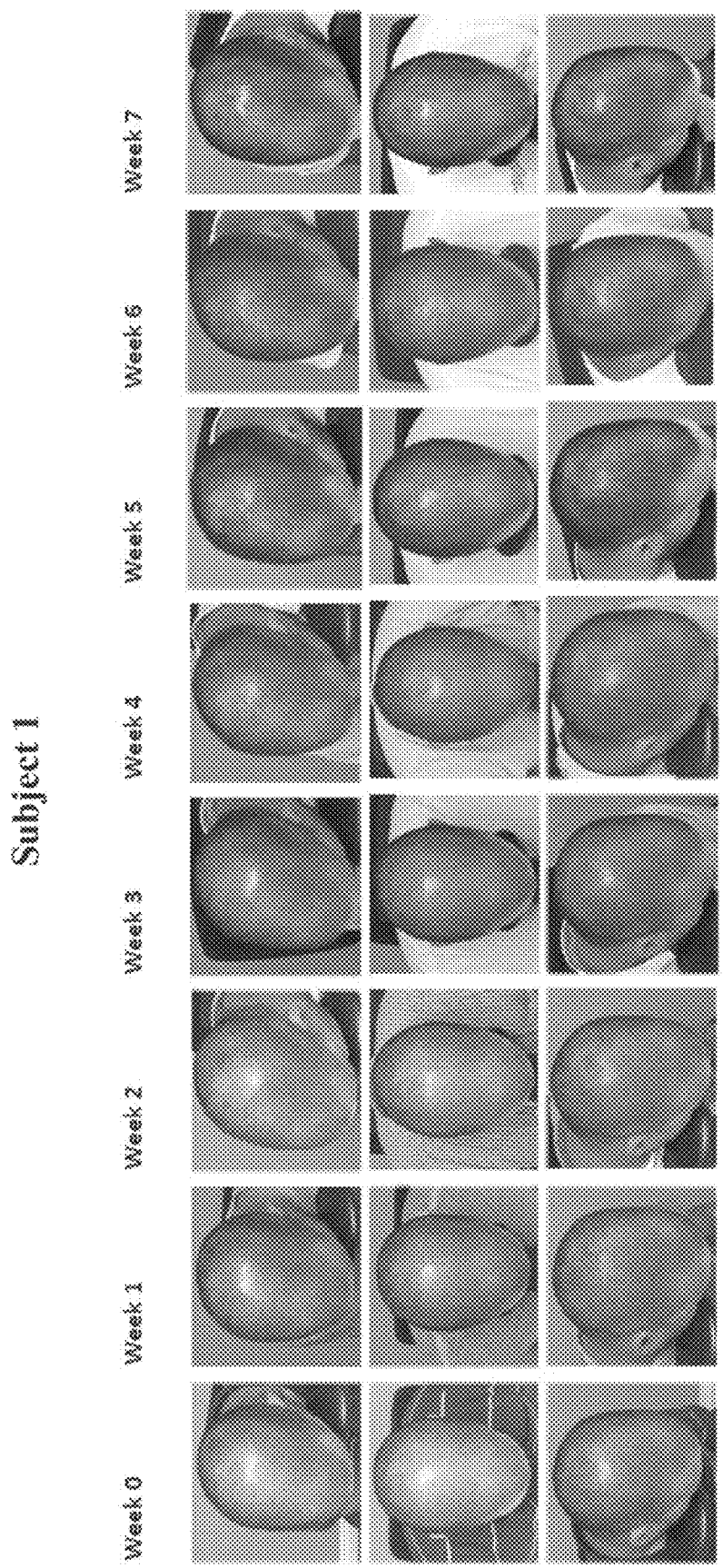
FIGS. 11A and 11B show photographs of overall hair growth exhibited by each of two subjects with concentrations of bimatoprost in the invention formulations of 0.015% w/w and 0.3% w/w, respectively.
Figure 11B:
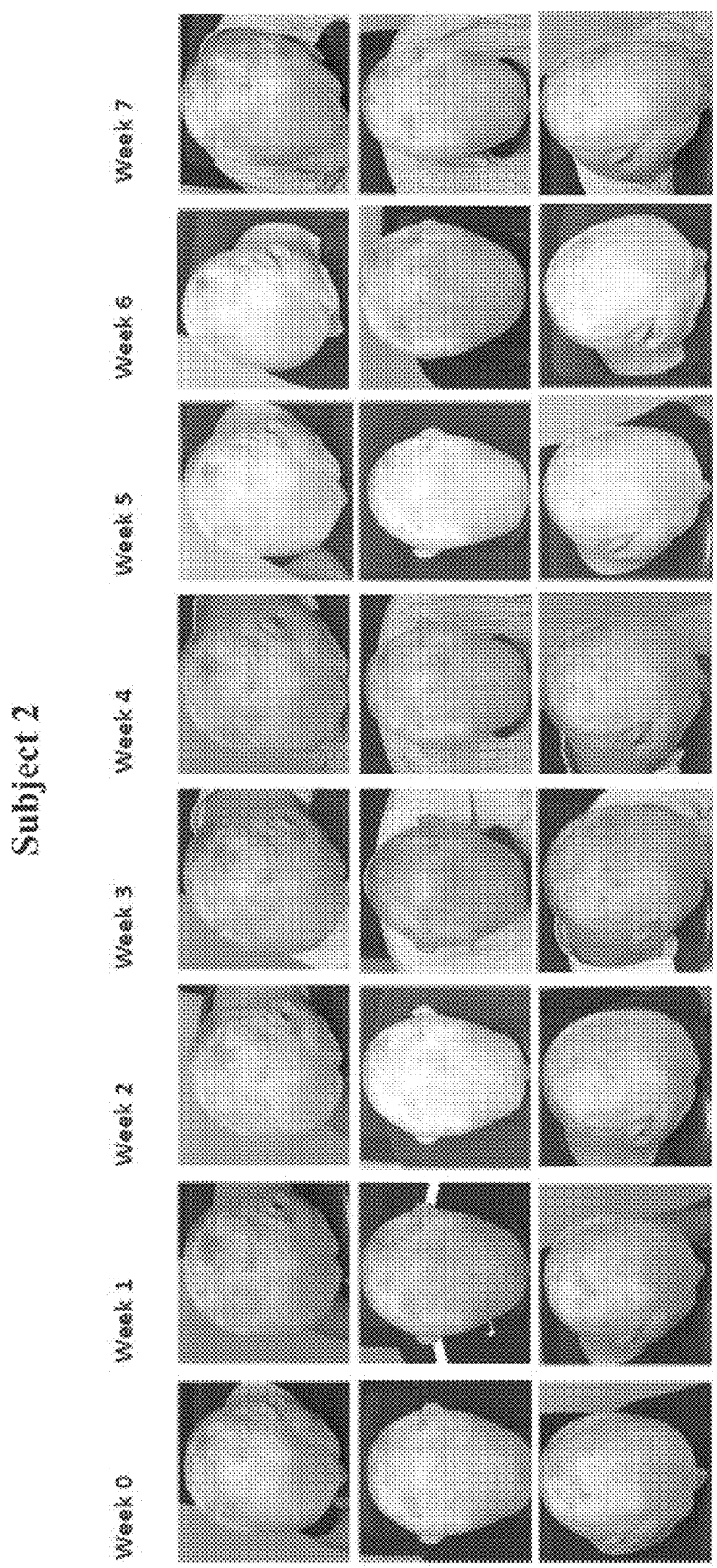
Figure 14B:
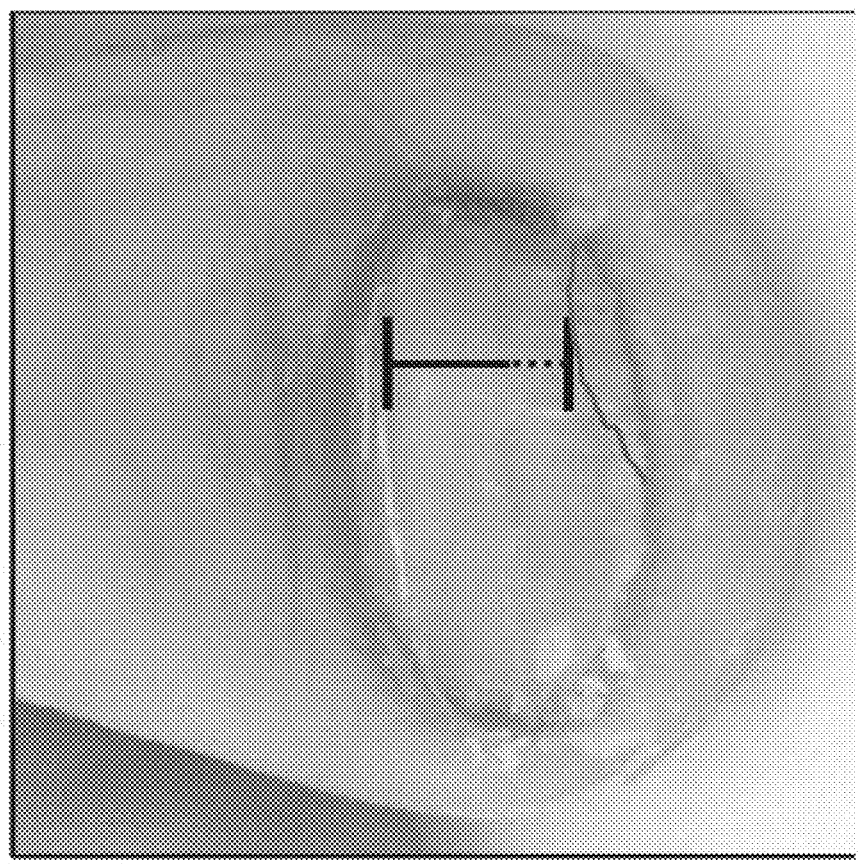
Figure 14A:
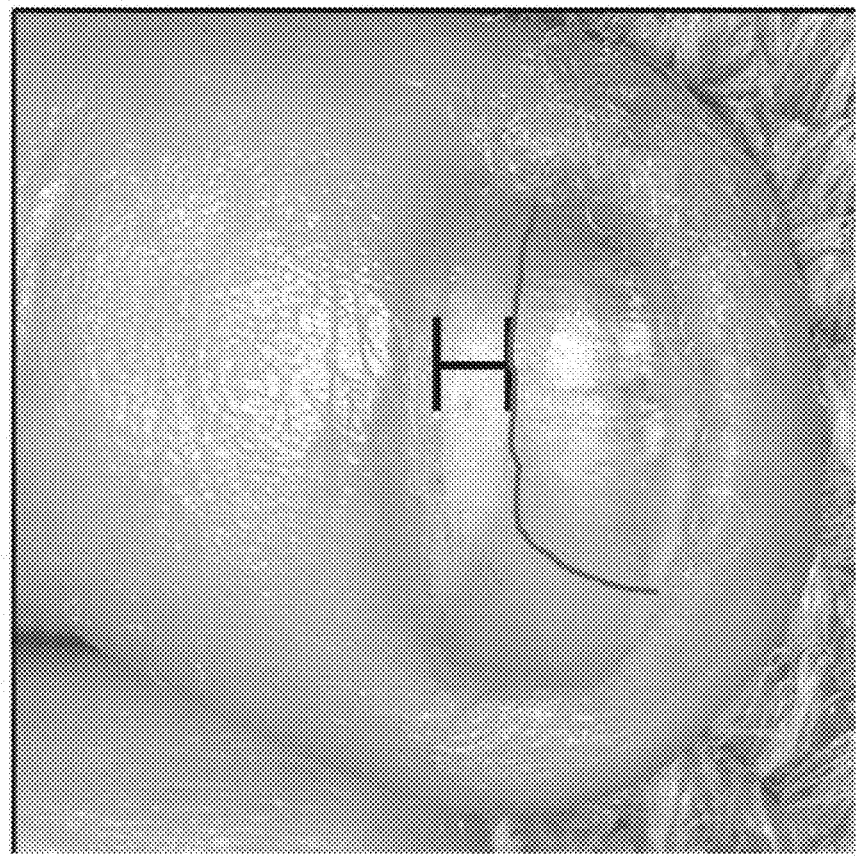

Two subjects that exhibited male pattern baldness were used in this example. The composition applied was 0.3% w/w bimatoprost, 1% benzyl alcohol, 33% soy lecithin isopropyl palmitate organogel topped to 100% with 30% poloxamer at pH 7.8. The 30% poloxamer is Pluronic® in aqueous solution. One ml was applied over the entire crown twice a day over a 7 week period. Subjects were photographed each week as shown in FIGS. 11A and 11B. In each case, for photography, the hair was trimmed (to ⅛ of an inch) a day prior to the pictures. The global photographs were taken with an Apple iPhone 6s using a desk-mounted tripod and a stereotactic head positioning device under standardized lighting conditions.

FIGS. 12A and 12B show enlarged views of the overall hair growth after 7 weeks for each of the subjects.

In addition, similar to the procedure in Example 13, 1 cm$^2$ areas of the scalp of each subject were photographed and the number of hair follicles counted at 4 weeks for each subject. The results for subjects 1 and 2 are shown below in Table 5 and Table 6.

TABLE 5

Subject 1

| | Follicles per cm$^2$ | | | | |
|---|---|---|---|---|---|
| | Baseline | Lost | Gained | Final | Net change |
| | 10 | 0 | 4 | 14 | 40% |
| | 14 | 5 | 9 | 18 | 29% |
| | 23 | 10 | 14 | 27 | 17% |
| Average | 15.7 | 5.0 | 9.0 | 19.7 | 25.5% |

TABLE 6

Subject 2

| | Follicles per cm$^2$ | | | | |
|---|---|---|---|---|---|
| | Baseline | Lost | Gained | Final | Net change |
| | 6 | 2 | 7 | 11 | 83% |
| | 13 | 8 | 12 | 17 | 31% |
| | 8 | 3 | 3 | 8 | 0% |
| Average | 9.0 | 4.3 | 7.3 | 12.0 | 33.3% |

As shown, considerable variation depending on the sample area selected is shown, but subject 1 showed an overall increase in hair follicles of 25.5% over 4 weeks and subject 2 showed an overall increase of 33.3% hair follicles over 4 weeks.

While the sampling in Example 13 was limited, it appears that comparable results were achieved whether the bimatoprost was used at 0.015% as in Example 13 or at 0.3% as in Example 14—after 4 weeks the sample selected in Example 13 showed a 44% increase. In addition, in Example 13 only 0.1 ml was applied per cm$^2$ whereas in Example 14 1 ml of formulation was applied per cm$^2$. The essentially flat dose response curve is advantageous in view of the known induction of undesirable side effects with higher concentrations of bimatoprost in commercial preparations.

In addition, as compared to published studies with commercially available Rogaine™, the results appear to achieve at 4-7 weeks what Rogaine™ requires 12 months of treatment to obtain. Indeed, these studies showed evidence of hair growth was not demonstrated until after 8 months of treatment with concentrations of 2% and 5% of minoxidil.

Example 15

Regrowth of Hair Lost in Chemotherapy

Compositions were prepared that comprise bimatoprost in varying amounts including 4.0%, 10%, 15%, and 30% w/w. The compositions also comprised benzyl alcohol in an amount of 2% w/w and lecithin isopropyl palmitate in an amount of 30% w/w. The remainder was a stock cream formulation such as that sold as VaniCream™. No poloxamer was included in the composition.

Example 16

Compositions Containing Detergent

Compositions were prepared that comprised minoxidil in varying amounts including 4.0% and 30% w/w. The compositions also comprised benzyl alcohol in an amount of 2% w/w, lecithin isopropyl palmitate in an amount of 40% w/w. In composition #1, poloxamer PEG/propylene glycol (20% w/w by volume of solution) was used top off the composition to 100% by weight of the composition. In composition #2, Aquaphor® sold by Eucerin® was used to top off the benzyl alcohol and lecithin isopropyl palmitate instead of poloxamer.

Example 17

Effect of Lecithin Organogel Concentration

Compositions were prepared that comprised minoxidil in an amount of 5.0% w/w. The compositions also comprised benzyl alcohol in an amount of 2% w/w, lecithin isopropyl palmitate in amounts of 30%, 40%, 50% and 60% w/w, and the composition was topped off with aqueous solutions of poloxamers to yield 100% of the composition w/w.

Example 18

Treatment of Onychomycosis

A. The formulation used in this example is 10% terbinafine (an allyl amine antifungal of the structure

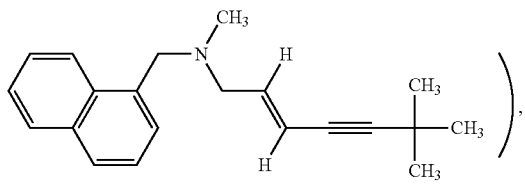

2% benzyl alcohol, 40% lecithin isopropyl palmitate (LIP), 13.4% poloxamer and the remainder water. The composition contains the terbinafine in a micellular support system generated by the carrier. The formulation (5 ml) was applied to toenails exhibiting onychomycosis of three individuals twice daily for a period of three weeks. After each application, a band-aid was placed over the area of application for one hour to prevent loss and to encourage penetration.

After three weeks of the treatment, the fungal condition of each individual had cleared. This is shown in FIGS. 13A-B, 14A-B and 15A-B. As shown for example in FIG. 14A-B, nail growth occurred over this time and the infected nail lifted after three weeks and revealed healthy nail growth underneath. This is in contrast to the commercially available Jublia® topical which requires 48 weeks of treatment for positive results.

B. The treatment protocol of paragraph A is performed but using, in the formulation on a weight basis, 1% terbinafine, 5% terbinafine, 15% terbinafine or 20% terbinafine. The remaining components are present at the same concentrations as in paragraph A. The formulations are applied to fingernails exhibiting onychomycosis as described in paragraph A and on the same schedule.

C. The procedure of paragraph A is followed except the poloxamer is omitted from the formulation. The formulation is applied to the affected nails and immediately covered with adhesive tape which remains in contact with the nail for 30 minutes. After two weeks of daily application, the results are evaluated.

D. The procedure of paragraph B is performed except that poloxamer is omitted from the formulation. The formulation is applied to the affected nails, covered with masking tape and left in contact for 15 minutes. The procedure is repeated every other day for six weeks and the results are evaluated.

E. The procedure of paragraphs A-D are performed but substituting for terbinafine, alternate allyl amines.

F. The procedure of paragraphs A-D are performed but substituting for terbinafine, fenticonazole, ravuconazole, caspfungin, ciclopirox, flucytosine or undecylenic acid.

G. The procedures of paragraphs A-D are performed but substituting for terbinafine one of the antifungal fluconazole, aculeacin A (echinocandin) or tavaborole. In each case, the results are evaluated visually.

H. The procedures of paragraphs A-D are performed but using a combination of 5% w/w fluconazole and 5% w/w terbinafine as active ingredients.

The procedures of A-H are performed except the formulation is administered to areas of the skin beyond the toe that exhibit fungal infection.

Example 19

Treatment of Psoriasis

A. The formulation used in this example is on a weight basis: 5% of the anti-inflammatory diclofenac, 1% benzyl alcohol, 30% lecithin isopropyl palmitate (LIP), 18% poloxamer and the remainder water. The composition contains the diclofenac in a micellular support system generated by the carrier. The formulation (5 ml) is applied to nails exhibiting psoriasis twice daily for a period of three weeks. After each application, an impermeable cover was placed over the area of application for 0.5 hours to prevent loss and to encourage penetration. After two weeks of the treatment, the results are evaluated.

B. The procedure of paragraph A is followed except that the anti-inflammatory celecoxib was substituted for diclofenac.

C. The procedure of paragraph A is followed except that the diclofenac is supplied at 5% w/w, 15% w/w or 20% w/w.

D. The procedure of paragraphs A-C is performed except that the formulation contained no poloxamer.

E. The procedure of paragraphs A-C is performed except that the percentage of poloxamer is 10% w/w.

F. The procedure of paragraphs A-E is performed except that the agent is applied to areas of the skin that exhibit psoriasis Example 20

Treatment of Onychomycosis

A. The formulation used in this example is 4% efinaconazole, 2% benzyl alcohol, 40% lecithin isopropyl palmitate (LIP), 13.4% poloxamer and the remainder water. The composition contains the efinaconazole in a micellular support system generated by the carrier. The formulation (5 ml) is applied to toenails exhibiting onychomycosis of three individuals twice daily for a period of three weeks. After each application, a band-aid is placed over the area of application for one hour to prevent loss and to encourage penetration.

B. The treatment protocol of paragraph A is performed but using, in the formulation on a weight basis, 1% efinaconazole, 5% efinaconazole, 15% efinaconazole or 20% efinaconazole. The remaining components are present at the same concentrations as in paragraph A. The formulations are applied to fingernails exhibiting onychomycosis as described in paragraph A and on the same schedule.

C. The procedure of paragraph A is followed except the poloxamer is omitted from the formulation. The formulation is applied to the affected nails and immediately covered with adhesive tape which remains in contact with the nail for 30 minutes. After two weeks of daily application, the results are evaluated.

D. The procedure of paragraph B is performed except that poloxamer is omitted from the formulation. The formulation is applied to the affected nails, covered with masking tape and left in contact for 15 minutes. The procedure is repeated every other day for six weeks and the results are evaluated.

H. The procedures of paragraphs A-D are performed but using a combination of 5% w/w efinaconazole and 5% w/w terbinafine and/or fluconazole as active ingredients.

Example 21

Treatment of Athlete's Foot

A. The formulation used in this example is 10% terbinafine, 2% benzyl alcohol, 40% lecithin isopropyl palmitate (LIP), 13.4% poloxamer and the remainder water. The composition contains the terbinafine in a micellular support system generated by the carrier. The formulation (35 ml) is applied twice daily for a period of four weeks to the skin of the feet of four individuals exhibiting the symptoms of athlete's foot. After each application, a covering is placed over the area of application for one hour to prevent loss and to encourage penetration. After four weeks of the treatment, the athlete's foot symptoms are ameliorated.

B. The treatment protocol of paragraph A is performed but using, in the formulation on a weight basis, 1% tavaborole, 5% tavaborole, 15% tavaborole or 20% tavaborole. The remaining components are present at the same concentrations as in paragraph A. The formulations are applied to the feet of subjects exhibiting the symptoms of athlete's foot as described in paragraph A and on the same schedule.

C. The procedure of paragraph A is followed except the poloxamer is omitted from the formulation. The formulation is applied to the affected feet of subjects exhibiting the symptoms of athlete's foot and immediately covered with adhesive tape for 30 minutes. After two weeks of daily application, the results are evaluated.

D. The procedure of paragraph B is performed except that poloxamer is omitted from the formulation. The formulation is applied to the affected feet of subjects exhibiting the symptoms of athlete's foot, covered with masking tape and left in contact for 15 minutes. The procedure is repeated every other day for six weeks and the results are evaluated.

E. The procedures of paragraphs A-D are performed but substituting efinaconazole for terbinafine or tavaborole.

F. The procedures of paragraphs A-D are performed but substituting fenticonazole, ravuconazole, caspfungin, ciclopirox, flucytosine or undecylenic acid as the antifungal agent.

G. The procedures of paragraphs A-D are performed but substituting one of the antifungal fluconazole or aculeacin A (echinocandin) as antifungal agent. In each case, the results are evaluated visually.

H. The procedures of paragraphs A-D are performed but using a combination of 5% w/w fluconazole and 5% w/w terbinafine as active ingredients.

Example 22

Treatment of Jock Itch

A. The formulation used in this example is 4% efinaconazole, 2% benzyl alcohol, 40% lecithin isopropyl palmitate (LIP), 13.4% poloxamer and the remainder water. The composition contains the efinaconazole in a micellular support system generated by the carrier. The formulation (5 ml) is applied to the groin of subjects showing symptoms of jock itch daily for a period of two weeks. After each application, a bandage is placed over the area of application for one hour to prevent loss and to encourage penetration.

B. The treatment protocol of paragraph A is performed but using, in the formulation on a weight basis, 1% efinaconazole, 5% efinaconazole, 15% efinaconazole or 20% efinaconazole. The remaining components are present at the same concentrations as in paragraph A. The formulations are applied to the groin of subjects showing symptoms of jock itch as described in paragraph A and on the same schedule.

C. The procedure of paragraph A is followed except the poloxamer is omitted from the formulation. The formulation is applied to the groin of subjects showing symptoms of jock itch. After two weeks of daily application, the results are evaluated.

D. The procedure of paragraph B is performed except that poloxamer is omitted from the formulation. The formulation is applied to the groin of subjects showing symptoms of jock itch, covered with a bandage and left in contact for 15 minutes. The procedure is repeated every other day for six weeks and the results are evaluated.

H. The procedures of paragraphs A-D are performed but using a combination of 5% w/w tavaborole and 5% w/w terbinafine and/or fluconazole as active ingredients.

Example 23

Micelle Production and Milling Procedures

A. The formulation used in this example is 4% lidocaine, 1% menthol, 0.9% benzyl alcohol, 30% lecithin isopropyl palmitate, buffered to pH 10, and brought to volume with a 30% Pluronic® solution.

B. The formulation was milled using a Dermamill 100 (Blaubrite) using the following parameters: X-Y-Z; where X is the speed of the milling machine rollers from 1 to 100, where 1 is the slowest and 100 is the fastest; Y is pressure from 1 to 5, where 1 is the highest pressure and 5 is the lowest pressure; and Z is the number of passes through the milling machine. One pass was considered complete when all of the product passed through the machine. For example, a milling procedure represented by X-Y-Z, X-Y-Z has the same format as described herein but it has two phases of milling.

Micelle density was examined using an Omano OM88 clinical light microscope and Moticam 1SP microscope camera. Images were captured under light microscopy at 64× magnification, taking care to ensure that the images were representative of the entire sample. The images were centered on a 10×10 grid; each cell containing visible micelles was marked, and all the marked cells were counted and the total divided by 100 to give the percent density. Representative images are shown in FIG. 16A-D.

As shown, increasing pressure (FIG. 16A vs. C or B vs. D) and/or increasing milling speed (FIG. 16B vs. A or D vs. C) resulted in higher density of micelles in general.

Example 24

Micelle Density and Attenuation of Pain Relief

The composition of Example 23 was milled at different values of X-Y-Z.

Ultherapy was used to induce pain at specific depths of 1.5 mm, 3.0 mm and 4.5 mm. The default/maximum power was used for this test.

The formulations were applied on the thighs of two subjects on adjacent areas of close proximity to reduce the likelihood of pain sensitivity variation. The test was also repeated on 3 other areas: cheeks, upper arms, and lower arms. On either side of each sample, untreated areas were marked off as control. Each sample was assigned a pain attenuation score by testing the control on one side, then the sample, and then the control on the other side to account for possible pain sensitivity variation. Each formula was tested at 1.5 mm, 3.0 mm, and 4.5 mm, on 2 subjects. Three (3) depths×2 people=>n=6 test spots for each formula. Each test spot was assessed as a treated area, and 2 untreated controls directly adjacent to the treated area.

Below are the averaged results.

| Milling Procedure | Micelle Density | Pain Attenuation (Average) |
|---|---|---|
| 100-1-3 | 77% | 50% |
| 50-1-3 | 88% | 48% |
| 100-5-3 | 57% | 33% |
| 50-5-3 | 33% | 34% |

Micellar density vs. pain attenuation is plotted in FIG. 17.

Thus pain attenuation was correlated with density of micelles.

Example 25

Synergistic Effect on Pain Attenuation Using Two Formulations

A. The formulations used in this example are as follows:
1) 4% lidocaine, 1% menthol, 0.9% benzyl alcohol, 30% lecithin isopropyl palmitate, buffered to pH 10, and brought to volume with a 30% Pluronic® solution, labeled below as "Procicept L."
2) 20% benzocaine, 1% menthol, 0.9% benzyl alcohol, 30% lecithin isopropyl palmitate, buffered to pH 10, and brought to volume with a 30% Pluronic® solution, labeled below as "Procicept B."
3) A combination treatment of L and B wherein L is applied first, followed immediately (without wiping off) by B. labeled below as "Procicept L+B."

B. Ultherapy was used to induce pain at specific depths of 1.5 mm, 3.0 mm and 4.5 mm using the protocol of Example 24. The maximum power was used for this test.

Below are the results, in terms of pain attenuation.

| Formulation | 1.5 mm | 3.0 mm | 4.5 mm | Average |
|---|---|---|---|---|
| Procicept L | 41% | 75% | 42% | 51% |
| Procicept B | 35% | 39% | 32% | 35% |
| Procicept L + B | 63% | 75% | 64% | 68% |

The invention claimed is:

1. An anhydrous formulation for transdermal delivery of an active agent through the skin of a subject,
   wherein said active agent comprises a dicarboxylic selected from maleic anhydride, succinic anhydride, glutaric anhydride, citraconic anhydride, methylsuccinic anhydride, itaconic anhydride, methylglutaric anhydride or phthalic anhydride,
   wherein the dicarboxylic acid anhydride is in an amount effective for treatment of a condition requiring volume enhancement of tissue in said subject,
   wherein said formulation comprises a penetrant that provides an alcohol at 0.5-20% w/w of said formulation, lecithin organogel at 40-70% w/w of said formulation, nonionic surfactant at 20-60% w/w of the formulation and bile salt at 1-15% w/w of the formulation,
   wherein the surfactant is provided in powdered form,
   wherein said lecithin organogel comprises 1,2-diacyl-sn-glycero-3-phosphatidyl choline, and at least one of ethyl laureate, ethyl myristate, isopropyl myristate, isopropyl palmitate; cyclopentane, cyclooctane, trans-decalin, trans-pinane, n-pentane, n-hexane, n-hexadecane, and tripropylamine.

2. The formulation of claim 1 which further includes an inhibitor of hyaluronidase and/or an enhancer of hyaluronic acid (HA) synthase.

3. The formulation of claim 2 wherein the inhibitor of hyaluronidase is a flavonoid, non-flavonoid polyphenols, alkaloids, terpenoids, or an anti-inflammatory drug and the enhancer of HA synthase is a retinoid.

* * * * *